US007151202B1

(12) United States Patent
Yamada et al.

(10) Patent No.: US 7,151,202 B1
(45) Date of Patent: Dec. 19, 2006

(54) ENVIRONMENTAL STRESS RESISTANCE GENE

(75) Inventors: Akiyo Yamada, Hachioji (JP);
Yoshihiro Ozeki, Higashikurume (JP);
Takeo Saito, Tokyo (JP)

(73) Assignee: Japan Science and Technology Agency, Saitama (JP)

( * ) Notice: Subject to any disclaimer, the term of this patent is extended or adjusted under 35 U.S.C. 154(b) by 698 days.

(21) Appl. No.: 10/031,331

(22) PCT Filed: Jul. 19, 2000

(86) PCT No.: PCT/JP00/04862

§ 371 (c)(1),
(2), (4) Date: Jan. 18, 2002

(87) PCT Pub. No.: WO01/06006

PCT Pub. Date: Jan. 25, 2001

(30) Foreign Application Priority Data

Jul. 19, 1999 (JP) ............................ 11-235910
Mar. 24, 2000 (JP) ............................ 2000-085377

(51) Int. Cl.
*C12N 15/09* (2006.01)
*C12N 15/29* (2006.01)
*C12N 15/82* (2006.01)
*A01H 5/00* (2006.01)
*A01H 5/10* (2006.01)

(52) U.S. Cl. .................. 800/278; 800/298; 800/289; 435/320.1; 435/468; 435/430; 435/430.1; 536/23.6

(58) Field of Classification Search ............. 800/289, 800/278, 298, 295; 435/69.1, 320.1, 468, 435/430.1; 536/23.6, 23.2; 436/23.6
See application file for complete search history.

(56) References Cited

U.S. PATENT DOCUMENTS 4,946,778 A   8/1990 Ladner et al.

FOREIGN PATENT DOCUMENTS

JP       10295380       11/1998
WO    WO 00/00601    *  6/2000

OTHER PUBLICATIONS

Lazar et al. Molecular and Cellular Biology, Mar. 1988, vol. 8, No. 3, pp. 1247-1252.*
Broun et al. Science, Nov. 13, 1998, vol. 282, pp. 1315-1317.*
ed. Satoh K., Murata N., Stress Responses of Photosynthesis Organisms, pp. 115-131, Elsvier Science, Amsterdam.
Molecular Cloning, a Laboratory Manual, Second Edition, Cold Spring Harbor Laboratory Press, 1989 (front page and bibliographic information only).
Mitchell C. Tarczynski et al., "Stress Protection of Transgenic Tobacco by Production of the Osmolyte Mannitol", Science, vol. 259, Jan. 22, 1993.
P.B. Kavi Kishor et al., Overexpression of $\Delta^1$-Pyrroline-5-Carboxylate Synthetase Increases Proline Production and Confers osmotolerance in Transgenic Plants[1], Plant Physiol., 1995, 108, 1387-1394.
Hidenori Hayashi et al., "Transformation of *Arabidopis thaliana* with the codA gene for choline oxidase; accumulation of glycinebetaine and enhanced tolerance to salt and cold stress," The Plant Journal, 1997, 12. pp. 133-142.
Atsushi Sakamoto et al., "Metabolic engineering of rice leading to biosynthesis of glycinebetaine and tolerance to salt and cold", Plant Molecular Biology, 38, pp. 1011-1019, 1998.
Gynheung An High Efficiency Transformation of Cultured Tobacco Cells[1], Plant Physiol, 1985, 79, pp. 568-570.
Tetsuro Mimura et al., Efficient Callus Initiation from Leaf of Mangrove Plant, *Bruguiera sexangula* in Amino Acid Medium: Effect of NaCI on Callus Initiation, J. Plant Res., vol. 110, No. 1097, 1997, pp. 25-29.
Tetsuro Mimura et al., "NaCI-Dependent Growth, Ion Content and Regenaration of Calluses Initiated from the Mangrove Plant, *Bruguiera sexangula*", J. Plant Res., 110, pp. 31-36, 1997.
Elena Sheveleva et al., "Increased Salt and Drought Tolerance by D-Ononitol Production in Transgenic *Nicotiana tabacum* L.[1]", Plant Physiol., 1997, 115, pp. 1211-1219.
"Expression of a Late Embryogenesis Abundant Protein Gene, HVA1, from Barley Confers Tolerance to Water Deficit and Salt Stress in Transgenic Rice[1]", Plant Physiol., 1996, 110, pp. 249-257.
David W. Leung et al., "A Method For Random Mutagenesis Of A Defined DNA Segment Using A Modified Polymerase Chain Reaction", A Journal of Methods In Cell And Molecular Biology, vol. 1, No. 1, Aug. 1989, pp. 11-15.
Denise Muhlrad et al., "A Rapid Method for Localized Mutagenesis of Yeast Genes", Yeast vol. 8, pp. 79-82, 1992.
Willem P.C. Stemmer, "DNA shuffling by random fragmentation and reasssembly: In vitro recombination for molecular evolution", Proc. Natl. Acad. Sci. USA, vol. 91, pp. 10747-10751, Oct. 1994.

(Continued)

*Primary Examiner*—Medina A. Ibrahim
(74) *Attorney, Agent, or Firm*—Ann S. Hobbs; Venable LLP; Robert Kinberg

(57) ABSTRACT

The present invention relates to isolated DNA sequences from halophytes encoding proteins for improving tolerance to environmental stresses in plants. The invention also relates to vectors comprising the polynucleotides, and transformed host cells, and plants with improved environmental stress tolerance.

13 Claims, 8 Drawing Sheets

OTHER PUBLICATIONS

James A. Ostrem et al., "Salt Stress Increases the Level of Translatable mRNA for Phosphoenolpyruvate Carboxylase in *Mesembryanthemum crystallinum*[1]", Plant Physiol. 1987, 84, pp. 1270-1275.

Greene Publishing Associates and Wiley-Interscience, "Current Protocols In Molecular Biology", 1987.

"Continuous cultures of fused cells secreting antibody of predefined specificity", Nature vol. 256, pp. 495-497, Aug. 7, 1975.

Danuta Kozbor et al., "The production of monoclonal antibodies from human lymphocytes", Immunology Today, vol. 4, No. 3, 1983.

S.P.C. Cole, "Monoclonal Antibodies and Cancer Therapy", pp. 77-96, 1985.

Hiroshi Nojima, "Idenshi Library no Sakuseihoo" (Methods of preparing gene library), ed., Yoodo-sha, 1994.

Shokubutu saiboo koogaku nyumon (Introduction to plant cell engineering), Japan Scientific Societies Press, 1998.

Yukoh Hiei et al., "Efficient transformation of rice (*Oryza sativa* L.) mediated by Agrobacterium and sequence analysis of the boundaries of the T-DNA", The Plant Journal, 6(2), pp. 271-282, 1994.

"Model shokubuto no jikken protocol" (Experimental Protocols for plant models), Shunjin-sha, 1996.

"Shokubutu soshiiki baiyoo no gijutu" (Technologies for culturing plant tissues), Asakura-shoten, 1983.

Richard A. Jefferson, "GUS fusions: β-glucuronidase as a sensitive and versatile gene fusion marker in higher plants", The EMBO Journal, vol. 6, No. 13, pp. 3901-3907, 1987.

\* cited by examiner

A

B

FIG. 9 comparison of the sequence of bases

```
mangrin core  1 ATGAAGGTGGTCGGCCCTGCAAGATCAAAGAGTGCTACTGTACCCACCCAAACAGTATTG  60
C-52          1 ATGAAGGTGGTCGGCCCTGCAAGATCAAAGAGTGCTACTGTACCCACCCAAACAGTATTG  60
C-80          1 ATGAAGGTGGTCGGCCCTGCAAGATCAAAGAGTGCTACTGTACCCACCCAAACAGTATTG  60 mangrin core 61 CCTTTCAAGTTCACAAACCCGTCGTTACTCACTCGATCGCTAAGCTTTTCATCAAAAGGT 120
C-52         61 CCTTTCAAGTTCACAAACCCGTCGTTACTCACTCGATCGCTAAGCTTTTCATCAAAAGGT 120
C-80         61 CCTTTCAAGTTCGCAAACCCGTCGTTACTCACTCGATCGCTAAGCTTTTCATCAAAAGGT 120 mangrin core 121 TCAAGCTTTGACAGCTTCTCTGTACCCAAAAGATCTTTTTCTTGCAGAAGCCAAGCCACT 180
C-52         121 TCAAGCTTTGACAGCTTCTCTGTACCCAAAAGATCTTTTTCTTGCAGAAGCCAAGCCACC 180
C-80         121 TCAAGCTTTGACAGCTTCTCTGTACCCAAAAGATCTTTTTCTTGCAGAAGCCAAGCCACT 180 mangrin core 181 CCATCTGATGATGCCTCAAGACCCACCAAAGTTCAAGAGCTGTAA 225
C-52         181 CCATCTGATGATGCCTCAAGACCCACCAAAGTTCAAGAGCTGTAA 225
C-80         181 CCATCTGATGATGCCTCAAGACCCACCAAAGTTCAAGAGCTGTAA 225
``` comparison of the sequences of amino acids

```
mangrin core  1 MKVVGPARSKSATVPTQTVLPFKFTNPSLLTRSLSFSSKGSSFDSFSVPKRSFSCRSQAT 60
C-52          1 MKVVGPARSKSATVPTQTVLPFKFTNPSLLTRSLSFSSKGSSFDSFSVPKRSFSCRSQAT 60
C-80          1 MKVVGPARSKSATVPTQTVLPFKFANPSLLTRSLSFSSKGSSFDSFSVPKRSFSCRSQAT 60 mangrin core 61 PSDDASRPTKVQEL 74
C-52         61 PSDDASRPTKVQEL 74
C-80         61 PSDDASRPTKVQEL 74
```

FIG. 10 comparison of the functions of improvement of salt stress tolerance

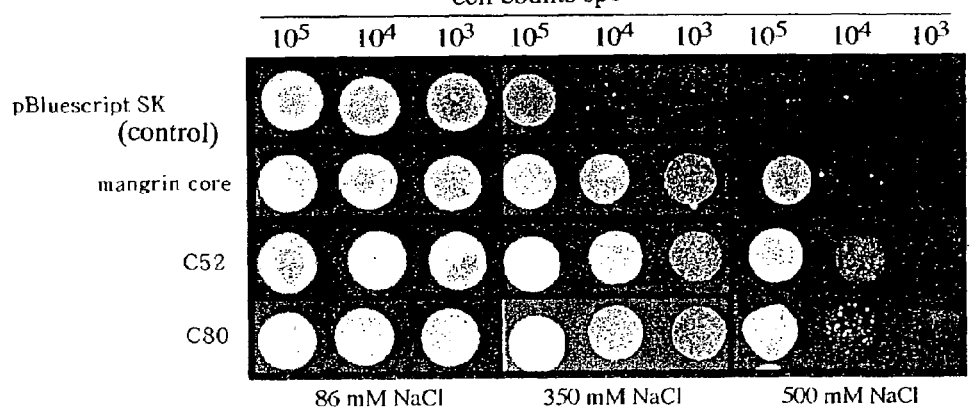

SEQUENCE LISTING

<160> NUMBER OF SEQ ID NOS: 72

<210> SEQ ID NO 1
<211> LENGTH: 1018
<212> TYPE: DNA
<213> ORGANISM: Bruguiera sexangula
<220> FEATURE:
<221> NAME/KEY: CDS
<222> LOCATION: (42)..(464)

<400> SEQUENCE: 1

```
gtccaaacag ccagagagaa acgacaacat cgaccaagaa a atg gct ctt tca agc        56
                                              Met Ala Leu Ser Ser
                                                1               5 tct gct ctg aga acc gtc tct tct tct gtg aag gtg gtc ggc cct gca        104
Ser Ala Leu Arg Thr Val Ser Ser Ser Val Lys Val Val Gly Pro Ala
               10                  15                  20 aga tca aag agt gct act gta ccc acc caa aca gta ttg cct ttc aag        152
Arg Ser Lys Ser Ala Thr Val Pro Thr Gln Thr Val Leu Pro Phe Lys
           25                  30                  35 ttc aca aac ccg tcg tta ctc act cga tcg cta agc ttt tca tca aaa        200
Phe Thr Asn Pro Ser Leu Leu Thr Arg Ser Leu Ser Phe Ser Ser Lys
       40                  45                  50 ggt tca agc ttt gac agc ttc tct gta ccc aaa aga tct ttt tct tgc        248
Gly Ser Ser Phe Asp Ser Phe Ser Val Pro Lys Arg Ser Phe Ser Cys
   55                  60                  65 aga agc caa gcc act cca tct gat gat gcc tca aga ccc acc aaa gtt        296
Arg Ser Gln Ala Thr Pro Ser Asp Asp Ala Ser Arg Pro Thr Lys Val
70                  75                  80                  85 caa gag ctg tgt gtg tat gag atg aac gag aga gat cgt gga agc cct        344
Gln Glu Leu Cys Val Tyr Glu Met Asn Glu Arg Asp Arg Gly Ser Pro
               90                  95                 100 gct gtt ctc cgg ttg agc cag aaa cct gtt aat tct ctc ggc gat ctc        392
Ala Val Leu Arg Leu Ser Gln Lys Pro Val Asn Ser Leu Gly Asp Leu
           105                 110                 115 gtg cct ttc agt aac aaa gtt tac agc gga gac ctg cag aag cga att        440
Val Pro Phe Ser Asn Lys Val Tyr Ser Gly Asp Leu Gln Lys Arg Ile
       120                 125                 130 gga gta acc gca gaa tat gca tcc tgatccaaaa caagccagaa aaaagggtg        494
Gly Val Thr Ala Glu Tyr Ala Ser
```

-continued

```
                135                 140
atcgctttga agcgatatat agctttattt tcggtggcta tggtcacatt gctgtgcaag    554
gcgcatactt gacctacgag gacacgcacc ttgctgtgac gggcgggtcg ggcatatttg    614
aaggagtgtc tggtcaggtt aagctgcagc aactcgtgta ccctttcaag ctcttctaca    674
ctttctactt gcgaggcatc aaggacttgc cggaggagct tacgaagaag ccggttgagc    734
cccacccttc tgttgagccg atgccggcgg ccaaggcttg cgagccacat gccgttgttg    794
ctaatttcac cgattagtga ttaattgtcc ttttggggtt cggatgaact tgagttagct    854
tacagttgca aacgttatg gcgcgagaca cgagagggaa ccttagccat aagaaaatta    914
ataatctcac ggtgctttta ttttgattct tctattagtt gaatcgttaa tgaaagtgga    974
ccaaattggc tgttttacgt tttaaaaaaa aaaaaaaaa aaaa                     1018
```

<210> SEQ ID NO 2
<211> LENGTH: 141
<212> TYPE: PRT
<213> ORGANISM: Bruguiera sexangula

<400> SEQUENCE: 2

```
Met Ala Leu Ser Ser Ser Ala Leu Arg Thr Val Ser Ser Val Lys
 1               5                  10                  15

Val Val Gly Pro Ala Arg Ser Lys Ser Ala Thr Val Pro Thr Gln Thr
            20                  25                  30

Val Leu Pro Phe Lys Phe Thr Asn Pro Ser Leu Leu Thr Arg Ser Leu
        35                  40                  45

Ser Phe Ser Ser Lys Gly Ser Ser Phe Asp Ser Phe Ser Val Pro Lys
    50                  55                  60

Arg Ser Phe Ser Cys Arg Ser Gln Ala Thr Pro Ser Asp Asp Ala Ser
65                  70                  75                  80

Arg Pro Thr Lys Val Gln Glu Leu Cys Val Tyr Glu Met Asn Glu Arg
                85                  90                  95

Asp Arg Gly Ser Pro Ala Val Leu Arg Leu Ser Gln Lys Pro Val Asn
            100                 105                 110

Ser Leu Gly Asp Leu Val Pro Phe Ser Asn Lys Val Tyr Ser Gly Asp
        115                 120                 125

Leu Gln Lys Arg Ile Gly Val Thr Ala Glu Tyr Ala Ser
    130                 135                 140
```

<210> SEQ ID NO 3
<211> LENGTH: 2060
<212> TYPE: DNA
<213> ORGANISM: Bruguiera sexangula
<220> FEATURE:
<221> NAME/KEY: CDS
<222> LOCATION: (81)..(1718)

<400> SEQUENCE: 3

```
cgaaattcct ctactaacaa taccagatcc agtctagcgt ttcgattttc tgcttcacat     60
ttctgtttct ttgaccagaa atg gca atc gcg gct caa act ccg gac att ctc    113
                      Met Ala Ile Ala Ala Gln Thr Pro Asp Ile Leu
                       1               5                  10 ggc gaa cgt cag tcc ggc cag gac gtc cgc act caa aat gtg gtg gca    161
Gly Glu Arg Gln Ser Gly Gln Asp Val Arg Thr Gln Asn Val Val Ala
            15                  20                  25 tgt caa gcg gtt gcc aat att gtc aaa tct tca ctt ggt cct gtc gga    209
Cys Gln Ala Val Ala Asn Ile Val Lys Ser Ser Leu Gly Pro Val Gly
    30                  35                  40
```

```
ctc gac aag atg cta gtg gat gat att ggt gat gta aca att aca aat      257
Leu Asp Lys Met Leu Val Asp Asp Ile Gly Asp Val Thr Ile Thr Asn
        45                  50                  55 gat ggt gct acg att ctt aag atg tta gaa gta gag cat cct gca gca      305
Asp Gly Ala Thr Ile Leu Lys Met Leu Glu Val Glu His Pro Ala Ala
 60                  65                  70                  75 aag gtg ctc gtg gag ttg gct gag ctt caa gac cga gaa gtt gga gat      353
Lys Val Leu Val Glu Leu Ala Glu Leu Gln Asp Arg Glu Val Gly Asp
                 80                  85                  90 gga acc act tcg gtt gtc atc ata gca gct gag ttg ctc aag aga gca      401
Gly Thr Thr Ser Val Val Ile Ile Ala Ala Glu Leu Leu Lys Arg Ala
                     95                 100                 105 aat gat ctc gtg agg aat aag atc cac cca aca tca ata atc agt gga      449
Asn Asp Leu Val Arg Asn Lys Ile His Pro Thr Ser Ile Ile Ser Gly
            110                 115                 120 tac agg ctt gct atg agg gaa gca tgc aag tat gtt gaa gag aaa ttg      497
Tyr Arg Leu Ala Met Arg Glu Ala Cys Lys Tyr Val Glu Glu Lys Leu
        125                 130                 135 tca atg aag gtt gaa aag ctt gga aaa gat tct cta gta aac tgt gca      545
Ser Met Lys Val Glu Lys Leu Gly Lys Asp Ser Leu Val Asn Cys Ala
140                 145                 150                 155 aag aca agc atg tcc tca aag ttg ata gct ggt gac agc gac ttc ttt      593
Lys Thr Ser Met Ser Ser Lys Leu Ile Ala Gly Asp Ser Asp Phe Phe
                160                 165                 170 gca aat ttg gtt gta gat gct gta caa gca gta aag atg acc aat gca      641
Ala Asn Leu Val Val Asp Ala Val Gln Ala Val Lys Met Thr Asn Ala
            175                 180                 185 cgg ggg gaa atc aaa tat cct atc aag agt ata aat att ttg aaa gct      689
Arg Gly Glu Ile Lys Tyr Pro Ile Lys Ser Ile Asn Ile Leu Lys Ala
        190                 195                 200 cat gga aaa agt gca aga gat agc tgc ctt ttg aat ggc tat gct ctc      737
His Gly Lys Ser Ala Arg Asp Ser Cys Leu Leu Asn Gly Tyr Ala Leu
    205                 210                 215 aat act ggt cgt gct gct caa ggg atg cct atg aga gtt gca cct gca      785
Asn Thr Gly Arg Ala Ala Gln Gly Met Pro Met Arg Val Ala Pro Ala
220                 225                 230                 235 agg att gct tgt ctt gac ttt aat ctt cag aaa acg aag atg caa ttg      833
Arg Ile Ala Cys Leu Asp Phe Asn Leu Gln Lys Thr Lys Met Gln Leu
                240                 245                 250 ggt gta caa gtc tta gtc act gat ccc agg gag ctt gaa aga att cgt      881
Gly Val Gln Val Leu Val Thr Asp Pro Arg Glu Leu Glu Arg Ile Arg
            255                 260                 265 caa aga gaa gct gat atg aca aag gaa cgg att gag aaa ctc ctg aaa      929
Gln Arg Glu Ala Asp Met Thr Lys Glu Arg Ile Glu Lys Leu Leu Lys
        270                 275                 280 gct gga gca aat gtt gtt cta acc aca aag gga att gat gac atg gca      977
Ala Gly Ala Asn Val Val Leu Thr Thr Lys Gly Ile Asp Asp Met Ala
285                 290                 295 ctt aaa tat ttt gtg gag gct ggg gct att gct gtg aga cgt gtt cgg     1025
Leu Lys Tyr Phe Val Glu Ala Gly Ala Ile Ala Val Arg Arg Val Arg
300                 305                 310                 315 aaa gag gat atg cgc cat gtt gcc aag gca act ggt gca aca ctg gtt     1073
Lys Glu Asp Met Arg His Val Ala Lys Ala Thr Gly Ala Thr Leu Val
                320                 325                 330 tca aca ttt gct gac atg gaa gga gag gaa aca ttt gat tca tca ctg     1121
Ser Thr Phe Ala Asp Met Glu Gly Glu Glu Thr Phe Asp Ser Ser Leu
            335                 340                 345 ctt gga caa gct gaa gaa gtt gtg gag gag cgc att gct gat gac gat     1169
Leu Gly Gln Ala Glu Glu Val Val Glu Glu Arg Ile Ala Asp Asp Asp
```

-continued

```
           350                 355                 360
gtg att atg ata aaa ggg aca aag act aca agt gcg gtt tcc ttg att    1217
Val Ile Met Ile Lys Gly Thr Lys Thr Thr Ser Ala Val Ser Leu Ile
365                 370                 375 ctt cgt ggt gca aat gac tat atg ctc gat gag atg gag cga gcc ctg    1265
Leu Arg Gly Ala Asn Asp Tyr Met Leu Asp Glu Met Glu Arg Ala Leu
380                 385                 390                 395 cat gat gct tta tgt att gtc aag aga acc ctt gaa tct aat aca gta    1313
His Asp Ala Leu Cys Ile Val Lys Arg Thr Leu Glu Ser Asn Thr Val
                400                 405                 410 gtt gca ggt gga ggt gct gtt gag gct gcc ttg tct gtg cac ttg gag    1361
Val Ala Gly Gly Gly Ala Val Glu Ala Ala Leu Ser Val His Leu Glu
            415                 420                 425 tac ctc gct aca act ctt ggg tca cga gag cag tta gca ata gca gag    1409
Tyr Leu Ala Thr Thr Leu Gly Ser Arg Glu Gln Leu Ala Ile Ala Glu
        430                 435                 440 ttt gca gaa tcc ttg ttg att ata cca aag gtt ctt gct gtc aat gct    1457
Phe Ala Glu Ser Leu Leu Ile Ile Pro Lys Val Leu Ala Val Asn Ala
445                 450                 455 gcc aaa gat gcc act gaa tta gct gca aaa ctc cgg gct tac cac cat    1505
Ala Lys Asp Ala Thr Glu Leu Ala Ala Lys Leu Arg Ala Tyr His His
460                 465                 470                 475 aca gca caa aca aag gct gat aag aaa cat tta tca agc atg gga cta    1553
Thr Ala Gln Thr Lys Ala Asp Lys Lys His Leu Ser Ser Met Gly Leu
                480                 485                 490 gac ctt tca aag ggg acc atc cga aac aac tta gaa gct gga gtc att    1601
Asp Leu Ser Lys Gly Thr Ile Arg Asn Asn Leu Glu Ala Gly Val Ile
            495                 500                 505 gaa cct gca atg agc aaa ata aag ata att cag ttt gct act gaa gca    1649
Glu Pro Ala Met Ser Lys Ile Lys Ile Ile Gln Phe Ala Thr Glu Ala
        510                 515                 520 gcc ata aca att ctt cga att gat gac atg atc aag ctt gtc aag gat    1697
Ala Ile Thr Ile Leu Arg Ile Asp Asp Met Ile Lys Leu Val Lys Asp
525                 530                 535 gag act cag aat gaa gag gaa tagatgcaga ctcttgtaag ctgcctccct       1748
Glu Thr Gln Asn Glu Glu Glu
540                 545 tttgttttca aatttgtgtc ccttgcgagc tggaggaaag gggggtgtt tatgtggtgt   1808 tttcagtggt tttaatttt caaggagctc gcggcctgtg tactttaggt tagagtccat   1868
ccaaggggtg tttattggat aatgcctaag ctgtttctcg tctattagta ggctggtagt  1928
tccactgagt tctcatccca attaaaagaa tgagatcaaa gggtcctaaa ttcgtactca  1988
ttggtgcacg atttgtttct gacaagcata agacttgacc ctctctatca caataaaaaa  2048
aaaaaaaaaa aa                                                     2060
```

<210> SEQ ID NO 4
<211> LENGTH: 546
<212> TYPE: PRT
<213> ORGANISM: Bruguiera sexangula

<400> SEQUENCE: 4

```
Met Ala Ile Ala Ala Gln Thr Pro Asp Ile Leu Gly Glu Arg Gln Ser
1               5                   10                  15

Gly Gln Asp Val Arg Thr Gln Asn Val Val Ala Cys Gln Ala Val Ala
            20                  25                  30

Asn Ile Val Lys Ser Ser Leu Gly Pro Val Gly Leu Asp Lys Met Leu
        35                  40                  45
```

-continued

```
Val Asp Asp Ile Gly Asp Val Thr Ile Thr Asn Asp Gly Ala Thr Ile
 50                  55                  60

Leu Lys Met Leu Glu Val Glu His Pro Ala Ala Lys Val Leu Val Glu
 65                  70                  75                  80

Leu Ala Glu Leu Gln Asp Arg Glu Val Gly Asp Gly Thr Thr Ser Val
                 85                  90                  95

Val Ile Ile Ala Ala Glu Leu Leu Lys Arg Ala Asn Asp Leu Val Arg
            100                 105                 110

Asn Lys Ile His Pro Thr Ser Ile Ile Ser Gly Tyr Arg Leu Ala Met
        115                 120                 125

Arg Glu Ala Cys Lys Tyr Val Glu Glu Lys Leu Ser Met Lys Val Glu
130                 135                 140

Lys Leu Gly Lys Asp Ser Leu Val Asn Cys Ala Lys Thr Ser Met Ser
145                 150                 155                 160

Ser Lys Leu Ile Ala Gly Asp Ser Asp Phe Phe Ala Asn Leu Val Val
                165                 170                 175

Asp Ala Val Gln Ala Val Lys Met Thr Asn Ala Arg Gly Glu Ile Lys
            180                 185                 190

Tyr Pro Ile Lys Ser Ile Asn Ile Leu Lys Ala His Gly Lys Ser Ala
        195                 200                 205

Arg Asp Ser Cys Leu Leu Asn Gly Tyr Ala Leu Asn Thr Gly Arg Ala
210                 215                 220

Ala Gln Gly Met Pro Met Arg Val Ala Pro Ala Arg Ile Ala Cys Leu
225                 230                 235                 240

Asp Phe Asn Leu Gln Lys Thr Lys Met Gln Leu Gly Val Gln Val Leu
                245                 250                 255

Val Thr Asp Pro Arg Glu Leu Glu Arg Ile Arg Gln Arg Glu Ala Asp
            260                 265                 270

Met Thr Lys Glu Arg Ile Glu Lys Leu Leu Lys Ala Gly Ala Asn Val
        275                 280                 285

Val Leu Thr Thr Lys Gly Ile Asp Asp Met Ala Leu Lys Tyr Phe Val
290                 295                 300

Glu Ala Gly Ala Ile Ala Val Arg Arg Val Arg Lys Glu Asp Met Arg
305                 310                 315                 320

His Val Ala Lys Ala Thr Gly Ala Thr Leu Val Ser Thr Phe Ala Asp
                325                 330                 335

Met Glu Gly Glu Glu Thr Phe Asp Ser Ser Leu Leu Gly Gln Ala Glu
            340                 345                 350

Glu Val Val Glu Glu Arg Ile Ala Asp Asp Val Ile Met Ile Lys
        355                 360                 365

Gly Thr Lys Thr Thr Ser Ala Val Ser Leu Ile Leu Arg Gly Ala Asn
370                 375                 380

Asp Tyr Met Leu Asp Glu Met Glu Arg Ala Leu His Asp Ala Leu Cys
385                 390                 395                 400

Ile Val Lys Arg Thr Leu Glu Ser Asn Thr Val Val Ala Gly Gly Gly
                405                 410                 415

Ala Val Glu Ala Ala Leu Ser Val His Leu Glu Tyr Leu Ala Thr Thr
            420                 425                 430

Leu Gly Ser Arg Glu Gln Leu Ala Ile Ala Glu Phe Ala Glu Ser Leu
        435                 440                 445

Leu Ile Ile Pro Lys Val Leu Ala Val Asn Ala Ala Lys Asp Ala Thr
450                 455                 460

Glu Leu Ala Ala Lys Leu Arg Ala Tyr His His Thr Ala Gln Thr Lys
```

-continued

```
                465                 470                 475                 480
Ala Asp Lys Lys His Leu Ser Ser Met Gly Leu Asp Leu Ser Lys Gly
                    485                 490                 495

Thr Ile Arg Asn Asn Leu Glu Ala Gly Val Ile Glu Pro Ala Met Ser
                500                 505                 510

Lys Ile Lys Ile Ile Gln Phe Ala Thr Glu Ala Ala Ile Thr Ile Leu
            515                 520                 525

Arg Ile Asp Asp Met Ile Lys Leu Val Lys Asp Glu Thr Gln Asn Glu
        530                 535                 540

Glu Glu
545

<210> SEQ ID NO 5
<211> LENGTH: 588
<212> TYPE: DNA
<213> ORGANISM: Bruguiera sexangula
<220> FEATURE:
<221> NAME/KEY: CDS
<222> LOCATION: (26)..(262)

<400> SEQUENCE: 5
gaaaaacaaa gcaatctcct gaagg atg tct tgc tgt ggt gga aac tgt ggc      52
                       Met Ser Cys Cys Gly Gly Asn Cys Gly
                         1               5 tgc gga gca agc tgc aat tgc ggc aac ggc tgt gga ggg tgc aag atg    100
Cys Gly Ala Ser Cys Asn Cys Gly Asn Gly Cys Gly Gly Cys Lys Met
 10                  15                  20                  25 tac cca gac atg ggc ttc gcc gag aag acc act acc gag act ctg gtt    148
Tyr Pro Asp Met Gly Phe Ala Glu Lys Thr Thr Thr Glu Thr Leu Val
                 30                  35                  40 ctc ggc gtg ggg cct gag agg gcc cac ttt gag gga gcc gag atg ggc    196
Leu Gly Val Gly Pro Glu Arg Ala His Phe Glu Gly Ala Glu Met Gly
             45                  50                  55 gtg ccg gcc gag aac gga ggc tgc aag tgc gga agt aac tgc acc tgc    244
Val Pro Ala Glu Asn Gly Gly Cys Lys Cys Gly Ser Asn Cys Thr Cys
         60                  65                  70 gac ccc tgc act tgt aaa tgagggaaa gtgacaggga aggtccgatc             292
Asp Pro Cys Thr Cys Lys
     75 tattattagt ctatatgtgt gtgttgggag tcttgcttac aataaaccag tcatgccttg   352 cgtttcctcc atgcgcagat cttaggtttt aggatatctc tgtggtttct ccaagctatg   412 gattttcagt gtctagtttt cctgtattac aaggatagtt tataaccgta tatgcatggt   472 cggaatcctt ccaaccattt cgtttgtcta aatatatata tgtgtgtgtg tgtgtgtgtt   532 tgatgggaaa gtgagcttct ttatgtttta tgactaaaaa aaaaaaaaaa aaaaaa       588

<210> SEQ ID NO 6
<211> LENGTH: 79
<212> TYPE: PRT
<213> ORGANISM: Bruguiera sexangula

<400> SEQUENCE: 6

Met Ser Cys Cys Gly Gly Asn Cys Gly Cys Gly Ala Ser Cys Asn Cys
  1               5                  10                  15

Gly Asn Gly Cys Gly Gly Cys Lys Met Tyr Pro Asp Met Gly Phe Ala
             20                  25                  30

Glu Lys Thr Thr Thr Glu Thr Leu Val Leu Gly Val Gly Pro Glu Arg
         35                  40                  45
```

```
Ala His Phe Glu Gly Ala Glu Met Gly Val Pro Ala Glu Asn Gly Gly
     50                  55                  60

Cys Lys Cys Gly Ser Asn Cys Thr Cys Asp Pro Cys Thr Cys Lys
 65                  70                  75

<210> SEQ ID NO 7
<211> LENGTH: 1280
<212> TYPE: DNA
<213> ORGANISM: Bruguiera sexangula
<220> FEATURE:
<221> NAME/KEY: CDS
<222> LOCATION: (1)..(1002)

<400> SEQUENCE: 7 att gaa ggg gaa gtg gtg gaa gtc caa att gat cgg ccg gcg gtg acc      48
Ile Glu Gly Glu Val Val Glu Val Gln Ile Asp Arg Pro Ala Val Thr
  1               5                  10                  15 ggc gcc gcg tcc aag acg ggg aaa ttg acg cta aag acg acg gag atg      96
Gly Ala Ala Ser Lys Thr Gly Lys Leu Thr Leu Lys Thr Thr Glu Met
             20                  25                  30 gag acg gtg tac gat ttg ggg gcg aaa atg ata gag gca ttg ggg aag     144
Glu Thr Val Tyr Asp Leu Gly Ala Lys Met Ile Glu Ala Leu Gly Lys
         35                  40                  45 gaa aag gtg cag agt ggg gat gtt att gca att gac aag gcg tcc ggc     192
Glu Lys Val Gln Ser Gly Asp Val Ile Ala Ile Asp Lys Ala Ser Gly
     50                  55                  60 aaa att aca aag ctt ggg cgt tca ttt tcg cgg tct agg gat tac gat     240
Lys Ile Thr Lys Leu Gly Arg Ser Phe Ser Arg Ser Arg Asp Tyr Asp
 65                  70                  75                  80 gcc atg gga cca cag gtg aag ttt gtt cag tgc cct gat ggg gag ctg     288
Ala Met Gly Pro Gln Val Lys Phe Val Gln Cys Pro Asp Gly Glu Leu
                 85                  90                  95 cag aag agg aaa gag gtc gtg cat tgt gtc tca ctg cac gag att gat     336
Gln Lys Arg Lys Glu Val Val His Cys Val Ser Leu His Glu Ile Asp
            100                 105                 110 gtt atc aat agc aga aca cag ggg ttt ctt gct ctt ttc acc ggg gat     384
Val Ile Asn Ser Arg Thr Gln Gly Phe Leu Ala Leu Phe Thr Gly Asp
        115                 120                 125 act ggt gaa atc cgt gcg gag gtg agg gaa caa att gac aca aag gtg     432
Thr Gly Glu Ile Arg Ala Glu Val Arg Glu Gln Ile Asp Thr Lys Val
    130                 135                 140 gct gaa tgg aga gag gaa ggg aaa gca gag att gtg cca ggt gtc ctc     480
Ala Glu Trp Arg Glu Glu Gly Lys Ala Glu Ile Val Pro Gly Val Leu
145                 150                 155                 160 ttt att gat gag gtc cac atg ctt gac att gag tgc ttc tca ttt ctg     528
Phe Ile Asp Glu Val His Met Leu Asp Ile Glu Cys Phe Ser Phe Leu
                165                 170                 175 aat cgt gct ctt gag aat gag atg gcg cca ata tta gtt gtt gct acc     576
Asn Arg Ala Leu Glu Asn Glu Met Ala Pro Ile Leu Val Val Ala Thr
            180                 185                 190 aac aga ggg atc acc aca atc aga ggc aca aat tac aaa tct cct cat     624
Asn Arg Gly Ile Thr Thr Ile Arg Gly Thr Asn Tyr Lys Ser Pro His
        195                 200                 205 ggg att cca ata gat ctc ctt gat cga cta ctc att atc aca act caa     672
Gly Ile Pro Ile Asp Leu Leu Asp Arg Leu Leu Ile Ile Thr Thr Gln
    210                 215                 220 cct tac aca aag gat gaa att cgt aag att ctg gat atc aga tgt cag     720
Pro Tyr Thr Lys Asp Glu Ile Arg Lys Ile Leu Asp Ile Arg Cys Gln
225                 230                 235                 240 gaa gaa gat gtg gag atg gct gaa gag gca aag gct ttg tta aca cat     768
Glu Glu Asp Val Glu Met Ala Glu Glu Ala Lys Ala Leu Leu Thr His
```

-continued

```
                    245                 250                 255
att ggg gca gaa aca tcc ttg aga tat gcc atc cat ctc att act gct    816
Ile Gly Ala Glu Thr Ser Leu Arg Tyr Ala Ile His Leu Ile Thr Ala
            260                 265                 270 gca gca ttg gca tgc cag aag cga aag gga aag ctt gtg gaa act gag    864
Ala Ala Leu Ala Cys Gln Lys Arg Lys Gly Lys Leu Val Glu Thr Glu
        275                 280                 285 gac att agt cga gct tac aat ctg ttt ctt gat gta aag aga tct aca    912
Asp Ile Ser Arg Ala Tyr Asn Leu Phe Leu Asp Val Lys Arg Ser Thr
    290                 295                 300 cag tac cta ata gag tat cag aat cag tac atg ttt aat gag gca ccg    960
Gln Tyr Leu Ile Glu Tyr Gln Asn Gln Tyr Met Phe Asn Glu Ala Pro
305                 310                 315                 320 gta gga gaa ggg gac gaa gaa ggg gcc aat gcc atg ctt tct            1002
Val Gly Glu Gly Asp Glu Glu Gly Ala Asn Ala Met Leu Ser
                325                 330 tgaagggcca taagctatgg agtctttgtg aaacccttct ccctacttta ttcgcagcac   1062
gagccctgaa atgaagaaca atggtagact tggatcccac cttggccctt atgtatgtct   1122
tctggaattg aaaaaagagt ccaagaaatt tgaatttcat gaaattggag aactgaactg   1182
tgcttactaa attgctactt tgcaagtaat gatagggcac tcacgcttga ctggctaagt   1242
atttatgttt ttatcatcaa aaaaaaaaaa aaaaaaaa                          1280
```

<210> SEQ ID NO 8
<211> LENGTH: 334
<212> TYPE: PRT
<213> ORGANISM: Bruguiera sexangula

<400> SEQUENCE: 8

```
Ile Glu Gly Glu Val Val Glu Val Gln Ile Asp Arg Pro Ala Val Thr
 1               5                  10                  15

Gly Ala Ala Ser Lys Thr Gly Lys Leu Thr Leu Lys Thr Thr Glu Met
            20                  25                  30

Glu Thr Val Tyr Asp Leu Gly Ala Lys Met Ile Glu Ala Leu Gly Lys
        35                  40                  45

Glu Lys Val Gln Ser Gly Asp Val Ile Ala Ile Asp Lys Ala Ser Gly
    50                  55                  60

Lys Ile Thr Lys Leu Gly Arg Ser Phe Ser Arg Ser Arg Asp Tyr Asp
 65                  70                  75                  80

Ala Met Gly Pro Gln Val Lys Phe Val Gln Cys Pro Asp Gly Glu Leu
                85                  90                  95

Gln Lys Arg Lys Glu Val Val His Cys Val Ser Leu His Glu Ile Asp
            100                 105                 110

Val Ile Asn Ser Arg Thr Gln Gly Phe Leu Ala Leu Phe Thr Gly Asp
        115                 120                 125

Thr Gly Glu Ile Arg Ala Glu Val Arg Glu Gln Ile Asp Thr Lys Val
    130                 135                 140

Ala Glu Trp Arg Glu Glu Gly Lys Ala Glu Ile Val Pro Gly Val Leu
145                 150                 155                 160

Phe Ile Asp Glu Val His Met Leu Asp Ile Glu Cys Phe Ser Phe Leu
                165                 170                 175

Asn Arg Ala Leu Glu Asn Glu Met Ala Pro Ile Leu Val Val Ala Thr
            180                 185                 190

Asn Arg Gly Ile Thr Thr Ile Arg Gly Thr Asn Tyr Lys Ser Pro His
        195                 200                 205
```

```
Gly Ile Pro Ile Asp Leu Leu Asp Arg Leu Leu Ile Ile Thr Thr Gln
    210                 215                 220
Pro Tyr Thr Lys Asp Glu Ile Arg Lys Ile Leu Asp Ile Arg Cys Gln
225                 230                 235                 240
Glu Glu Asp Val Glu Met Ala Glu Ala Lys Ala Leu Leu Thr His
                245                 250                 255
Ile Gly Ala Glu Thr Ser Leu Arg Tyr Ala Ile His Leu Ile Thr Ala
            260                 265                 270
Ala Ala Leu Ala Cys Gln Lys Arg Lys Gly Lys Leu Val Glu Thr Glu
        275                 280                 285
Asp Ile Ser Arg Ala Tyr Asn Leu Phe Leu Asp Val Lys Arg Ser Thr
    290                 295                 300
Gln Tyr Leu Ile Glu Tyr Gln Asn Gln Tyr Met Phe Asn Glu Ala Pro
305                 310                 315                 320
Val Gly Glu Gly Asp Glu Glu Gly Ala Asn Ala Met Leu Ser
                325                 330
```

<210> SEQ ID NO 9
<211> LENGTH: 420
<212> TYPE: DNA
<213> ORGANISM: Bruguiera sexangula
<220> FEATURE:
<221> NAME/KEY: CDS
<222> LOCATION: (27)..(194)

<400> SEQUENCE: 9

```
cgaaagtata aagtgatcgg cgagcg atg ggt cac tct aac gtc tgg aac tct      53
                             Met Gly His Ser Asn Val Trp Asn Ser
                              1               5 cac ccc aag aac tac ggc cct ggt tcc cgc gcc tgt cgg gtg tgt ggg     101
His Pro Lys Asn Tyr Gly Pro Gly Ser Arg Ala Cys Arg Val Cys Gly
 10                  15                  20                  25 aat ccg cac ggg ttg atc agg aag tac gga ctc atg tgc tgc aga cag    149
Asn Pro His Gly Leu Ile Arg Lys Tyr Gly Leu Met Cys Cys Arg Gln
             30                  35                  40 tgc ttc cgt agc aat gcc aag gaa att ggc ttc att aag tac cgc        194
Cys Phe Arg Ser Asn Ala Lys Glu Ile Gly Phe Ile Lys Tyr Arg
         45                  50                  55 tgaatgatat cgatatggcc cagaatggcc tgtggcggtg cgtgttcgat ttcagtagtt   254
cccctctttc ggatgagctt taggacaatg ttctctttag tttatgtatt gttgaacttg   314
gactgatgtt gaactaacga tattctggaa tcatttgata tttcgagagt ttattatttt   374
gatcatcatc ctcttgcttc tctgcttaaa aaaaaaaaa aaaaaa                    420
```

<210> SEQ ID NO 10
<211> LENGTH: 56
<212> TYPE: PRT
<213> ORGANISM: Bruguiera sexangula

<400> SEQUENCE: 10

```
Met Gly His Ser Asn Val Trp Asn Ser His Pro Lys Asn Tyr Gly Pro
 1               5                  10                  15

Gly Ser Arg Ala Cys Arg Val Cys Gly Asn Pro His Gly Leu Ile Arg
            20                  25                  30

Lys Tyr Gly Leu Met Cys Cys Arg Gln Cys Phe Arg Ser Asn Ala Lys
        35                  40                  45

Glu Ile Gly Phe Ile Lys Tyr Arg
    50                  55
```

-continued

```
<210> SEQ ID NO 11
<211> LENGTH: 1664
<212> TYPE: DNA
<213> ORGANISM: Bruguiera sexangula
<220> FEATURE:
<221> NAME/KEY: CDS
<222> LOCATION: (34)..(1380)

<400> SEQUENCE: 11
tctctcttta caggttaaag ctaagacttt ata atg ggt aag gag aag att cac         54
                                    Met Gly Lys Glu Lys Ile His
                                     1               5 att aac att gtg gtt att ggc cat gtc gac tcc gga aag tca acc aca        102
Ile Asn Ile Val Val Ile Gly His Val Asp Ser Gly Lys Ser Thr Thr
         10                  15                  20 act ggc cac ttg att tac aag ctt gga ggt atc gac aag cgt gtg att        150
Thr Gly His Leu Ile Tyr Lys Leu Gly Gly Ile Asp Lys Arg Val Ile
 25                  30                  35 gag agg ttt gag aag gaa gct gct gag atg aac aag agg tca ttc aag        198
Glu Arg Phe Glu Lys Glu Ala Ala Glu Met Asn Lys Arg Ser Phe Lys
 40                  45                  50                  55 tat gcc tgg gtg ctt gac aag ctg aag gct gag cgt gag cgt ggt atc        246
Tyr Ala Trp Val Leu Asp Lys Leu Lys Ala Glu Arg Glu Arg Gly Ile
                 60                  65                  70 acc att gat att gcc ttg tgg aag ttc gag aca acc aaa tat tac tgc        294
Thr Ile Asp Ile Ala Leu Trp Lys Phe Glu Thr Thr Lys Tyr Tyr Cys
             75                  80                  85 acg gtc att gat gct cct gga cat cgt gac ttt att aag aat atg atc        342
Thr Val Ile Asp Ala Pro Gly His Arg Asp Phe Ile Lys Asn Met Ile
         90                  95                 100 acc ggg act tcc caa gct gac tgt gct gtc ctc atc att gac tct acc        390
Thr Gly Thr Ser Gln Ala Asp Cys Ala Val Leu Ile Ile Asp Ser Thr
    105                 110                 115 act ggt ggc ttt gag gct ggt atc tct aaa gat ggt cag acc cgc gag        438
Thr Gly Gly Phe Glu Ala Gly Ile Ser Lys Asp Gly Gln Thr Arg Glu
120                 125                 130                 135 cat gcc ctg ctt gcc ttc acc ctt ggt gtt aag caa atg att tgc tgc        486
His Ala Leu Leu Ala Phe Thr Leu Gly Val Lys Gln Met Ile Cys Cys
                140                 145                 150 tgc aac aag atg gat gct acc act tcc aag tat tct aag gca aga tat        534
Cys Asn Lys Met Asp Ala Thr Thr Ser Lys Tyr Ser Lys Ala Arg Tyr
            155                 160                 165 gat gaa att gtt aag gaa gtg tca tcc tac ttg aag aag gtt ggt tac        582
Asp Glu Ile Val Lys Glu Val Ser Ser Tyr Leu Lys Lys Val Gly Tyr
        170                 175                 180 aac cca gag aag att cct ttt gtc ccc ata tct gga ttt gag ggt gac        630
Asn Pro Glu Lys Ile Pro Phe Val Pro Ile Ser Gly Phe Glu Gly Asp
    185                 190                 195 aac atg att gag aga tcc acc aac ctt gac tgg tac aag ggc cca act        678
Asn Met Ile Glu Arg Ser Thr Asn Leu Asp Trp Tyr Lys Gly Pro Thr
200                 205                 210                 215 ctt ctt gag gcc ctg gac atg atc cag gag cca aag agg cca tca gat        726
Leu Leu Glu Ala Leu Asp Met Ile Gln Glu Pro Lys Arg Pro Ser Asp
                220                 225                 230 aag ccc ctc cgt ctc cca ctt cag gat gtg tac aag att ggt ggt att        774
Lys Pro Leu Arg Leu Pro Leu Gln Asp Val Tyr Lys Ile Gly Gly Ile
            235                 240                 245 ggg aca gtc cca gtg ggt cgt gtt gaa act ggt gtc ctg aag cct gga        822
Gly Thr Val Pro Val Gly Arg Val Glu Thr Gly Val Leu Lys Pro Gly
        250                 255                 260
```

| | | |
|---|---|---|
| atg gtt gtt act ttt ggt ccc tca gga ctg acc act gaa gtt aag tct<br>Met Val Val Thr Phe Gly Pro Ser Gly Leu Thr Thr Glu Val Lys Ser<br>265                     270                   275 | 870 |
| gtg gag atg cac cat gaa gct ctc caa gag gct ctt ccc gga gac aac<br>Val Glu Met His His Glu Ala Leu Gln Glu Ala Leu Pro Gly Asp Asn<br>280               285                 290               295 | 918 |
| gtt ggc ttc aat gtt aag aat gtt tcc gtg aag gat ctt aag cgg ggt<br>Val Gly Phe Asn Val Lys Asn Val Ser Val Lys Asp Leu Lys Arg Gly<br>               300                   305               310 | 966 |
| tat gtt gcc tca aac tcc aag gat gat cct gcc aag gag gca tct agc<br>Tyr Val Ala Ser Asn Ser Lys Asp Asp Pro Ala Lys Glu Ala Ser Ser<br>               315                   320               325 | 1014 |
| ttc acc tcc caa gtt atc atc atg aac cac cct ggt cag att gga aat<br>Phe Thr Ser Gln Val Ile Ile Met Asn His Pro Gly Gln Ile Gly Asn<br>330                     335                 340 | 1062 |
| ggt tat gcc cct gtt ctg gat tgc cac acc tct cac att gct gtc aag<br>Gly Tyr Ala Pro Val Leu Asp Cys His Thr Ser His Ile Ala Val Lys<br>345                     350                 355 | 1110 |
| ttt tct gag atc ctc aca aag att gat agg cga tct ggc aag gag ctt<br>Phe Ser Glu Ile Leu Thr Lys Ile Asp Arg Arg Ser Gly Lys Glu Leu<br>360                     365                 370               375 | 1158 |
| gaa aag gag ccc aag ttc ttg aag aat ggt gat gct ggg ttc gtg aag<br>Glu Lys Glu Pro Lys Phe Leu Lys Asn Gly Asp Ala Gly Phe Val Lys<br>               380                   385               390 | 1206 |
| atg att ccg acc aag cct atg gtg gtg gaa act ttc tcc gag tat cct<br>Met Ile Pro Thr Lys Pro Met Val Val Glu Thr Phe Ser Glu Tyr Pro<br>               395                   400               405 | 1254 |
| ccg ctt ggt aga ttt gcc gtc agg gac atg cgc cag act gtt gca gtg<br>Pro Leu Gly Arg Phe Ala Val Arg Asp Met Arg Gln Thr Val Ala Val<br>410                     415                 420 | 1302 |
| gga gtc atc aag agt gtc gag aaa aag gaa cct tct gga gct aag gtg<br>Gly Val Ile Lys Ser Val Glu Lys Lys Glu Pro Ser Gly Ala Lys Val<br>425                     430                 435 | 1350 |
| act aaa tct gct gcc aag aag ggt ggc aaa tgaaccgtgc aagtcagagt<br>Thr Lys Ser Ala Ala Lys Lys Gly Gly Lys<br>440                   445 | 1400 |
| tgatgtagat gaaggctatt ggaagaataa agactgggcc ctggttagcg gtctaattat | 1460 |
| tggatgttca gcagttggtt tcgagaacta cagtttcaat tcagcgccat catcacggag | 1520 |
| ctgttgttcc cagaattggg ttcttgaccg tcggtggcat tggctgttgg tttgagtgac | 1580 |
| ttctttgtgt catgtttaga ctttatcgga tttgctattt cataaagcgg cttgggaatt | 1640 |
| ttaaaaaaaa aaaaaaaaaa aaaa | 1664 |

<210> SEQ ID NO 12
<211> LENGTH: 449
<212> TYPE: PRT
<213> ORGANISM: Bruguiera sexangula

<400> SEQUENCE: 12

Met Gly Lys Glu Lys Ile His Ile Asn Ile Val Val Ile Gly His Val
1                5                    10                   15

Asp Ser Gly Lys Ser Thr Thr Thr Gly His Leu Ile Tyr Lys Leu Gly
               20                   25               30

Gly Ile Asp Lys Arg Val Ile Glu Arg Phe Glu Lys Glu Ala Ala Glu
                  35                   40               45

Met Asn Lys Arg Ser Phe Lys Tyr Ala Trp Val Leu Asp Lys Leu Lys
50                     55                   60

Ala Glu Arg Glu Arg Gly Ile Thr Ile Asp Ile Ala Leu Trp Lys Phe

```
                65                  70                  75                  80
Glu Thr Thr Lys Tyr Tyr Cys Thr Val Ile Asp Ala Pro Gly His Arg
                    85                  90                  95
Asp Phe Ile Lys Asn Met Ile Thr Gly Thr Ser Gln Ala Asp Cys Ala
                100                 105                 110
Val Leu Ile Ile Asp Ser Thr Thr Gly Gly Phe Glu Ala Gly Ile Ser
                115                 120                 125
Lys Asp Gly Gln Thr Arg Glu His Ala Leu Leu Ala Phe Thr Leu Gly
            130                 135                 140
Val Lys Gln Met Ile Cys Cys Asn Lys Met Asp Ala Thr Thr Ser
145                 150                 155                 160
Lys Tyr Ser Lys Ala Arg Tyr Asp Glu Ile Val Lys Glu Val Ser Ser
                165                 170                 175
Tyr Leu Lys Lys Val Gly Tyr Asn Pro Glu Lys Ile Pro Phe Val Pro
                180                 185                 190
Ile Ser Gly Phe Glu Gly Asp Asn Met Ile Glu Arg Ser Thr Asn Leu
                195                 200                 205
Asp Trp Tyr Lys Gly Pro Thr Leu Leu Glu Ala Leu Asp Met Ile Gln
            210                 215                 220
Glu Pro Lys Arg Pro Ser Asp Lys Pro Leu Arg Leu Pro Leu Gln Asp
225                 230                 235                 240
Val Tyr Lys Ile Gly Gly Ile Gly Thr Val Pro Val Gly Arg Val Glu
                245                 250                 255
Thr Gly Val Leu Lys Pro Gly Met Val Val Thr Phe Gly Pro Ser Gly
                260                 265                 270
Leu Thr Thr Glu Val Lys Ser Val Glu Met His His Glu Ala Leu Gln
            275                 280                 285
Glu Ala Leu Pro Gly Asp Asn Val Gly Phe Asn Val Lys Asn Val Ser
            290                 295                 300
Val Lys Asp Leu Lys Arg Gly Tyr Val Ala Ser Asn Ser Lys Asp Asp
305                 310                 315                 320
Pro Ala Lys Glu Ala Ser Ser Phe Thr Ser Gln Val Ile Ile Met Asn
                325                 330                 335
His Pro Gly Gln Ile Gly Asn Gly Tyr Ala Pro Val Leu Asp Cys His
            340                 345                 350
Thr Ser His Ile Ala Val Lys Phe Ser Glu Ile Leu Thr Lys Ile Asp
            355                 360                 365
Arg Arg Ser Gly Lys Glu Leu Glu Lys Glu Pro Lys Phe Leu Lys Asn
            370                 375                 380
Gly Asp Ala Gly Phe Val Lys Met Ile Pro Thr Lys Pro Met Val Val
385                 390                 395                 400
Glu Thr Phe Ser Glu Tyr Pro Pro Leu Gly Arg Phe Ala Val Arg Asp
                405                 410                 415
Met Arg Gln Thr Val Ala Val Gly Val Ile Lys Ser Val Glu Lys Lys
                420                 425                 430
Glu Pro Ser Gly Ala Lys Val Thr Lys Ser Ala Ala Lys Lys Gly Gly
            435                 440                 445
Lys

<210> SEQ ID NO 13
<211> LENGTH: 770
<212> TYPE: DNA
<213> ORGANISM: Bruguiera sexangula
<220> FEATURE:
```

-continued

```
<221> NAME/KEY: CDS
<222> LOCATION: (2)..(769)

<400> SEQUENCE: 13 c gat gat atg gac gag gcc aca ccc acc ttt gtt tgg ggc acc aat atc        49
  Asp Asp Met Asp Glu Ala Thr Pro Thr Phe Val Trp Gly Thr Asn Ile
  1               5                   10                  15 agc gtg cag gat gtc aag gcc gct att cag atg ttt ttg aag cac ttc          97
Ser Val Gln Asp Val Lys Ala Ala Ile Gln Met Phe Leu Lys His Phe
            20                  25                  30 agg gat agt aat cag agt caa agg aac gag att ttt gaa gaa ggg aag         145
Arg Asp Ser Asn Gln Ser Gln Arg Asn Glu Ile Phe Glu Glu Gly Lys
        35                  40                  45 tac gtg aaa gcg ata cat aag gtt ctt gaa gtt gaa gga gag tcg ctt         193
Tyr Val Lys Ala Ile His Lys Val Leu Glu Val Glu Gly Glu Ser Leu
    50                  55                  60 gat gtt gat gct cgt gat gtg ttt gat tat gat tct gat ttg tat gcc         241
Asp Val Asp Ala Arg Asp Val Phe Asp Tyr Asp Ser Asp Leu Tyr Ala
65                  70                  75                  80 aag atg att cgg tac cca ctt gag gtt ttg gcc att ttc gac att gtt         289
Lys Met Ile Arg Tyr Pro Leu Glu Val Leu Ala Ile Phe Asp Ile Val
                85                  90                  95 ttg atg gat att gtg agt ttg atc aac cct ttg ttt gag aaa cat gta         337
Leu Met Asp Ile Val Ser Leu Ile Asn Pro Leu Phe Glu Lys His Val
            100                 105                 110 caa gtc agg att ttc aat ctt aag acc tcg att aca atg aga aat ctc         385
Gln Val Arg Ile Phe Asn Leu Lys Thr Ser Ile Thr Met Arg Asn Leu
        115                 120                 125 aac cct tct gat atc gaa aag atg gtg tca ttg aag gga atg ata att         433
Asn Pro Ser Asp Ile Glu Lys Met Val Ser Leu Lys Gly Met Ile Ile
    130                 135                 140 cgg tgt agt tcc ata ata ccg gag atc agg gaa gca gta ttt aga tgc         481
Arg Cys Ser Ser Ile Ile Pro Glu Ile Arg Glu Ala Val Phe Arg Cys
145                 150                 155                 160 ctt gtt tgt ggc tac ttc tct gat ccc atc gtt gtg gat aga gga cgg         529
Leu Val Cys Gly Tyr Phe Ser Asp Pro Ile Val Val Asp Arg Gly Arg
                165                 170                 175 ata agt gaa cct aaa gca tgc ttg aaa gag gaa tgt ctt act aag aac         577
Ile Ser Glu Pro Lys Ala Cys Leu Lys Glu Glu Cys Leu Thr Lys Asn
            180                 185                 190 tcc atg aca cta gtt cac aat cgt tgc agg ttt gct gat aag cag att         625
Ser Met Thr Leu Val His Asn Arg Cys Arg Phe Ala Asp Lys Gln Ile
        195                 200                 205 gtg agg ctc cag gag aca cct gac gag atc cct gaa gga gga aca cca         673
Val Arg Leu Gln Glu Thr Pro Asp Glu Ile Pro Glu Gly Gly Thr Pro
    210                 215                 220 cac acg gtg agc tta ttg atg cat gac aag ctg gta gat gct gga aag         721
His Thr Val Ser Leu Leu Met His Asp Lys Leu Val Asp Ala Gly Lys
225                 230                 235                 240 cca ggt gac agg gtt gag gtc act gga att tat agg gct atg agt gtt a       770
Pro Gly Asp Arg Val Glu Val Thr Gly Ile Tyr Arg Ala Met Ser Val
                245                 250                 255

<210> SEQ ID NO 14
<211> LENGTH: 256
<212> TYPE: PRT
<213> ORGANISM: Bruguiera sexangula

<400> SEQUENCE: 14

Asp Asp Met Asp Glu Ala Thr Pro Thr Phe Val Trp Gly Thr Asn Ile
1               5                   10                  15
```

-continued

```
Ser Val Gln Asp Val Lys Ala Ala Ile Gln Met Phe Leu Lys His Phe
         20                  25                  30
Arg Asp Ser Asn Gln Ser Gln Arg Asn Glu Ile Phe Glu Glu Gly Lys
     35                  40                  45
Tyr Val Lys Ala Ile His Lys Val Leu Glu Val Glu Gly Glu Ser Leu
 50                  55                  60
Asp Val Asp Ala Arg Asp Val Phe Asp Tyr Asp Ser Asp Leu Tyr Ala
 65                  70                  75                  80
Lys Met Ile Arg Tyr Pro Leu Glu Val Leu Ala Ile Phe Asp Ile Val
                 85                  90                  95
Leu Met Asp Ile Val Ser Leu Ile Asn Pro Leu Phe Glu Lys His Val
             100                 105                 110
Gln Val Arg Ile Phe Asn Leu Lys Thr Ser Ile Thr Met Arg Asn Leu
         115                 120                 125
Asn Pro Ser Asp Ile Glu Lys Met Val Ser Leu Lys Gly Met Ile Ile
     130                 135                 140
Arg Cys Ser Ser Ile Ile Pro Glu Ile Arg Glu Ala Val Phe Arg Cys
145                 150                 155                 160
Leu Val Cys Gly Tyr Phe Ser Asp Pro Ile Val Asp Arg Gly Arg
                 165                 170                 175
Ile Ser Glu Pro Lys Ala Cys Leu Lys Glu Cys Leu Thr Lys Asn
             180                 185                 190
Ser Met Thr Leu Val His Asn Arg Cys Arg Phe Ala Asp Lys Gln Ile
         195                 200                 205
Val Arg Leu Gln Glu Thr Pro Asp Glu Ile Pro Glu Gly Gly Thr Pro
     210                 215                 220
His Thr Val Ser Leu Leu Met His Asp Lys Leu Val Asp Ala Gly Lys
225                 230                 235                 240
Pro Gly Asp Arg Val Glu Val Thr Gly Ile Tyr Arg Ala Met Ser Val
                 245                 250                 255

<210> SEQ ID NO 15
<211> LENGTH: 846
<212> TYPE: DNA
<213> ORGANISM: Mesembryanthemum crystallinum
<220> FEATURE:
<221> NAME/KEY: CDS
<222> LOCATION: (39)..(530)

<400> SEQUENCE: 15
caaattttct ttgctgaatc gaatctacaa aatacctg atg ggt cag gtt ctt gac      56
                                          Met Gly Gln Val Leu Asp
                                           1               5 aaa ttt caa cgt aag caa tgg aga caa aag caa atc cag aag ata aca      104
Lys Phe Gln Arg Lys Gln Trp Arg Gln Lys Gln Ile Gln Lys Ile Thr
             10                  15                  20 gat aag gta ttt gat cgt gtc aaa agt ccg acc gga aat ggc act ctt      152
Asp Lys Val Phe Asp Arg Val Lys Ser Pro Thr Gly Asn Gly Thr Leu
         25                  30                  35 aca ttt gaa gag ctg tat ata gct acc ctg att gtc tac aat gat ata      200
Thr Phe Glu Glu Leu Tyr Ile Ala Thr Leu Ile Val Tyr Asn Asp Ile
     40                  45                  50 aac aag tat ttg ccg ggg ccg cac ttt gat cct cca tcg aaa gac aaa      248
Asn Lys Tyr Leu Pro Gly Pro His Phe Asp Pro Pro Ser Lys Asp Lys
 55                  60                  65                  70 atc aga gcc ttg atg cag gaa tgc gat atg gat gtc gat gga gaa ctt      296
Ile Arg Ala Leu Met Gln Glu Cys Asp Met Asp Val Asp Gly Glu Leu
```

-continued

```
                 75                  80                  85
aac cgt gag gaa ttt gtg aag ttc atg cag aag gtg aca gcc gat aca        344
Asn Arg Glu Glu Phe Val Lys Phe Met Gln Lys Val Thr Ala Asp Thr
             90                  95                 100 ttc tct acg gtc agc cag gga ctg att atc tct ctg att ctg gcg cca        392
Phe Ser Thr Val Ser Gln Gly Leu Ile Ile Ser Leu Ile Leu Ala Pro
        105                 110                 115 aca gtt gca ttg gcg acg aag agg gca aca gaa ggt gtt cca ggt gtg        440
Thr Val Ala Leu Ala Thr Lys Arg Ala Thr Glu Gly Val Pro Gly Val
    120                 125                 130 ggg aaa gtg gtg caa aag gtg cct act tca att tat gca tcc ctg gtg        488
Gly Lys Val Val Gln Lys Val Pro Thr Ser Ile Tyr Ala Ser Leu Val
135                 140                 145                 150 acc ctt gtt gtc gtt gca atc caa act gct agc gag gga tgc                530
Thr Leu Val Val Val Ala Ile Gln Thr Ala Ser Glu Gly Cys
                155                 160 tgattagagg ctttagttac ttgttcatga tacagaagga acagtcttgg tcaatttatt      590 tctttttta aggacataa ggaagttgta tatctttctt ctttcttcta ccaggttttg       650
ggggaagttg gaaagaacat acaaatgatt caactgcgt attggctgat cctcccattt      710
attaaaactt gtcgtgtcta gcatgagcga ttcaatattt gcaatatgca atatttgtaa     770
tgatgtctac attcagtgat tagtgtgatt gtgcagtttg ttgggaaaaa aaaaaaaaa      830 aaaaaaaaaa aaaaaa                                                      846
```

<210> SEQ ID NO 16
<211> LENGTH: 164
<212> TYPE: PRT
<213> ORGANISM: Mesembryanthemum crystallinum

<400> SEQUENCE: 16

```
Met Gly Gln Val Leu Asp Lys Phe Gln Arg Lys Gln Trp Arg Gln Lys
  1               5                  10                  15

Gln Ile Gln Lys Ile Thr Asp Lys Val Phe Asp Arg Val Lys Ser Pro
             20                  25                  30

Thr Gly Asn Gly Thr Leu Thr Phe Glu Glu Leu Tyr Ile Ala Thr Leu
         35                  40                  45

Ile Val Tyr Asn Asp Ile Asn Lys Tyr Leu Pro Gly Pro His Phe Asp
     50                  55                  60

Pro Pro Ser Lys Asp Lys Ile Arg Ala Leu Met Gln Glu Cys Asp Met
 65                  70                  75                  80

Asp Val Asp Gly Glu Leu Asn Arg Glu Glu Phe Val Lys Phe Met Gln
                 85                  90                  95

Lys Val Thr Ala Asp Thr Phe Ser Thr Val Ser Gln Gly Leu Ile Ile
            100                 105                 110

Ser Leu Ile Leu Ala Pro Thr Val Ala Leu Ala Thr Lys Arg Ala Thr
        115                 120                 125

Glu Gly Val Pro Gly Val Gly Lys Val Val Gln Lys Val Pro Thr Ser
    130                 135                 140

Ile Tyr Ala Ser Leu Val Thr Leu Val Val Val Ala Ile Gln Thr Ala
145                 150                 155                 160

Ser Glu Gly Cys
```

<210> SEQ ID NO 17
<211> LENGTH: 872
<212> TYPE: DNA
<213> ORGANISM: Mesembryanthemum crystallinum

```
<220> FEATURE:
<221> NAME/KEY: CDS
<222> LOCATION: (183)..(569)

<400> SEQUENCE: 17
aacaaaatgt ctctctcttt ctctttctct ttctctttct ctctcttcgt gggttgattg      60
agtaagctct gtccttttgc tctctgttga atgtactatc ttctgtgaac caaaggccaa     120
agattaacta ttggagattt ctctactcga aatttgtttt taggtgttga ccctgttgag     180 ct atg gcg aac aag ccc caa att cca acg aag aat tcg gcc ctc att        227
   Met Ala Asn Lys Pro Gln Ile Pro Thr Lys Asn Ser Ala Leu Ile
   1               5                  10                  15 gct att atc gcg gat gag gat act gta act gga ttt ttg ctg gct gga       275
Ala Ile Ile Ala Asp Glu Asp Thr Val Thr Gly Phe Leu Leu Ala Gly
             20                  25                  30 gtt ggt aat gtt gat cta cga aga cag aca aat tac att att gtg gac       323
Val Gly Asn Val Asp Leu Arg Arg Gln Thr Asn Tyr Ile Ile Val Asp
         35                  40                  45 aat aaa aca acg atg aag caa atc gaa gat gca ttc aag gag ttc aca       371
Asn Lys Thr Thr Met Lys Gln Ile Glu Asp Ala Phe Lys Glu Phe Thr
     50                  55                  60 gca aga gag gac att gcg gtt gta cta atc agc caa tat gtt gca aat       419
Ala Arg Glu Asp Ile Ala Val Val Leu Ile Ser Gln Tyr Val Ala Asn
 65                  70                  75 atg ata aga gta ttg gtt gat agc tac aac aaa cca atc ccg gca att       467
Met Ile Arg Val Leu Val Asp Ser Tyr Asn Lys Pro Ile Pro Ala Ile
 80                  85                  90                  95 ttg gag att cct tca aag gac cat cct tat gat cct aac cat gat tca       515
Leu Glu Ile Pro Ser Lys Asp His Pro Tyr Asp Pro Asn His Asp Ser
                 100                 105                 110 gtc ctt tca agg gtt aaa tac ctg ttc tct tct gaa tcg gca tca agc       563
Val Leu Ser Arg Val Lys Tyr Leu Phe Ser Ser Glu Ser Ala Ser Ser
             115                 120                 125 aga ttt tagccatatg ctttgtaaag ttccctgctc ctgaatgttt ggtgattatg        619
Arg Phe agtttaaact agaaccagtc acattctgac ttggtatttt gaggcactgt ttgttttatg     679
ttcttaaaat aaggagtgta attacgactc catgaatcgg gatatgactc catgaatcgc     739
atgtatttct ttccatctca tttgaaagag tcgagcagcc atatcattta gtttcttcct     799
cttgcgaatg agcttggaag aaatgttttg gctataaaag atttcaactc ttggtacaaa    859
aaaaaaaaaa aaa                                                        872

<210> SEQ ID NO 18
<211> LENGTH: 129
<212> TYPE: PRT
<213> ORGANISM: Mesembryanthemum crystallinum

<400> SEQUENCE: 18

Met Ala Asn Lys Pro Gln Ile Pro Thr Lys Asn Ser Ala Leu Ile Ala
1               5                  10                  15

Ile Ile Ala Asp Glu Asp Thr Val Thr Gly Phe Leu Leu Ala Gly Val
             20                  25                  30

Gly Asn Val Asp Leu Arg Arg Gln Thr Asn Tyr Ile Ile Val Asp Asn
         35                  40                  45

Lys Thr Thr Met Lys Gln Ile Glu Asp Ala Phe Lys Glu Phe Thr Ala
     50                  55                  60

Arg Glu Asp Ile Ala Val Val Leu Ile Ser Gln Tyr Val Ala Asn Met
 65                  70                  75                  80
```

```
Ile Arg Val Leu Val Asp Ser Tyr Asn Lys Pro Ile Pro Ala Ile Leu
                85                  90                  95

Glu Ile Pro Ser Lys Asp His Pro Tyr Asp Pro Asn His Asp Ser Val
            100                 105                 110

Leu Ser Arg Val Lys Tyr Leu Phe Ser Ser Glu Ser Ala Ser Ser Arg
        115                 120                 125
Phe

<210> SEQ ID NO 19
<211> LENGTH: 647
<212> TYPE: DNA
<213> ORGANISM: Mesembryanthemum crystallinum
<220> FEATURE:
<221> NAME/KEY: CDS
<222> LOCATION: (64)..(426)

<400> SEQUENCE: 19 cttgttttc tctctcctct ctctctctct tctccgcacc ctcaggcagt gaaggtagca    60 aca atg gcg tac gcg atg aag cca acg aag ccc ggg atg gag gaa tcc   108
    Met Ala Tyr Ala Met Lys Pro Thr Lys Pro Gly Met Glu Glu Ser
    1               5                   10                  15 cag gag cag att cac aag atc agg atc act ctt tct tct aag aac gtc   156
Gln Glu Gln Ile His Lys Ile Arg Ile Thr Leu Ser Ser Lys Asn Val
                20                  25                  30 aag aac ctt gag aaa gtg tgt gct gat ctt gta cgc ggt gca aag gac   204
Lys Asn Leu Glu Lys Val Cys Ala Asp Leu Val Arg Gly Ala Lys Asp
            35                  40                  45 aag cgc ctc agg gtt aag gga cca gtg agg atg ccc acc aag gtt ctg   252
Lys Arg Leu Arg Val Lys Gly Pro Val Arg Met Pro Thr Lys Val Leu
        50                  55                  60 aag atc aca aca agg aag tct ccc tgt ggt gaa gga acc aac acc ttt   300
Lys Ile Thr Thr Arg Lys Ser Pro Cys Gly Glu Gly Thr Asn Thr Phe
    65                  70                  75 gac aga ttt gag ttg cgt gtt cac aag aga gtc att gac ctc ttc agc   348
Asp Arg Phe Glu Leu Arg Val His Lys Arg Val Ile Asp Leu Phe Ser
80                  85                  90                  95 tcc cca gac gtg gtc aag cag atc acc tcc atc acc att gaa cct ggt   396
Ser Pro Asp Val Val Lys Gln Ile Thr Ser Ile Thr Ile Glu Pro Gly
                100                 105                 110 gtt gag gtt gag gtt aca ata gct gac tct tagacatgcc tgttgaagtt     446
Val Glu Val Glu Val Thr Ile Ala Asp Ser
            115                 120 gtcgtcgttg tagggctgtt gtagctgtct catatagtgg tgctatctca ctaagaattt   506
tgaagatact aaattgtttg tttgaaagag atgttttctt tagctgtaat gttatgtttt   566
tgaaggtgtt ggaacatgca ttatttgtta atgctttatc aatagaactt ccaatttgaa   626
tgcaaaaaaa aaaaaaaaaa a                                              647

<210> SEQ ID NO 20
<211> LENGTH: 121
<212> TYPE: PRT
<213> ORGANISM: Mesembryanthemum crystallinum

<400> SEQUENCE: 20

Met Ala Tyr Ala Met Lys Pro Thr Lys Pro Gly Met Glu Glu Ser Gln
1               5                   10                  15

Glu Gln Ile His Lys Ile Arg Ile Thr Leu Ser Ser Lys Asn Val Lys
            20                  25                  30
```

```
                    Asn Leu Glu Lys Val Cys Ala Asp Leu Val Arg Gly Ala Lys Asp Lys
                                 35                  40                  45

Arg Leu Arg Val Lys Gly Pro Val Arg Met Pro Thr Lys Val Leu Lys
                             50                  55                  60

Ile Thr Thr Arg Lys Ser Pro Cys Gly Glu Gly Thr Asn Thr Phe Asp
                     65                  70                  75                  80

Arg Phe Glu Leu Arg Val His Lys Arg Val Ile Asp Leu Phe Ser Ser
                                     85                  90                  95

Pro Asp Val Val Lys Gln Ile Thr Ser Ile Thr Ile Glu Pro Gly Val
                                100                 105                 110

Glu Val Glu Val Thr Ile Ala Asp Ser
                                115                 120

<210> SEQ ID NO 21
<211> LENGTH: 686
<212> TYPE: DNA
<213> ORGANISM: Sueada japonica
<220> FEATURE:
<221> NAME/KEY: CDS
<222> LOCATION: (62)..(493)

<400> SEQUENCE: 21
acaccattca caaaacacat taaaaaaaaa cactacttct ttctttctta gccacttgaa      60 a atg gcc tac tca aag gct gta ctc ctt gcc ctt atc ttt gct gtg act    109
  Met Ala Tyr Ser Lys Ala Val Leu Leu Ala Leu Ile Phe Ala Val Thr
    1               5                  10                  15 ctt gtc att gcc tct cag gtc tca gct cgt gaa ctt gct gag gag aca      157
Leu Val Ile Ala Ser Gln Val Ser Ala Arg Glu Leu Ala Glu Glu Thr
             20                  25                  30 caa tct gtg gag gag tct aag gga tac ggt ggt ggg cac gga ggt cac      205
Gln Ser Val Glu Glu Ser Lys Gly Tyr Gly Gly Gly His Gly Gly His
         35                  40                  45 tat ggt ggt ggt cac tat ggt ggt gga cac aga cac ggt ggc cat gga      253
Tyr Gly Gly Gly His Tyr Gly Gly Gly His Arg His Gly Gly His Gly
     50                  55                  60 cac tac gca act gag gaa gca gag aac aag aat gaa gcc gta gaa cct      301
His Tyr Ala Thr Glu Glu Ala Glu Asn Lys Asn Glu Ala Val Glu Pro
 65                  70                  75                  80 caa ggc ggc tat ggt cac gga cac gga gga ggc tac gga cac ggt ggt      349
Gln Gly Gly Tyr Gly His Gly His Gly Gly Gly Tyr Gly His Gly Gly
                 85                  90                  95 ggc tac gga cac ggt gga ggc tac gga cac gga ggt ggc tac ggg cac      397
Gly Tyr Gly His Gly Gly Gly Tyr Gly His Gly Gly Gly Tyr Gly His
            100                 105                 110 ggt ggt ggc tac gga cat gga ggt ggt tat gga cac ggt gga cac ggt      445
Gly Gly Gly Tyr Gly His Gly Gly Gly Tyr Gly His Gly Gly His Gly
        115                 120                 125 gga cat ggt ggt cat ggt cac tac gcc aag act acc gag gaa caa aat      493
Gly His Gly Gly His Gly His Tyr Ala Lys Thr Thr Glu Glu Gln Asn
    130                 135                 140 taagttatgg gttactaaaa cttaaattgt acgttgtcaa ataaaatgta ctttatgatt    553
ttacatgagt atgcatgtaa ttcatcataa gcttcaagga ctatcttgta ctctatgtta    613
tatacctata tgaaatggaa gcgtgacttt tattactgta aaaaaaaaaa aaaaaaaaa     673 aaaaaaaaaa aaa                                                       686

<210> SEQ ID NO 22
<211> LENGTH: 144
<212> TYPE: PRT
```

<213> ORGANISM: Sueada japonica

<400> SEQUENCE: 22

```
Met Ala Tyr Ser Lys Ala Val Leu Leu Ala Leu Ile Phe Ala Val Thr
 1               5                  10                  15

Leu Val Ile Ala Ser Gln Val Ser Ala Arg Glu Leu Ala Glu Glu Thr
             20                  25                  30

Gln Ser Val Glu Glu Ser Lys Gly Tyr Gly Gly His Gly Gly His
         35                  40                  45

Tyr Gly Gly Gly His Tyr Gly Gly Gly His Arg His Gly Gly His Gly
     50                  55                  60

His Tyr Ala Thr Glu Glu Ala Glu Asn Lys Asn Glu Ala Val Glu Pro
 65                  70                  75                  80

Gln Gly Gly Tyr Gly His Gly His Gly Gly Tyr Gly His Gly Gly
                 85                  90                  95

Gly Tyr Gly His Gly Gly Gly Tyr Gly His Gly Gly Gly Tyr Gly His
                100                 105                 110

Gly Gly Gly Tyr Gly His Gly Gly Gly Tyr Gly His Gly Gly His Gly
            115                 120                 125

Gly His Gly Gly His Gly His Tyr Ala Lys Thr Thr Glu Glu Gln Asn
        130                 135                 140
```

<210> SEQ ID NO 23
<211> LENGTH: 683
<212> TYPE: DNA
<213> ORGANISM: Salsola komarovii
<220> FEATURE:
<221> NAME/KEY: CDS
<222> LOCATION: (48)..(362)

<400> SEQUENCE: 23

```
gttaagatat tatattgcaa ctttacaaag catttctgca actaaat atg gcc ttt         56
                                                    Met Ala Phe
                                                      1 tcc aaa cct cta att gct tct cta ctt ctt tct ctc ttt gtt ctt cag        104
Ser Lys Pro Leu Ile Ala Ser Leu Leu Leu Ser Leu Phe Val Leu Gln
  5                  10                  15 ttt gtt cat gca gtt gaa cct att tca tcc tcc aat caa gtg ggt agc        152
Phe Val His Ala Val Glu Pro Ile Ser Ser Ser Asn Gln Val Gly Ser
     20                  25                  30                  35 aac act gga ggt acc tca gag agt aaa gtg gat tgt ggg gcg gca tgt        200
Asn Thr Gly Gly Thr Ser Glu Ser Lys Val Asp Cys Gly Ala Ala Cys
                 40                  45                  50 acg gtg agg tgc agc gcc tcg aag agg cca aac cta tgc aac agg tca        248
Thr Val Arg Cys Ser Ala Ser Lys Arg Pro Asn Leu Cys Asn Arg Ser
             55                  60                  65 tgt ggc agt tgt tgc aag acg tgc aac tgc gtg cca cca ggc act tcc        296
Cys Gly Ser Cys Cys Lys Thr Cys Asn Cys Val Pro Pro Gly Thr Ser
         70                  75                  80 ggc aac tac gaa gcc tgc cct tgt tac gcc aac ttg acc acc cac ggc        344
Gly Asn Tyr Glu Ala Cys Pro Cys Tyr Ala Asn Leu Thr Thr His Gly
     85                  90                  95 aat cga cac aag tgc cct taattaacaa gaattgttta gttgtttatt              392
Asn Arg His Lys Cys Pro
100                 105 acatccgtac catgtaacgt actcctattt acactactag agtactagta ataaacattt       452
ttaggcacgg tccagttgtt catgtagcta gtggtatatt gagtcataaa tgagtgattg       512
aaaatgagat atgataaaag tgtattatct acattgtagt actgttttgt atcatagtgt       572
```

```
agtgatgttt attttcgta cctttaattt gttactttgt attccctttc attctatcta       632
tttacaatcc ttttgtaagt ttatgtgaaa aaaaaaaaaa aaaaaaaaaa a               683

<210> SEQ ID NO 24
<211> LENGTH: 105
<212> TYPE: PRT
<213> ORGANISM: Salsola komarovii

<400> SEQUENCE: 24

Met Ala Phe Ser Lys Pro Leu Ile Ala Ser Leu Leu Ser Leu Phe
 1               5                  10                  15

Val Leu Gln Phe Val His Ala Val Glu Pro Ile Ser Ser Asn Gln
                20                  25                  30

Val Gly Ser Asn Thr Gly Thr Ser Glu Ser Lys Val Asp Cys Gly
            35                  40                  45

Ala Ala Cys Thr Val Arg Cys Ser Ala Ser Lys Arg Pro Asn Leu Cys
        50                  55                  60

Asn Arg Ser Cys Gly Ser Cys Cys Lys Thr Cys Asn Cys Val Pro Pro
 65                 70                  75                  80

Gly Thr Ser Gly Asn Tyr Glu Ala Cys Pro Cys Tyr Ala Asn Leu Thr
                85                  90                  95

Thr His Gly Asn Arg His Lys Cys Pro
                100                 105

<210> SEQ ID NO 25
<211> LENGTH: 803
<212> TYPE: DNA
<213> ORGANISM: Salsola komarovii
<220> FEATURE:
<221> NAME/KEY: CDS
<222> LOCATION: (51)..(593)

<400> SEQUENCE: 25
cgcagacgct tcagctcttt ctctctcttt ctctctcctc accgtgaaag atg ggg        56
                                                         Met Gly
                                                          1 ttg tca ttt acc aaa ttg ttt agc cgg ttg ttc gct aag aag gaa atg       104
Leu Ser Phe Thr Lys Leu Phe Ser Arg Leu Phe Ala Lys Lys Glu Met
      5                  10                  15 cgt atc ctt atg gtc ggt ctc gat gcc gct ggt aaa acc acc att ctc       152
Arg Ile Leu Met Val Gly Leu Asp Ala Ala Gly Lys Thr Thr Ile Leu
 20                  25                  30 tat aaa ctc aag ctg gga gag att gtc acc acc att cct acc att gga       200
Tyr Lys Leu Lys Leu Gly Glu Ile Val Thr Thr Ile Pro Thr Ile Gly
 35                  40                  45                  50 ttt aat gtg gag act gta gaa tac aag aac atc agc ttc act gtg tgg       248
Phe Asn Val Glu Thr Val Glu Tyr Lys Asn Ile Ser Phe Thr Val Trp
              55                  60                  65 gat gtc ggg ggt caa gac aag att cgt cca ttg tgg aga cat tac ttc       296
Asp Val Gly Gly Gln Asp Lys Ile Arg Pro Leu Trp Arg His Tyr Phe
          70                  75                  80 caa aac acc caa ggt ctc atc ttt gtg gtt gac agt aat gat cgt gac       344
Gln Asn Thr Gln Gly Leu Ile Phe Val Val Asp Ser Asn Asp Arg Asp
      85                  90                  95 cgt gtc gtt gag gca aga gat gaa ctg cat agg atg tta aat gag gat       392
Arg Val Val Glu Ala Arg Asp Glu Leu His Arg Met Leu Asn Glu Asp
 100                 105                 110 gaa tta cga gat gca gtg ttg ttg gtg ttt gca aac aag caa gat ctt       440
Glu Leu Arg Asp Ala Val Leu Leu Val Phe Ala Asn Lys Gln Asp Leu
```

```
                115                 120                 125                 130
ccc aat gca atg aat gct gct gag atc act gat aag ctt ggt ctc cat          488
Pro Asn Ala Met Asn Ala Ala Glu Ile Thr Asp Lys Leu Gly Leu His
                135                 140                 145 tct cta cgt caa cgc cat tgg tac ata caa agc aca tgt gcc acc tct          536
Ser Leu Arg Gln Arg His Trp Tyr Ile Gln Ser Thr Cys Ala Thr Ser
            150                 155                 160 gga gaa ggg ctt tac gag ggt ctg gac tgg ctc tca aac aat atc gct          584
Gly Glu Gly Leu Tyr Glu Gly Leu Asp Trp Leu Ser Asn Asn Ile Ala
        165                 170                 175 agc aag gct taaaagtaac agaacgagta aggttagctt tctcagagaa                  633
Ser Lys Ala
        180 gaagctggag tataggctga ggactatcgt tactgctagt gttaccctt tattttttgc         693 catttatatg ttcacatttt tggttcctat cggacaagaa ttattttctg cgtttatgtt        753 gacttgttat aataccatac tttttagttg aaaaaaaaaa aaaaaaaaaa                    803

<210> SEQ ID NO 26
<211> LENGTH: 181
<212> TYPE: PRT
<213> ORGANISM: Salsola komarovii

<400> SEQUENCE: 26

Met Gly Leu Ser Phe Thr Lys Leu Phe Ser Arg Leu Phe Ala Lys Lys
1               5                   10                  15

Glu Met Arg Ile Leu Met Val Gly Leu Asp Ala Ala Gly Lys Thr Thr
            20                  25                  30

Ile Leu Tyr Lys Leu Lys Leu Gly Glu Ile Val Thr Thr Ile Pro Thr
        35                  40                  45

Ile Gly Phe Asn Val Glu Thr Val Glu Tyr Lys Asn Ile Ser Phe Thr
    50                  55                  60

Val Trp Asp Val Gly Gly Gln Asp Lys Ile Arg Pro Leu Trp Arg His
65                  70                  75                  80

Tyr Phe Gln Asn Thr Gln Gly Leu Ile Phe Val Val Asp Ser Asn Asp
                85                  90                  95

Arg Asp Arg Val Val Glu Ala Arg Asp Glu Leu His Arg Met Leu Asn
            100                 105                 110

Glu Asp Glu Leu Arg Asp Ala Val Leu Leu Val Phe Ala Asn Lys Gln
        115                 120                 125

Asp Leu Pro Asn Ala Met Asn Ala Ala Glu Ile Thr Asp Lys Leu Gly
    130                 135                 140

Leu His Ser Leu Arg Gln Arg His Trp Tyr Ile Gln Ser Thr Cys Ala
145                 150                 155                 160

Thr Ser Gly Glu Gly Leu Tyr Glu Gly Leu Asp Trp Leu Ser Asn Asn
                165                 170                 175

Ile Ala Ser Lys Ala
            180

<210> SEQ ID NO 27
<211> LENGTH: 680
<212> TYPE: DNA
<213> ORGANISM: Avicennia marina
<220> FEATURE:
<221> NAME/KEY: CDS
<222> LOCATION: (161)..(454)

<400> SEQUENCE: 27
```

-continued

```
ctaaaagcca aagcaagat aagaaacagg ttcctttagc tatcttcctc gtctcgctgc        60
tgcaaaagtt ccatcccag aagatcagga aaacccttct gcagcagcac tctaataatc       120 ctccaattt gattcaagag aagaaacaaa ataaacagaa atg gct cgc tct ttc         175
                                            Met Ala Arg Ser Phe
                                              1               5 tcc aac gct aag acc gtc tct gct gtc att gcc aac gaa atc tca gct        223
Ser Asn Ala Lys Thr Val Ser Ala Val Ile Ala Asn Glu Ile Ser Ala
             10                  15                  20 ctt gtc acc agg agg ggt tat gct gct ctc gca cag ggc gtt gtt tcg        271
Leu Val Thr Arg Arg Gly Tyr Ala Ala Leu Ala Gln Gly Val Val Ser
         25                  30                  35 agc agc gcg aga agc ggc ggc gct ccg aac gtg atg ctg aag aaa gga        319
Ser Ser Ala Arg Ser Gly Gly Ala Pro Asn Val Met Leu Lys Lys Gly
     40                  45                  50 tcc gaa gaa tcc ggg aag aca gca tgg gtg ccc gac ccg gac acc ggc        367
Ser Glu Glu Ser Gly Lys Thr Ala Trp Val Pro Asp Pro Asp Thr Gly
 55                  60                  65 tac tac cga ccg gga aac gag gac aag gcc gcg ctg gac ccg gtc gag        415
Tyr Tyr Arg Pro Gly Asn Glu Asp Lys Ala Ala Leu Asp Pro Val Glu
 70                  75                  80                  85 ctg cgg gag atg ctc atc aag aac aag ccc agc cga caa tgaatgaacc        464
Leu Arg Glu Met Leu Ile Lys Asn Lys Pro Ser Arg Gln
             90                  95 aagaattgtg ggattctcat taattcctcc cctgttctgg tccatcgtcg gaatctgaac      524
ctgttgttcg tctagaaatt cgttcccatg gaaatctatc aaagtctgta ttcttgccat      584
ggctcttcct gtcccatata tgtatgtcct caggtgtggc ctggggtggt ttgatagata     644
tataaaatgt ggtgaattta aaaaaaaaaa aaaaaa                                680

<210> SEQ ID NO 28
<211> LENGTH: 98
<212> TYPE: PRT
<213> ORGANISM: Avicennia marina

<400> SEQUENCE: 28

Met Ala Arg Ser Phe Ser Asn Ala Lys Thr Val Ser Ala Val Ile Ala
  1               5                  10                  15

Asn Glu Ile Ser Ala Leu Val Thr Arg Arg Gly Tyr Ala Ala Leu Ala
             20                  25                  30

Gln Gly Val Val Ser Ser Ser Ala Arg Ser Gly Gly Ala Pro Asn Val
         35                  40                  45

Met Leu Lys Lys Gly Ser Glu Glu Ser Gly Lys Thr Ala Trp Val Pro
     50                  55                  60

Asp Pro Asp Thr Gly Tyr Tyr Arg Pro Gly Asn Glu Asp Lys Ala Ala
 65                  70                  75                  80

Leu Asp Pro Val Glu Leu Arg Glu Met Leu Ile Lys Asn Lys Pro Ser
                 85                  90                  95

Arg Gln

<210> SEQ ID NO 29
<211> LENGTH: 490
<212> TYPE: DNA
<213> ORGANISM: Avicennia marina
<220> FEATURE:
<221> NAME/KEY: CDS
<222> LOCATION: (20)..(349)

<400> SEQUENCE: 29
```

-continued

```
tcggctgggc aaagaaggg atg gcg att cca tcg gaa att cgg gac ttt att      52
              Met Ala Ile Pro Ser Glu Ile Arg Asp Phe Ile
                1               5                  10 gct agc cgc aac aga tct ttg gtg atc gca tct cca aag gaa gat gag     100
Ala Ser Arg Asn Arg Ser Leu Val Ile Ala Ser Pro Lys Glu Asp Glu
         15                  20                  25 aaa att ctc cgc tca agg cag tgc acc gaa gaa ggg gcg cgt gca gga     148
Lys Ile Leu Arg Ser Arg Gln Cys Thr Glu Glu Gly Ala Arg Ala Gly
     30                  35                  40 gcc aaa gct gct gca gtt gct tgc gtt gcc agc gcc att ccc act ctg     196
Ala Lys Ala Ala Ala Val Ala Cys Val Ala Ser Ala Ile Pro Thr Leu
 45                  50                  55 gta gct gtt cga acg att ccg tgg gca aag gca aac ctc aac tat aca     244
Val Ala Val Arg Thr Ile Pro Trp Ala Lys Ala Asn Leu Asn Tyr Thr
 60                  65                  70                  75 gcc cag gca ctc att ata tct tct gca tcc ata gcg gca tac ttt atc     292
Ala Gln Ala Leu Ile Ile Ser Ser Ala Ser Ile Ala Ala Tyr Phe Ile
             80                  85                  90 gct gct gac aaa acc atc tta gag tgc gca cgg aaa aat gca gag tac     340
Ala Ala Asp Lys Thr Ile Leu Glu Cys Ala Arg Lys Asn Ala Glu Tyr
         95                 100                 105 aaa tcg gct taagatgatg tgtaagacaa tgtgctcagc ttgcaatgct             389
Lys Ser Ala
        110 tgccatgact tgtgtttatg tgtatttcaa gtttctgaaa ctagcatttt gattttgtgt   449 tccaatgcaa tgagcattat ggaaaaaaaa aaaaaaaaa a                        490
```

<210> SEQ ID NO 30
<211> LENGTH: 110
<212> TYPE: PRT
<213> ORGANISM: Avicennia marina

<400> SEQUENCE: 30

```
Met Ala Ile Pro Ser Glu Ile Arg Asp Phe Ile Ala Ser Arg Asn Arg
  1               5                  10                  15

Ser Leu Val Ile Ala Ser Pro Lys Glu Asp Glu Lys Ile Leu Arg Ser
             20                  25                  30

Arg Gln Cys Thr Glu Glu Gly Ala Arg Ala Gly Ala Lys Ala Ala Ala
         35                  40                  45

Val Ala Cys Val Ala Ser Ala Ile Pro Thr Leu Val Ala Val Arg Thr
     50                  55                  60

Ile Pro Trp Ala Lys Ala Asn Leu Asn Tyr Thr Ala Gln Ala Leu Ile
 65                  70                  75                  80

Ile Ser Ser Ala Ser Ile Ala Ala Tyr Phe Ile Ala Ala Asp Lys Thr
                 85                  90                  95

Ile Leu Glu Cys Ala Arg Lys Asn Ala Glu Tyr Lys Ser Ala
            100                 105                 110
```

<210> SEQ ID NO 31
<211> LENGTH: 592
<212> TYPE: DNA
<213> ORGANISM: Avicennia marina
<220> FEATURE:
<221> NAME/KEY: CDS
<222> LOCATION: (75)..(320)

<400> SEQUENCE: 31

```
gcagtctcag ccttcctgct ctcctggtgc cttcaaattt gtgaatttct cgagtgctaa    60
aagattcagc caag atg cag aac gaa gag ggg caa aac atg gat ctc tac    110
```

```
                Met Gln Asn Glu Glu Gly Gln Asn Met Asp Leu Tyr
                 1               5                  10 atc ccc agg aaa tgc tct gcc acg aac agg ctg atc acc tcc aag gat       158
Ile Pro Arg Lys Cys Ser Ala Thr Asn Arg Leu Ile Thr Ser Lys Asp
         15                  20                  25 cat gct tct gtc cag atc aat gtt ggg cac ttg gat gag aat ggc cga       206
His Ala Ser Val Gln Ile Asn Val Gly His Leu Asp Glu Asn Gly Arg
 30                  35                  40 tac act ggc caa tac tct acc ttt gct ctt tgt gga ttc atc cgt gct       254
Tyr Thr Gly Gln Tyr Ser Thr Phe Ala Leu Cys Gly Phe Ile Arg Ala
     45                  50                  55                  60 cag ggt gat gct gac agt gct ctt gat agg ctc tgg cag aaa aag aaa       302
Gln Gly Asp Ala Asp Ser Ala Leu Asp Arg Leu Trp Gln Lys Lys Lys
                 65                  70                  75 gtc gaa acc agg cag cag tgatcctgct caattcagca gtgaaagttt              350
Val Glu Thr Arg Gln Gln
                 80 tttggttttt gttctgtgtt gtgttattta tgcttttcca gaatcaattt ctgtactgga     410 ttgagtatta aaatgtgga gctaaaggtt gggagacctg atgcctttgt tactcgagta      470 atcacaagta gatactgggc ttgtaatagc gtgataattg tgccttgctc ttgcctcatt     530 gactacgaat cagttatgtg attagacaat gttaatctcc aaaaaaaaaa aaaaaaaaa      590 aa                                                                    592

<210> SEQ ID NO 32
<211> LENGTH: 82
<212> TYPE: PRT
<213> ORGANISM: Avicennia marina

<400> SEQUENCE: 32

Met Gln Asn Glu Glu Gly Gln Asn Met Asp Leu Tyr Ile Pro Arg Lys
 1               5                  10                  15

Cys Ser Ala Thr Asn Arg Leu Ile Thr Ser Lys Asp His Ala Ser Val
             20                  25                  30

Gln Ile Asn Val Gly His Leu Asp Glu Asn Gly Arg Tyr Thr Gly Gln
         35                  40                  45

Tyr Ser Thr Phe Ala Leu Cys Gly Phe Ile Arg Ala Gln Gly Asp Ala
     50                  55                  60

Asp Ser Ala Leu Asp Arg Leu Trp Gln Lys Lys Lys Val Glu Thr Arg
 65                  70                  75                  80

Gln Gln

<210> SEQ ID NO 33
<211> LENGTH: 1806
<212> TYPE: DNA
<213> ORGANISM: Avicennia marina
<220> FEATURE:
<221> NAME/KEY: CDS
<222> LOCATION: (362)..(1552)

<400> SEQUENCE: 33
tgtgaaggta aagtctacag catatttcgc gccgctcgtt tgattacgtg ttgcttttat      60
ttgggaattt gatagcgctg agtagccgat gccgctggag ggtattgttg attttaggaa     120
tacgggtttg tttgattcgc agttttactg tctctagggt tgggccctga ggcttctggg    180
atttgggatt taatcgctga tcgaacagtt tcctggagaa atactcctta gtgcgcatat     240
atctgatttg ctgacgagaa attgatacac ggttatgcga ttgagttttg tttgcgccaa     300
```

```
agatactccg agtgctcgct agatgtggat aatccggagg gctgtttcga tgagatgagg    360 g atg tta tca ggg tta atg aac ttc ctg tgg gcc tgt ttt cgg cca agg   409
  Met Leu Ser Gly Leu Met Asn Phe Leu Trp Ala Cys Phe Arg Pro Arg
   1               5                  10                  15 gcg gat cga agt gtt cac acg ggt tca gat gca ggc ggt cgt cag gat     457
Ala Asp Arg Ser Val His Thr Gly Ser Asp Ala Gly Gly Arg Gln Asp
                20                  25                  30 ggg ctt tta tgg tat aag gac ttg ggg caa cat atc aat gga gag ttt     505
Gly Leu Leu Trp Tyr Lys Asp Leu Gly Gln His Ile Asn Gly Glu Phe
            35                  40                  45 tca atg gct gta gtt caa gca aat aac tta cta gag gat cag agt caa     553
Ser Met Ala Val Val Gln Ala Asn Asn Leu Leu Glu Asp Gln Ser Gln
 50                  55                  60 ctt gaa tct ggt tgc ctg agc ttg agt gat tca gga caa tat ggc act     601
Leu Glu Ser Gly Cys Leu Ser Leu Ser Asp Ser Gly Gln Tyr Gly Thr
 65                  70                  75                  80 ttt gtg ggg att tat gat gga cat gga ggt cct gag acc tct cgg ttt     649
Phe Val Gly Ile Tyr Asp Gly His Gly Gly Pro Glu Thr Ser Arg Phe
                 85                  90                  95 atc aat gac cat ctc ttc caa cat ata aag aga ttc aca gct gag cat     697
Ile Asn Asp His Leu Phe Gln His Ile Lys Arg Phe Thr Ala Glu His
            100                 105                 110 caa tca atg tca gct gag gtc att cac aag gcc att caa gcg act gaa     745
Gln Ser Met Ser Ala Glu Val Ile His Lys Ala Ile Gln Ala Thr Glu
        115                 120                 125 gaa ggt ttt ttc tcg gtt gtt agc aga caa tgg tcc atg caa cca cag     793
Glu Gly Phe Phe Ser Val Val Ser Arg Gln Trp Ser Met Gln Pro Gln
130                 135                 140 att gca gca gtt ggc tct tgc tgc ctt gtt ggt gtc atc tgt agt ggc     841
Ile Ala Ala Val Gly Ser Cys Cys Leu Val Gly Val Ile Cys Ser Gly
145                 150                 155                 160 act ctt tat gtt tcc aac ctt ggt gat tcc cgt gct gtt ctt ggg acg     889
Thr Leu Tyr Val Ser Asn Leu Gly Asp Ser Arg Ala Val Leu Gly Thr
            165                 170                 175 ctt tcc aag gct aca ggg gaa gta cag gct act caa ctc tca aca gag     937
Leu Ser Lys Ala Thr Gly Glu Val Gln Ala Thr Gln Leu Ser Thr Glu
        180                 185                 190 cat aat gca agt ttt gag tct gtg aga cgg gaa ctg cag tct ctg cac     985
His Asn Ala Ser Phe Glu Ser Val Arg Arg Glu Leu Gln Ser Leu His
    195                 200                 205 cca gat gac tca cag att gtg gtt cta aag cat aat gta tgg cga gtg    1033
Pro Asp Asp Ser Gln Ile Val Val Leu Lys His Asn Val Trp Arg Val
210                 215                 220 aag ggt ctt ata cag atc tca aga tca att gga gat gtg tat ttg aaa    1081
Lys Gly Leu Ile Gln Ile Ser Arg Ser Ile Gly Asp Val Tyr Leu Lys
225                 230                 235                 240 aag gct gaa ttc aac agg gag cct cta tat cag aaa ttt cga ctt cgt    1129
Lys Ala Glu Phe Asn Arg Glu Pro Leu Tyr Gln Lys Phe Arg Leu Arg
            245                 250                 255 gaa gct ttc aaa aga cca att ttg agc tca gaa cca gaa act act gtg    1177
Glu Ala Phe Lys Arg Pro Ile Leu Ser Ser Glu Pro Glu Thr Thr Val
        260                 265                 270 cac cag ctg ctg cct cat gat caa ttc att atc ttc gca tca gat ggc    1225
His Gln Leu Leu Pro His Asp Gln Phe Ile Ile Phe Ala Ser Asp Gly
    275                 280                 285 ctt tgg gag cac ctt tcc aac caa gaa gca gtt gat ctt gtt cag aaa    1273
Leu Trp Glu His Leu Ser Asn Gln Glu Ala Val Asp Leu Val Gln Lys
290                 295                 300 cat cca cac aat ggg att gct aga aga tta gta aaa gca gct ttg caa    1321
```

```
His Pro His Asn Gly Ile Ala Arg Arg Leu Val Lys Ala Ala Leu Gln
305                 310                 315                 320 gag gca gca aag aaa agg gaa atg agg tac tcg gat ttg aag aaa att      1369
Glu Ala Ala Lys Lys Arg Glu Met Arg Tyr Ser Asp Leu Lys Lys Ile
                325                 330                 335 gac cgt ggg gtt cgc cgt cat ttc cat gat gac atc act gtt gtg gtg      1417
Asp Arg Gly Val Arg Arg His Phe His Asp Asp Ile Thr Val Val Val
                340                 345                 350 gtg ttt ctt gac tca cac ctt gtg agc cgg gct agc tca gtc cgg ggc      1465
Val Phe Leu Asp Ser His Leu Val Ser Arg Ala Ser Ser Val Arg Gly
            355                 360                 365 cca aac atc tcc gtg aaa ggt ggc ggc atc agt ctg cct ccc aat gct      1513
Pro Asn Ile Ser Val Lys Gly Gly Gly Ile Ser Leu Pro Pro Asn Ala
370                 375                 380 ctt gca cct tgt gcc aca cca acg gag cca gtc cca aat tgatactgct       1562
Leu Ala Pro Cys Ala Thr Pro Thr Glu Pro Val Pro Asn
385                 390                 395 gtctcttcta atgttatttc ccgttagtcc tgttgtacta ttgttatgtg aatacaggta    1622
gcttcttaac ggataacagc ggcccttgaa ttctttaatc catactgtaa cttttaaccg    1682
gagactatta cttggcatag tttcaatgcc caagggatac atagactggg acaagccatc   1742
ttggcggtga caatcatcat agttaagttt tctgggcata tctttcaaaa aaaaaaaaaa   1802
aaaa                                                                  1806

<210> SEQ ID NO 34
<211> LENGTH: 397
<212> TYPE: PRT
<213> ORGANISM: Avicennia marina

<400> SEQUENCE: 34

Met Leu Ser Gly Leu Met Asn Phe Leu Trp Ala Cys Phe Arg Pro Arg
1               5                   10                  15

Ala Asp Arg Ser Val His Thr Gly Ser Asp Ala Gly Arg Gln Asp
            20                  25                  30

Gly Leu Leu Trp Tyr Lys Asp Leu Gly Gln His Ile Asn Gly Glu Phe
        35                  40                  45

Ser Met Ala Val Val Gln Ala Asn Asn Leu Leu Glu Asp Gln Ser Gln
    50                  55                  60

Leu Glu Ser Gly Cys Leu Ser Leu Ser Asp Ser Gly Gln Tyr Gly Thr
65                  70                  75                  80

Phe Val Gly Ile Tyr Asp Gly His Gly Gly Pro Glu Thr Ser Arg Phe
                85                  90                  95

Ile Asn Asp His Leu Phe Gln His Ile Lys Arg Phe Thr Ala Glu His
            100                 105                 110

Gln Ser Met Ser Ala Glu Val Ile His Lys Ala Ile Gln Ala Thr Glu
        115                 120                 125

Glu Gly Phe Phe Ser Val Val Ser Arg Gln Trp Ser Met Gln Pro Gln
    130                 135                 140

Ile Ala Ala Val Gly Ser Cys Cys Leu Val Gly Val Ile Cys Ser Gly
145                 150                 155                 160

Thr Leu Tyr Val Ser Asn Leu Gly Asp Ser Arg Ala Val Leu Gly Thr
                165                 170                 175

Leu Ser Lys Ala Thr Gly Glu Val Gln Ala Thr Gln Leu Ser Thr Glu
            180                 185                 190

His Asn Ala Ser Phe Glu Ser Val Arg Arg Glu Leu Gln Ser Leu His
        195                 200                 205
```

```
Pro Asp Asp Ser Gln Ile Val Val Leu Lys His Asn Val Trp Arg Val
    210                 215                 220

Lys Gly Leu Ile Gln Ile Ser Arg Ser Ile Gly Asp Val Tyr Leu Lys
225                 230                 235                 240

Lys Ala Glu Phe Asn Arg Glu Pro Leu Tyr Gln Lys Phe Arg Leu Arg
                245                 250                 255

Glu Ala Phe Lys Arg Pro Ile Leu Ser Ser Pro Glu Thr Thr Val
            260                 265                 270

His Gln Leu Leu Pro His Asp Gln Phe Ile Ile Phe Ala Ser Asp Gly
            275                 280                 285

Leu Trp Glu His Leu Ser Asn Gln Glu Ala Val Asp Leu Val Gln Lys
    290                 295                 300

His Pro His Asn Gly Ile Ala Arg Arg Leu Val Lys Ala Ala Leu Gln
305                 310                 315                 320

Glu Ala Ala Lys Lys Arg Glu Met Arg Tyr Ser Asp Leu Lys Lys Ile
                325                 330                 335

Asp Arg Gly Val Arg Arg His Phe His Asp Ile Thr Val Val Val
            340                 345                 350

Val Phe Leu Asp Ser His Leu Val Ser Arg Ala Ser Ser Val Arg Gly
    355                 360                 365

Pro Asn Ile Ser Val Lys Gly Gly Ile Ser Leu Pro Pro Asn Ala
    370                 375                 380

Leu Ala Pro Cys Ala Thr Pro Thr Glu Pro Val Pro Asn
385                 390                 395

<210> SEQ ID NO 35
<211> LENGTH: 743
<212> TYPE: DNA
<213> ORGANISM: Mesembryanthemum crystallinum
<220> FEATURE:
<221> NAME/KEY: CDS
<222> LOCATION: (1)..(420)

<400> SEQUENCE: 35 cct gag cta gca cct aaa gat ggg gat ttc cgt ttc aat atc tct gag    48
Pro Glu Leu Ala Pro Lys Asp Gly Asp Phe Arg Phe Asn Ile Ser Glu
  1               5                  10                  15 ctt gaa gct atg cta cca gct gga act gta gat cat gct gtt gaa agg    96
Leu Glu Ala Met Leu Pro Ala Gly Thr Val Asp His Ala Val Glu Arg
             20                  25                  30 att tat caa gag atg ccg cgg tgg gaa gag act gtt tta ggt tcc agg   144
Ile Tyr Gln Glu Met Pro Arg Trp Glu Glu Thr Val Leu Gly Ser Arg
         35                  40                  45 agc aga tat gag cat gtc att cag gca ctt gca gat aaa tac cct tca   192
Ser Arg Tyr Glu His Val Ile Gln Ala Leu Ala Asp Lys Tyr Pro Ser
     50                  55                  60 gaa aat ttg ttg cta gtt acg cat ggt gaa ggt gtt ggg act tca gtt   240
Glu Asn Leu Leu Leu Val Thr His Gly Glu Gly Val Gly Thr Ser Val
 65                  70                  75                  80 gca acg ttt ttg aaa ggc gct gtt gtt tat gaa gta aag tat tgt gct   288
Ala Thr Phe Leu Lys Gly Ala Val Val Tyr Glu Val Lys Tyr Cys Ala
                 85                  90                  95 tat tca caa gca aca aga cgc atc agc tat gga gaa ggc gag tca ttt   336
Tyr Ser Gln Ala Thr Arg Arg Ile Ser Tyr Gly Glu Gly Glu Ser Phe
            100                 105                 110 act gct ggt acc ttt cag ttg gtc act gcc tca gac caa acc ggt att   384
Thr Ala Gly Thr Phe Gln Leu Val Thr Ala Ser Asp Gln Thr Gly Ile
        115                 120                 125
```

```
ggt tac tac aca tct agc agc ttg tct gat ggt gta tgacttatcg         430
Gly Tyr Tyr Thr Ser Ser Ser Leu Ser Asp Gly Val
        130                 135                 140 gaactcccga gtttctgcat tctgaaaggt gcttttgat ttccgaataa ttcttcaaat     490
ccacatgtca gaagatccat tctttaggtc agatgtctat ctactgctcc cagccttgag    550
ctgctcatgg gtattggtgc ccttctattt ttaggtagag tctttgagta agccttgcca    610
catcaaggcc tcagattatt gaatgtacaa cagaataggt tgtagcttca ttggctagta    670
cagtgacctc tttcatgggt ctgaaacatc aatataaagg tttgaatggc aaaaaaaaaa    730
aaaaaaaaaa aaa                                                      743

<210> SEQ ID NO 36
<211> LENGTH: 140
<212> TYPE: PRT
<213> ORGANISM: Mesembryanthemum crystallinum

<400> SEQUENCE: 36

Pro Glu Leu Ala Pro Lys Asp Gly Asp Phe Arg Phe Asn Ile Ser Glu
 1               5                  10                  15

Leu Glu Ala Met Leu Pro Ala Gly Thr Val Asp His Ala Val Glu Arg
                20                  25                  30

Ile Tyr Gln Glu Met Pro Arg Trp Glu Glu Thr Val Leu Gly Ser Arg
            35                  40                  45

Ser Arg Tyr Glu His Val Ile Gln Ala Leu Ala Asp Lys Tyr Pro Ser
        50                  55                  60

Glu Asn Leu Leu Leu Val Thr His Gly Glu Gly Val Gly Thr Ser Val
 65                 70                  75                  80

Ala Thr Phe Leu Lys Gly Ala Val Val Tyr Glu Val Lys Tyr Cys Ala
                85                  90                  95

Tyr Ser Gln Ala Thr Arg Arg Ile Ser Tyr Gly Glu Gly Glu Ser Phe
            100                 105                 110

Thr Ala Gly Thr Phe Gln Leu Val Thr Ala Ser Asp Gln Thr Gly Ile
        115                 120                 125

Gly Tyr Tyr Thr Ser Ser Ser Leu Ser Asp Gly Val
    130                 135                 140

<210> SEQ ID NO 37
<211> LENGTH: 348
<212> TYPE: DNA
<213> ORGANISM: Sueada japonica
<220> FEATURE:
<221> NAME/KEY: CDS
<222> LOCATION: (1)..(246)

<400> SEQUENCE: 37 atc att gct ccc cta gct att ggt ttg atc gtt ggt gcc aac atc tta      48
Ile Ile Ala Pro Leu Ala Ile Gly Leu Ile Val Gly Ala Asn Ile Leu
 1               5                  10                  15 gcc gga ggt gca ttt gat ggt gcc tca atg aac cct gcc gtc tct ttt      96
Ala Gly Gly Ala Phe Asp Gly Ala Ser Met Asn Pro Ala Val Ser Phe
                20                  25                  30 ggc ccc gcc gtg gtt agc tgg agc tgg gcc aac cac tgg gtc tac tgg     144
Gly Pro Ala Val Val Ser Trp Ser Trp Ala Asn His Trp Val Tyr Trp
            35                  40                  45 gca ggc cca ctc att ggt ggt gga ctt gct ggt ctc gtt tat gag ttt     192
Ala Gly Pro Leu Ile Gly Gly Gly Leu Ala Gly Leu Val Tyr Glu Phe
        50                  55                  60
```

-continued

```
atc ttt att ggt cac caa gag cca gct tcc gct gac tac cag aga ctc      240
Ile Phe Ile Gly His Gln Glu Pro Ala Ser Ala Asp Tyr Gln Arg Leu
 65                  70                  75                  80 tct gct taagaatttt aattctttgc cctagggaaa aatgtttcat gcatgtattt       296
Ser Ala tggtattttg ttgggtctaa aattttatga agggaaaaaa aaaaaaaaaa aa            348
```

<210> SEQ ID NO 38
<211> LENGTH: 82
<212> TYPE: PRT
<213> ORGANISM: Sueada japonica

<400> SEQUENCE: 38

```
Ile Ile Ala Pro Leu Ala Ile Gly Leu Ile Val Gly Ala Asn Ile Leu
  1               5                  10                  15

Ala Gly Gly Ala Phe Asp Gly Ala Ser Met Asn Pro Ala Val Ser Phe
                 20                  25                  30

Gly Pro Ala Val Val Ser Trp Ser Trp Ala Asn His Trp Val Tyr Trp
             35                  40                  45

Ala Gly Pro Leu Ile Gly Gly Leu Ala Gly Leu Val Tyr Glu Phe
         50                  55                  60

Ile Phe Ile Gly His Gln Glu Pro Ala Ser Ala Asp Tyr Gln Arg Leu
 65                  70                  75                  80

Ser Ala
```

<210> SEQ ID NO 39
<211> LENGTH: 1602
<212> TYPE: DNA
<213> ORGANISM: Sueada japonica
<220> FEATURE:
<221> NAME/KEY: CDS
<222> LOCATION: (1)..(1419)

<400> SEQUENCE: 39

```
cac acc gtt gat tta acc att gaa gct atg atg ctc gat tct caa gct      48
His Thr Val Asp Leu Thr Ile Glu Ala Met Met Leu Asp Ser Gln Ala
  1               5                  10                  15 tct gat ctt gac aaa gaa gaa cgt cct gag att ctt tca atg ctt ccg      96
Ser Asp Leu Asp Lys Glu Glu Arg Pro Glu Ile Leu Ser Met Leu Pro
                 20                  25                  30 cct ctt gaa gga aaa tgc ctc ttg gaa ctt ggg gct ggt att ggt cgt     144
Pro Leu Glu Gly Lys Cys Leu Leu Glu Leu Gly Ala Gly Ile Gly Arg
             35                  40                  45 ttt act ggt gaa ttg gct gag aaa gct ggc cag gtt att gct ctg gat     192
Phe Thr Gly Glu Leu Ala Glu Lys Ala Gly Gln Val Ile Ala Leu Asp
         50                  55                  60 ttc att gag agt gct atc aag aag aat gaa gta atc aat ggg cac tac     240
Phe Ile Glu Ser Ala Ile Lys Lys Asn Glu Val Ile Asn Gly His Tyr
 65                  70                  75                  80 aaa aat gtc aag ttt atg tgt gct gat gtg act tct ccc act ctc agt     288
Lys Asn Val Lys Phe Met Cys Ala Asp Val Thr Ser Pro Thr Leu Ser
                 85                  90                  95 ttc cca cca cat tca ttg gat gtg ata ttc tcc aat tgg tta ctc atg     336
Phe Pro Pro His Ser Leu Asp Val Ile Phe Ser Asn Trp Leu Leu Met
                100                 105                 110 tat ctt tct gat gaa gag gtg gaa aat ttg gtt gaa aga atg ttg aaa     384
Tyr Leu Ser Asp Glu Glu Val Glu Asn Leu Val Glu Arg Met Leu Lys
            115                 120                 125 tgg ttg aag cca ggg ggt tac att ttc ttc aga gaa tct tgt ttc cat     432
Trp Leu Lys Pro Gly Gly Tyr Ile Phe Phe Arg Glu Ser Cys Phe His
```

-continued

```
        130                 135                 140
caa tct ggg gat cac aaa cgc aaa agc aat ccc acc cac tac cgt gaa      480
Gln Ser Gly Asp His Lys Arg Lys Ser Asn Pro Thr His Tyr Arg Glu
145             150                 155                 160 cct agg ttc tac act aag gcc ttc aaa gag tgt cat ttg caa gat gga      528
Pro Arg Phe Tyr Thr Lys Ala Phe Lys Glu Cys His Leu Gln Asp Gly
                    165                 170                 175 tct gga aac tct tat gag ctc tcc cta ctt agc tgc aaa tgt att gga      576
Ser Gly Asn Ser Tyr Glu Leu Ser Leu Leu Ser Cys Lys Cys Ile Gly
                180                 185                 190 gct tat gtc aga aac aag aaa aac cag aac cag att agt tgg ttg tgg      624
Ala Tyr Val Arg Asn Lys Lys Asn Gln Asn Gln Ile Ser Trp Leu Trp
            195                 200                 205 caa aaa gtt gat tct aag gat gat aag ggg ttc cag cga ttt ctg gat      672
Gln Lys Val Asp Ser Lys Asp Asp Lys Gly Phe Gln Arg Phe Leu Asp
        210                 215                 220 act agc cag tac aag tgt aat agc att ctg cga tat gag cgt gta ttt      720
Thr Ser Gln Tyr Lys Cys Asn Ser Ile Leu Arg Tyr Glu Arg Val Phe
225                 230                 235                 240 ggc cct ggt tat gtt agc act gga gga tat gaa acc acc aaa gag ttt      768
Gly Pro Gly Tyr Val Ser Thr Gly Gly Tyr Glu Thr Thr Lys Glu Phe
                    245                 250                 255 gtg tca atg ctg gac ttg aag cct ggc cag aag gtc ctg gat gtt ggt      816
Val Ser Met Leu Asp Leu Lys Pro Gly Gln Lys Val Leu Asp Val Gly
                260                 265                 270 tgt gga att ggt gga ggt gac ttt tac atg gcg gag acc ttt gat gtt      864
Cys Gly Ile Gly Gly Gly Asp Phe Tyr Met Ala Glu Thr Phe Asp Val
            275                 280                 285 gag gtt gtt gga ttt gat ctc tcc gtt aat atg att tcc ttt gcc ctt      912
Glu Val Val Gly Phe Asp Leu Ser Val Asn Met Ile Ser Phe Ala Leu
        290                 295                 300 gag cgt tct att ggg ctt aaa tgt gct gtt gag ttt gag gta gca gat      960
Glu Arg Ser Ile Gly Leu Lys Cys Ala Val Glu Phe Glu Val Ala Asp
305                 310                 315                 320 tgc acc aag ata aac tac cct gat aac tct ttt gat gtc atc tat agc     1008
Cys Thr Lys Ile Asn Tyr Pro Asp Asn Ser Phe Asp Val Ile Tyr Ser
                    325                 330                 335 cgt gac acc att ctg cat att cag gac aag cct gcg ttg ttt aga tcc     1056
Arg Asp Thr Ile Leu His Ile Gln Asp Lys Pro Ala Leu Phe Arg Ser
                340                 345                 350 ttc tac aaa tgg ttg aag cca gga ggt aaa gtt cta atc agt gat tac     1104
Phe Tyr Lys Trp Leu Lys Pro Gly Gly Lys Val Leu Ile Ser Asp Tyr
            355                 360                 365 tgc aag aaa gct ggt cca ccc tca cct gaa ttc gcc gct tac att aag     1152
Cys Lys Lys Ala Gly Pro Pro Ser Pro Glu Phe Ala Ala Tyr Ile Lys
        370                 375                 380 cag agg gga tat gat ctc cat gat gta aag gaa tat ggg cag atg ctt     1200
Gln Arg Gly Tyr Asp Leu His Asp Val Lys Glu Tyr Gly Gln Met Leu
385                 390                 395                 400 aaa gat gct gga ttt gtt gat gtt ctt gcc gag gat aga act gag cag     1248
Lys Asp Ala Gly Phe Val Asp Val Leu Ala Glu Asp Arg Thr Glu Gln
                    405                 410                 415 ttc att cga gtt cta cgg aag gaa cta gag act gtt gag aag gaa aag     1296
Phe Ile Arg Val Leu Arg Lys Glu Leu Glu Thr Val Glu Lys Glu Lys
                420                 425                 430 gat gtg ttc att agt gat ttc tct gag gag gat tac aat gac att gtt     1344
Asp Val Phe Ile Ser Asp Phe Ser Glu Glu Asp Tyr Asn Asp Ile Val
            435                 440                 445 gga ggt tgg aat gat aag ttg cgg agg act gcc aag ggt gag caa cga     1392
```

-continued

```
Gly Gly Trp Asn Asp Lys Leu Arg Arg Thr Ala Lys Gly Glu Gln Arg
    450                 455                 460 tgg ggt ctg ttc gtt gcc aag aag aag tgaagaatca gttgccgcac          1439
Trp Gly Leu Phe Val Ala Lys Lys Lys
465                 470 tggcactgtc gatttcctag tattaatctt caatgttttc atgtaatgta cttctacatg  1499
taaaattgcc aataagttgc atttcgcaga ctgtaagatg attaatcata ttttatcttt  1559
taattaatca tggatttatg caaaaaaaaa aaaaaaaaa aaa                     1602

<210> SEQ ID NO 40
<211> LENGTH: 473
<212> TYPE: PRT
<213> ORGANISM: Sueada japonica

<400> SEQUENCE: 40

His Thr Val Asp Leu Thr Ile Glu Ala Met Met Leu Asp Ser Gln Ala
  1               5                  10                  15

Ser Asp Leu Asp Lys Glu Arg Pro Glu Ile Leu Ser Met Leu Pro
             20                  25                  30

Pro Leu Glu Gly Lys Cys Leu Glu Leu Gly Ala Gly Ile Gly Arg
         35                  40                  45

Phe Thr Gly Glu Leu Ala Glu Lys Ala Gly Gln Val Ile Ala Leu Asp
     50                  55                  60

Phe Ile Glu Ser Ala Ile Lys Lys Asn Glu Val Ile Asn Gly His Tyr
 65                  70                  75                  80

Lys Asn Val Lys Phe Met Cys Ala Asp Val Thr Ser Pro Thr Leu Ser
                 85                  90                  95

Phe Pro Pro His Ser Leu Asp Val Ile Phe Ser Asn Trp Leu Leu Met
            100                 105                 110

Tyr Leu Ser Asp Glu Glu Val Glu Asn Leu Val Glu Arg Met Leu Lys
        115                 120                 125

Trp Leu Lys Pro Gly Gly Tyr Ile Phe Phe Arg Glu Ser Cys Phe His
    130                 135                 140

Gln Ser Gly Asp His Lys Arg Lys Ser Asn Pro Thr His Tyr Arg Glu
145                 150                 155                 160

Pro Arg Phe Tyr Thr Lys Ala Phe Lys Glu Cys His Leu Gln Asp Gly
                165                 170                 175

Ser Gly Asn Ser Tyr Glu Leu Ser Leu Leu Ser Cys Lys Cys Ile Gly
            180                 185                 190

Ala Tyr Val Arg Asn Lys Lys Asn Gln Asn Gln Ile Ser Trp Leu Trp
        195                 200                 205

Gln Lys Val Asp Ser Lys Asp Lys Gly Phe Gln Arg Phe Leu Asp
    210                 215                 220

Thr Ser Gln Tyr Lys Cys Asn Ser Ile Leu Arg Tyr Glu Arg Val Phe
225                 230                 235                 240

Gly Pro Gly Tyr Val Ser Thr Gly Gly Tyr Glu Thr Lys Glu Phe
                245                 250                 255

Val Ser Met Leu Asp Leu Lys Pro Gly Gln Lys Val Leu Asp Val Gly
            260                 265                 270

Cys Gly Ile Gly Gly Gly Asp Phe Tyr Met Ala Glu Thr Phe Asp Val
        275                 280                 285

Glu Val Val Gly Phe Asp Leu Ser Val Asn Met Ile Ser Phe Ala Leu
    290                 295                 300

Glu Arg Ser Ile Gly Leu Lys Cys Ala Val Glu Phe Glu Val Ala Asp
```

```
                305                 310                 315                 320
Cys Thr Lys Ile Asn Tyr Pro Asp Asn Ser Phe Asp Val Ile Tyr Ser
                    325                 330                 335

Arg Asp Thr Ile Leu His Ile Gln Asp Lys Pro Ala Leu Phe Arg Ser
                340                 345                 350

Phe Tyr Lys Trp Leu Lys Pro Gly Gly Lys Val Leu Ile Ser Asp Tyr
                355                 360                 365

Cys Lys Lys Ala Gly Pro Pro Ser Pro Glu Phe Ala Ala Tyr Ile Lys
                370                 375                 380

Gln Arg Gly Tyr Asp Leu His Asp Val Lys Glu Tyr Gly Gln Met Leu
385                 390                 395                 400

Lys Asp Ala Gly Phe Val Asp Val Leu Ala Glu Asp Arg Thr Glu Gln
                405                 410                 415

Phe Ile Arg Val Leu Arg Lys Glu Leu Glu Thr Val Glu Lys Glu Lys
                420                 425                 430

Asp Val Phe Ile Ser Asp Phe Ser Glu Glu Asp Tyr Asn Asp Ile Val
                435                 440                 445

Gly Gly Trp Asn Asp Lys Leu Arg Arg Thr Ala Lys Gly Glu Gln Arg
450                 455                 460

Trp Gly Leu Phe Val Ala Lys Lys Lys
465                 470

<210> SEQ ID NO 41
<211> LENGTH: 1251
<212> TYPE: DNA
<213> ORGANISM: Salsola komarovii
<220> FEATURE:
<221> NAME/KEY: CDS
<222> LOCATION: (1)..(933)

<400> SEQUENCE: 41 cag cca ttt ggc aca att aat gga tca ctt cgt gtt act gta caa ggt      48
Gln Pro Phe Gly Thr Ile Asn Gly Ser Leu Arg Val Thr Val Gln Gly
1               5                   10                  15 gag gtc att gaa caa tct ttt gga gag gag cac ttg tgt ttt aga aca      96
Glu Val Ile Glu Gln Ser Phe Gly Glu Glu His Leu Cys Phe Arg Thr
                20                  25                  30 tta cag cgg tac aca gct gcc aca ctt gag cat gga atg cat cca cca     144
Leu Gln Arg Tyr Thr Ala Ala Thr Leu Glu His Gly Met His Pro Pro
            35                  40                  45 atc tct cct aaa cca gaa tgg cgt gca ctt ttg gac gag atg gct gtt     192
Ile Ser Pro Lys Pro Glu Trp Arg Ala Leu Leu Asp Glu Met Ala Val
        50                  55                  60 gtt gcc acc aag gaa tac cgc tct gtt gtt ttt cat gag cct cgc ttt     240
Val Ala Thr Lys Glu Tyr Arg Ser Val Val Phe His Glu Pro Arg Phe
65                  70                  75                  80 gtc gag tac ttc cgc agt gct aca cca gag aca gag tat ggg cgt atg     288
Val Glu Tyr Phe Arg Ser Ala Thr Pro Glu Thr Glu Tyr Gly Arg Met
                85                  90                  95 aat att gga agc cgt cct gca aag aga aag cca gga gga gga att gaa     336
Asn Ile Gly Ser Arg Pro Ala Lys Arg Lys Pro Gly Gly Gly Ile Glu
            100                 105                 110 act ctg cgt gca att cct tgg ata ttt tcg tgg aca caa acc agg ttt     384
Thr Leu Arg Ala Ile Pro Trp Ile Phe Ser Trp Thr Gln Thr Arg Phe
        115                 120                 125 cat tta cct gtg tgg ctt ggg gtt gga gca gct ttt aag cat gcc ctt     432
His Leu Pro Val Trp Leu Gly Val Gly Ala Ala Phe Lys His Ala Leu
    130                 135                 140
```

```
gac aag gac att aag aat ctt tcg ata ctc aag gcc atg tat aat gag    480
Asp Lys Asp Ile Lys Asn Leu Ser Ile Leu Lys Ala Met Tyr Asn Glu
145                 150                 155                 160 tgg ccg ttc ttc aga gtg act att gat ctc tta gaa atg gtt ttc act    528
Trp Pro Phe Phe Arg Val Thr Ile Asp Leu Leu Glu Met Val Phe Thr
                165                 170                 175 aaa gga gac cct gga att gct gct tta tat gac aag ctt ctg gtg gca    576
Lys Gly Asp Pro Gly Ile Ala Ala Leu Tyr Asp Lys Leu Leu Val Ala
            180                 185                 190 gag gat ttg aag ccc ttt ggg gaa aag ttg agg aaa agt ttc gaa gat    624
Glu Asp Leu Lys Pro Phe Gly Glu Lys Leu Arg Lys Ser Phe Glu Asp
        195                 200                 205 acc aaa ctc ctt ctc ctt aag gtt gct ggg cac aag gag tta ctg gaa    672
Thr Lys Leu Leu Leu Leu Lys Val Ala Gly His Lys Glu Leu Leu Glu
    210                 215                 220 gga gat cct tac ttg aaa cag aga ctc cga ctt cgt gat cct tac att    720
Gly Asp Pro Tyr Leu Lys Gln Arg Leu Arg Leu Arg Asp Pro Tyr Ile
225                 230                 235                 240 aca acc ctt aat gtt ttc caa gca tat act ctg aag cgg atc cgt gat    768
Thr Thr Leu Asn Val Phe Gln Ala Tyr Thr Leu Lys Arg Ile Arg Asp
                245                 250                 255 ccc aat ttc cat gta gct gaa ggg cca cac tta tcc aag gaa gta ttg    816
Pro Asn Phe His Val Ala Glu Gly Pro His Leu Ser Lys Glu Val Leu
            260                 265                 270 gaa tca aac aat gct gag ctt gtg aag ctc aat cct act agt gag tat    864
Glu Ser Asn Asn Ala Glu Leu Val Lys Leu Asn Pro Thr Ser Glu Tyr
        275                 280                 285 cct cct ggc ctt gag gac acc ctt atc ttg acc atg aag ggt att gct    912
Pro Pro Gly Leu Glu Asp Thr Leu Ile Leu Thr Met Lys Gly Ile Ala
    290                 295                 300 gct ggc atg cag aac acc ggt taactgacac gtgttgcacg tctattgcaa      963
Ala Gly Met Gln Asn Thr Gly
305                 310 ctattcctca actccttctg gtttggggat ccgggctcgg agatagccat cgttggtgat   1023
gtgctgtatg agcacctaat tgtattcaaa gtctgtattt caagtctatt gtatttgtat   1083
tttgttcttc tgtatgtttt tgttatttct acttatggtt gggttgtgtc acttgtgact   1143 aataccccgac tgtgtaataa atggttgttg tactgatgaa cagtttgttt tcttctacgt   1203
gagttatatt gatgagttta tcttttatta aaaaaaaaa aaaaaaaa               1251

<210> SEQ ID NO 42
<211> LENGTH: 311
<212> TYPE: PRT
<213> ORGANISM: Salsola komarovii

<400> SEQUENCE: 42

Gln Pro Phe Gly Thr Ile Asn Gly Ser Leu Arg Val Thr Val Gln Gly
  1               5                  10                  15

Glu Val Ile Glu Gln Ser Phe Gly Glu His Leu Cys Phe Arg Thr
                20                  25                  30

Leu Gln Arg Tyr Thr Ala Ala Thr Leu Glu His Gly Met His Pro Pro
            35                  40                  45

Ile Ser Pro Lys Pro Glu Trp Arg Ala Leu Leu Asp Glu Met Ala Val
        50                  55                  60

Val Ala Thr Lys Glu Tyr Arg Ser Val Val Phe His Glu Pro Arg Phe
65                  70                  75                  80

Val Glu Tyr Phe Arg Ser Ala Thr Pro Glu Thr Glu Tyr Gly Arg Met
                85                  90                  95
```

```
Asn Ile Gly Ser Arg Pro Ala Lys Arg Lys Pro Gly Gly Ile Glu
            100                 105                 110
Thr Leu Arg Ala Ile Pro Trp Ile Phe Ser Trp Thr Gln Thr Arg Phe
        115                 120                 125
His Leu Pro Val Trp Leu Gly Val Gly Ala Ala Phe Lys His Ala Leu
    130                 135                 140
Asp Lys Asp Ile Lys Asn Leu Ser Ile Leu Lys Ala Met Tyr Asn Glu
145                 150                 155                 160
Trp Pro Phe Phe Arg Val Thr Ile Asp Leu Leu Glu Met Val Phe Thr
                165                 170                 175
Lys Gly Asp Pro Gly Ile Ala Ala Leu Tyr Asp Lys Leu Leu Val Ala
            180                 185                 190
Glu Asp Leu Lys Pro Phe Gly Glu Lys Leu Arg Lys Ser Phe Glu Asp
        195                 200                 205
Thr Lys Leu Leu Leu Lys Val Ala Gly His Lys Glu Leu Leu Glu
    210                 215                 220
Gly Asp Pro Tyr Leu Lys Gln Arg Leu Arg Leu Arg Asp Pro Tyr Ile
225                 230                 235                 240
Thr Thr Leu Asn Val Phe Gln Ala Tyr Thr Leu Lys Arg Ile Arg Asp
                245                 250                 255
Pro Asn Phe His Val Ala Glu Gly Pro His Leu Ser Lys Glu Val Leu
            260                 265                 270
Glu Ser Asn Asn Ala Glu Leu Val Lys Leu Asn Pro Thr Ser Glu Tyr
        275                 280                 285
Pro Pro Gly Leu Glu Asp Thr Leu Ile Leu Thr Met Lys Gly Ile Ala
    290                 295                 300
Ala Gly Met Gln Asn Thr Gly
305                 310

<210> SEQ ID NO 43
<211> LENGTH: 637
<212> TYPE: DNA
<213> ORGANISM: Avicennia marina
<220> FEATURE:
<221> NAME/KEY: CDS
<222> LOCATION: (1)..(339)

<400> SEQUENCE: 43 caa tac ttg gta aat gaa gtg aag aaa act gtt cag ggg cgt gct caa    48
Gln Tyr Leu Val Asn Glu Val Lys Lys Thr Val Gln Gly Arg Ala Gln
1               5                   10                  15 ctt ggt gtg gaa gca ttt gct gat gcg ctt ctt gtg gtt cca aag acg    96
Leu Gly Val Glu Ala Phe Ala Asp Ala Leu Leu Val Val Pro Lys Thr
            20                  25                  30 ctt gcc gag aac tct ggc ctt gat acc cag gat ttg att att gaa ctt   144
Leu Ala Glu Asn Ser Gly Leu Asp Thr Gln Asp Leu Ile Ile Glu Leu
        35                  40                  45 acg gga gaa tat gaa aaa ggg aat gtg gta gga ctt aat cta cac aca   192
Thr Gly Glu Tyr Glu Lys Gly Asn Val Val Gly Leu Asn Leu His Thr
    50                  55                  60 gga gaa cct ata gat cct caa atg gag ggt atc ttt gac aat tat tcc   240
Gly Glu Pro Ile Asp Pro Gln Met Glu Gly Ile Phe Asp Asn Tyr Ser
65                  70                  75                  80 gtg aag cgt cag atc ata aac tca ggc ccc gtt att gca tct cag ctg   288
Val Lys Arg Gln Ile Ile Asn Ser Gly Pro Val Ile Ala Ser Gln Leu
                85                  90                  95 cta ctt gtc gac gag gtt att cgt gct ggt cgt aac atg cgt aaa ccg   336
```

-continued

```
Leu Leu Val Asp Glu Val Ile Arg Ala Gly Arg Asn Met Arg Lys Pro
            100                 105                 110 aat tagctttcac cctagttttt gtgatgttgg tgaagatggt aattttattt           389
Asn aggtagggtc atggttcctt tgtttagcc taagcactat gtattcattg ccacttgaga    449
tttgaatttt gatcatcagg cggttgaact tttcgcctgt tacaaattgc accagaaatt   509
attcgaccat gggtatgcat ctacttgtgt tgtacctgac ttggctaagt tatttgaaga   569
tacactctgt gctcagcaaa gaattggaaa aaaggaatt gatttcatca aaaaaaaaa     629 aaaaaaaa                                                             637
```

<210> SEQ ID NO 44
<211> LENGTH: 113
<212> TYPE: PRT
<213> ORGANISM: Avicennia marina

<400> SEQUENCE: 44

```
Gln Tyr Leu Val Asn Glu Val Lys Lys Thr Val Gln Gly Arg Ala Gln
  1               5                  10                  15

Leu Gly Val Glu Ala Phe Ala Asp Ala Leu Leu Val Val Pro Lys Thr
             20                  25                  30

Leu Ala Glu Asn Ser Gly Leu Asp Thr Gln Asp Leu Ile Ile Glu Leu
         35                  40                  45

Thr Gly Glu Tyr Glu Lys Gly Asn Val Val Gly Leu Asn Leu His Thr
     50                  55                  60

Gly Glu Pro Ile Asp Pro Gln Met Glu Gly Ile Phe Asp Asn Tyr Ser
 65                  70                  75                  80

Val Lys Arg Gln Ile Ile Asn Ser Gly Pro Val Ile Ala Ser Gln Leu
                 85                  90                  95

Leu Leu Val Asp Glu Val Ile Arg Ala Gly Arg Asn Met Arg Lys Pro
            100                 105                 110

Asn
```

<210> SEQ ID NO 45
<211> LENGTH: 741
<212> TYPE: DNA
<213> ORGANISM: Avicennia marina
<220> FEATURE:
<221> NAME/KEY: CDS
<222> LOCATION: (3)..(293)

<400> SEQUENCE: 45

```
aa gag atc aat tgt ctt gaa tgg gag aac ttt gct ttc cat ccc agc       47
   Glu Ile Asn Cys Leu Glu Trp Glu Asn Phe Ala Phe His Pro Ser
     1               5                  10                  15 cca ctc att gtt ctt gtt ttt gaa aga tac aac agg gca agt gat aac      95
Pro Leu Ile Val Leu Val Phe Glu Arg Tyr Asn Arg Ala Ser Asp Asn
             20                  25                  30 tgg aaa gct ttg aag gag ttg gaa aag gcg gca gaa gtt tac tgg aag     143
Trp Lys Ala Leu Lys Glu Leu Glu Lys Ala Ala Glu Val Tyr Trp Lys
         35                  40                  45 gca aaa gat cga ctg cct cct cgg acg gtc aag ata gat ata aac atc    191
Ala Lys Asp Arg Leu Pro Pro Arg Thr Val Lys Ile Asp Ile Asn Ile
     50                  55                  60 gaa agg gat tta gca tat gca ctc aag gtt aaa gaa tgc ccg cag ata    239
Glu Arg Asp Leu Ala Tyr Ala Leu Lys Val Lys Glu Cys Pro Gln Ile
 65                  70                  75 ctg ttc tta cgc gga aac agg ata tta tac aga gag aaa ggt agc cca    287
Leu Phe Leu Arg Gly Asn Arg Ile Leu Tyr Arg Glu Lys Gly Ser Pro
```

```
                Leu Phe Leu Arg Gly Asn Arg Ile Leu Tyr Arg Glu Lys Gly Ser Pro
                 80                  85                  90                  95 ttt ctc tgatattgca tgtacatcag atctttcaat ctgcaccaga accaattgag            343
Phe Leu tttaccatca tttccagaaa ttagatcatc ggatgaattg gttcagatga tcgcgcattt        403
ctattacaat gcaaaaaagc cttcgtgcat cgatgatgca gctttctctt caccacatca        463
ctgaaggtga ggttgtcaaa tggaatccag catcagtcat tagggaggac tgaagctgta        523
cggagggaag tggtttaaat tcagattgga tctttgaagt gggcagtggt gattgaaacg        583
ccaaaagttt ctgaggaata accttgttgg gattttgcag tgaactgtag taactttctc        643
gcatgtaaaa ctagactttc atcaatcaac caccaaccct tttatgtata tgaaacctat        703
gaggttgaaa tttctagtta aaaaaaaaaa aaaaaaa                                  741

<210> SEQ ID NO 46
<211> LENGTH: 97
<212> TYPE: PRT
<213> ORGANISM: Avicennia marina

<400> SEQUENCE: 46

Glu Ile Asn Cys Leu Glu Trp Glu Asn Phe Ala Phe His Pro Ser Pro
 1               5                  10                  15

Leu Ile Val Leu Val Phe Glu Arg Tyr Asn Arg Ala Ser Asp Asn Trp
                20                  25                  30

Lys Ala Leu Lys Glu Leu Glu Lys Ala Ala Glu Val Tyr Trp Lys Ala
            35                  40                  45

Lys Asp Arg Leu Pro Pro Arg Thr Val Lys Ile Asp Ile Asn Ile Glu
        50                  55                  60

Arg Asp Leu Ala Tyr Ala Leu Lys Val Lys Glu Cys Pro Gln Ile Leu
 65                  70                  75                  80

Phe Leu Arg Gly Asn Arg Ile Leu Tyr Arg Glu Lys Gly Ser Pro Phe
                85                  90                  95

Leu

<210> SEQ ID NO 47
<211> LENGTH: 983
<212> TYPE: DNA
<213> ORGANISM: Salsola komarovii
<220> FEATURE:
<221> NAME/KEY: CDS
<222> LOCATION: (1)..(762)

<400> SEQUENCE: 47 atg ttc ctt cat cac cac ttt tca tct tca tct tct tct ttt ctt ctt         48
Met Phe Leu His His His Phe Ser Ser Ser Ser Ser Ser Phe Leu Leu
 1               5                  10                  15 ctc ttc ttc tct ctc cta ata ttc ctt tca tct gct aat ctt tat cat         96
Leu Phe Phe Ser Leu Leu Ile Phe Leu Ser Ser Ala Asn Leu Tyr His
                20                  25                  30 cag aat caa gga tct tgt agt gac ttt gaa tca gaa cca tca atg gct        144
Gln Asn Gln Gly Ser Cys Ser Asp Phe Glu Ser Glu Pro Ser Met Ala
            35                  40                  45 act ctt ggt gga ttg cgc gaa tcc cat ggt gct tct aat gat gct gag        192
Thr Leu Gly Gly Leu Arg Glu Ser His Gly Ala Ser Asn Asp Ala Glu
        50                  55                  60 att gaa acc ctt gct cgc ttt gct gtt gat gaa cac aac aaa aaa gag        240
Ile Glu Thr Leu Ala Arg Phe Ala Val Asp Glu His Asn Lys Lys Glu
 65                  70                  75                  80
```

```
aat gca ttg ttg gag ttt gca agg gtt gta aag gca aag gaa cag gtg      288
Asn Ala Leu Leu Glu Phe Ala Arg Val Val Lys Ala Lys Glu Gln Val
            85                  90                  95 gtt gcg ggt aca ttg cat cac ttc act atc gaa gca att gaa gcg ggc      336
Val Ala Gly Thr Leu His His Phe Thr Ile Glu Ala Ile Glu Ala Gly
        100                 105                 110 aag aag aag ctc tac gaa gcg aag gtg tgg gtg aag cca tgg atg aac      384
Lys Lys Lys Leu Tyr Glu Ala Lys Val Trp Val Lys Pro Trp Met Asn
    115                 120                 125 ttt aag gag ctg cag gaa ttt aag cat gct gat gaa tcc cct tca atc      432
Phe Lys Glu Leu Gln Glu Phe Lys His Ala Asp Glu Ser Pro Ser Ile
130                 135                 140 act cct tcc gac ctc ggc gct aat aga gaa ggg cat tct gga gga tgg      480
Thr Pro Ser Asp Leu Gly Ala Asn Arg Glu Gly His Ser Gly Gly Trp
145                 150                 155                 160 aaa gat gtg cct gtc cat gac cct gaa gtg caa aat gca gca aat cat      528
Lys Asp Val Pro Val His Asp Pro Glu Val Gln Asn Ala Ala Asn His
                165                 170                 175 gct ctt aag acc ttg caa caa aga tcc aac tcc tta ttt cct tat gaa      576
Ala Leu Lys Thr Leu Gln Gln Arg Ser Asn Ser Leu Phe Pro Tyr Glu
            180                 185                 190 ctg cag gaa gtt gct cat gct agg gct gag gtt ctg gaa gac act gcg      624
Leu Gln Glu Val Ala His Ala Arg Ala Glu Val Leu Glu Asp Thr Ala
        195                 200                 205 aag ttt aac ctg cac ctc aag gtg aag aga gga aac aag gat gag ttt      672
Lys Phe Asn Leu His Leu Lys Val Lys Arg Gly Asn Lys Asp Glu Phe
    210                 215                 220 ttc aat gtg gag gtg cac aaa aac agc gaa gga aac tac aac ctt aat      720
Phe Asn Val Glu Val His Lys Asn Ser Glu Gly Asn Tyr Asn Leu Asn
225                 230                 235                 240 cag atg ggg aac gtt gag ccc gag gtt gag aaa agt agt gtt              762
Gln Met Gly Asn Val Glu Pro Glu Val Glu Lys Ser Ser Val
                245                 250 tagactcgtt gagggtgttg taagtactcg ttcgtaactt ttctgatggt caggcaagta    822
tggagtaagg actagactac tagtactagt aagtacagct gacttggttt gagtaaaata    882
acctcgactt tggttgcacc atcatatctt gtatgtttat ggctttgtca atgtattgta    942
agtgaagatt gtttgcttga tctaaaaaaa aaaaaaaaa a                         983

<210> SEQ ID NO 48
<211> LENGTH: 254
<212> TYPE: PRT
<213> ORGANISM: Salsola komarovii

<400> SEQUENCE: 48

Met Phe Leu His His Phe Ser Ser Ser Ser Ser Phe Leu Leu
  1               5                  10                  15

Leu Phe Phe Ser Leu Leu Ile Phe Leu Ser Ser Ala Asn Leu Tyr His
                20                  25                  30

Gln Asn Gln Gly Ser Cys Ser Asp Phe Glu Ser Glu Pro Ser Met Ala
            35                  40                  45

Thr Leu Gly Gly Leu Arg Glu Ser His Gly Ala Ser Asn Asp Ala Glu
        50                  55                  60

Ile Glu Thr Leu Ala Arg Phe Ala Val Asp Glu His Asn Lys Lys Glu
    65                  70                  75                  80

Asn Ala Leu Leu Glu Phe Ala Arg Val Val Lys Ala Lys Glu Gln Val
                85                  90                  95

Val Ala Gly Thr Leu His His Phe Thr Ile Glu Ala Ile Glu Ala Gly
```

```
                       100                 105                 110
     Lys Lys Lys Leu Tyr Glu Ala Lys Val Trp Val Lys Pro Trp Met Asn
             115                 120                 125

Phe Lys Glu Leu Gln Glu Phe Lys His Ala Asp Glu Ser Pro Ser Ile
         130                 135                 140

Thr Pro Ser Asp Leu Gly Ala Asn Arg Glu Gly His Ser Gly Gly Trp
     145                 150                 155                 160

Lys Asp Val Pro Val His Asp Pro Glu Val Gln Asn Ala Ala Asn His
                     165                 170                 175

Ala Leu Lys Thr Leu Gln Gln Arg Ser Asn Ser Leu Phe Pro Tyr Glu
                 180                 185                 190

Leu Gln Glu Val Ala His Ala Arg Ala Glu Val Leu Glu Asp Thr Ala
             195                 200                 205

Lys Phe Asn Leu His Leu Lys Val Lys Arg Gly Asn Lys Asp Glu Phe
         210                 215                 220

Phe Asn Val Glu Val His Lys Asn Ser Glu Gly Asn Tyr Asn Leu Asn
     225                 230                 235                 240

Gln Met Gly Asn Val Glu Pro Glu Val Glu Lys Ser Ser Val
                     245                 250

<210> SEQ ID NO 49
<211> LENGTH: 543
<212> TYPE: DNA
<213> ORGANISM: Salsola komarovii
<220> FEATURE:
<221> NAME/KEY: CDS
<222> LOCATION: (3)..(389)

<400> SEQUENCE: 49 aa aat aag gtt gac tta gct cga gat ttc acc ttc ata gac gac gtc         47
   Asn Lys Val Asp Leu Ala Arg Asp Phe Thr Phe Ile Asp Asp Val
     1               5                  10                  15 gta aag ggg tgc tta ggt tca ctg gat tct tcc ggt aag agt acc ggt         95
Val Lys Gly Cys Leu Gly Ser Leu Asp Ser Ser Gly Lys Ser Thr Gly
                 20                  25                  30 agc ggc ggt aaa aaa cgt ggg ccc gct ccg tac aga atc tac aac ttg        143
Ser Gly Gly Lys Lys Arg Gly Pro Ala Pro Tyr Arg Ile Tyr Asn Leu
             35                  40                  45 ggg aac act caa ccg gtc act gta ccg aca ctt gtc ggt atc cta gag        191
Gly Asn Thr Gln Pro Val Thr Val Pro Thr Leu Val Gly Ile Leu Glu
         50                  55                  60 aag cat ctc aaa gtt aag gcc aag aag aat gtg gtt gag atg ccc gga        239
Lys His Leu Lys Val Lys Ala Lys Lys Asn Val Val Glu Met Pro Gly
 65                  70                  75 aat ggt gac gtg ccc ttc aca cat gcg aat atc tct ttg gcc cga aaa        287
Asn Gly Asp Val Pro Phe Thr His Ala Asn Ile Ser Leu Ala Arg Lys
 80                  85                  90                  95 gat ttc ggg tat aaa ccc act acc gat ttg caa acc ggg ttg aaa aag        335
Asp Phe Gly Tyr Lys Pro Thr Thr Asp Leu Gln Thr Gly Leu Lys Lys
                100                 105                 110 ttt gtt aga tgg tat ctc act tat tac ggc tac aac aac ggc aag cct        383
Phe Val Arg Trp Tyr Leu Thr Tyr Tyr Gly Tyr Asn Asn Gly Lys Pro
            115                 120                 125 gta aat taatatataa atataagtaa tattttttt ctctttttttt ataaattaca          439
Val Asn gaattatttt ttttgggtgg tttatgaatt ttgttggata atatgggat tctttttttc       499 taaatgggaa aataagaat ccaaggaaaa aaaaaaaaaa aaaa                        543
```

```
<210> SEQ ID NO 50
<211> LENGTH: 129
<212> TYPE: PRT
<213> ORGANISM: Salsola komarovii

<400> SEQUENCE: 50

Asn Lys Val Asp Leu Ala Arg Asp Phe Thr Phe Ile Asp Asp Val Val
  1               5                  10                  15

Lys Gly Cys Leu Gly Ser Leu Asp Ser Ser Gly Lys Ser Thr Gly Ser
             20                  25                  30

Gly Gly Lys Lys Arg Gly Pro Ala Pro Tyr Arg Ile Tyr Asn Leu Gly
         35                  40                  45

Asn Thr Gln Pro Val Thr Val Pro Thr Leu Val Gly Ile Leu Glu Lys
     50                  55                  60

His Leu Lys Val Lys Ala Lys Lys Asn Val Val Glu Met Pro Gly Asn
 65                  70                  75                  80

Gly Asp Val Pro Phe Thr His Ala Asn Ile Ser Leu Ala Arg Lys Asp
                 85                  90                  95

Phe Gly Tyr Lys Pro Thr Thr Asp Leu Gln Thr Gly Leu Lys Lys Phe
            100                 105                 110

Val Arg Trp Tyr Leu Thr Tyr Tyr Gly Tyr Asn Asn Gly Lys Pro Val
        115                 120                 125

Asn

<210> SEQ ID NO 51
<211> LENGTH: 1219
<212> TYPE: DNA
<213> ORGANISM: Sueada japonica
<220> FEATURE:
<221> NAME/KEY: CDS
<222> LOCATION: (2)..(871)

<400> SEQUENCE: 51 c aca gga gca aac aaa gga ata gga ctt gaa cta tgc aaa caa cta gct      49
  Thr Gly Ala Asn Lys Gly Ile Gly Leu Glu Leu Cys Lys Gln Leu Ala
    1               5                  10                  15 gct aaa gga gtt gta gta gtt ctc act tct aga gat gga aaa aga ggc        97
Ala Lys Gly Val Val Val Val Leu Thr Ser Arg Asp Gly Lys Arg Gly
             20                  25                  30 tta caa gct cat gaa aat ctc att aaa tct gga att aat cct gaa aat       145
Leu Gln Ala His Glu Asn Leu Ile Lys Ser Gly Ile Asn Pro Glu Asn
         35                  40                  45 ctt cac ttt cat cag ctc gat gtt act gac atc act agt att gct gct       193
Leu His Phe His Gln Leu Asp Val Thr Asp Ile Thr Ser Ile Ala Ala
     50                  55                  60 att gct ggt ttc atc aat tcc aaa ttc ggc aaa ctt gat atc ctg gtg       241
Ile Ala Gly Phe Ile Asn Ser Lys Phe Gly Lys Leu Asp Ile Leu Val
 65                  70                  75                  80 aac aat gct gga att att gga gat atg gtt aac ttt gat gct tta ata       289
Asn Asn Ala Gly Ile Ile Gly Asp Met Val Asn Phe Asp Ala Leu Ile
                 85                  90                  95 gca gca gga ttt ggc act cca aga gaa cag atc aat ctt gag gac agt       337
Ala Ala Gly Phe Gly Thr Pro Arg Glu Gln Ile Asn Leu Glu Asp Ser
            100                 105                 110 ccc ggg aca gta aca cag aca tat gag ctt acg aaa gaa tgc tta caa       385
Pro Gly Thr Val Thr Gln Thr Tyr Glu Leu Thr Lys Glu Cys Leu Gln
        115                 120                 125 aca aat tat tat gga gcg aaa aga acc gtt gaa gct ttg ctt ccg ctt       433
Thr Asn Tyr Tyr Gly Ala Lys Arg Thr Val Glu Ala Leu Leu Pro Leu
```

-continued

```
            130                 135                 140
ctc aag tta tcc gat tct cca agg att gtc aat gtc tcc tct ttt cta     481
Leu Lys Leu Ser Asp Ser Pro Arg Ile Val Asn Val Ser Ser Phe Leu
145                 150                 155                 160 gga agg ttg acg tat ata cca aat gag acg atc aga ggg gtc cta aga     529
Gly Arg Leu Thr Tyr Ile Pro Asn Glu Thr Ile Arg Gly Val Leu Arg
                165                 170                 175 gat gcc gag agc ctt aca gaa gaa cga ata gat gag att ctg aat gac     577
Asp Ala Glu Ser Leu Thr Glu Glu Arg Ile Asp Glu Ile Leu Asn Asp
                180                 185                 190 atg ctg agg gac ttc aaa gac tgt tca ttc aaa gag aag gga tgg cct     625
Met Leu Arg Asp Phe Lys Asp Cys Ser Phe Lys Glu Lys Gly Trp Pro
            195                 200                 205 aaa aat ctg gca gcc tat ata gtt tca aag gcg gcc ttg agt gca tac     673
Lys Asn Leu Ala Ala Tyr Ile Val Ser Lys Ala Ala Leu Ser Ala Tyr
210                 215                 220 aca aga ata ctg gct aag aaa tac cca tca atc atg atc aac tgt att     721
Thr Arg Ile Leu Ala Lys Lys Tyr Pro Ser Ile Met Ile Asn Cys Ile
225                 230                 235                 240 tgc cct ggc ttt gtc aaa act gac atc aat gga aac aca gga cac ttg     769
Cys Pro Gly Phe Val Lys Thr Asp Ile Asn Gly Asn Thr Gly His Leu
                245                 250                 255 ccg gtt gaa gaa ggt gca gcg agt ctg gca agg tta gcg ttg atg ccc     817
Pro Val Glu Glu Gly Ala Ala Ser Leu Ala Arg Leu Ala Leu Met Pro
                260                 265                 270 caa att tta cct tct gga cta ttc ttt cag aga act gaa gtt tct tcg     865
Gln Ile Leu Pro Ser Gly Leu Phe Phe Gln Arg Thr Glu Val Ser Ser
            275                 280                 285 ttt gaa taaaacaatt tgcctattca aaccaacacc acatatctat gaagtttcca     921
Phe Glu
    290 tttgtaggca tctttacgaa aaaaataaga catctgcaat actgttactg gaaaatgcaa     981 tgtactttttt tcatgtatgc atggcgcagt tatttattct gactgcaaca ataagattct    1041 gttctttcaa ggcactctaa ggaatgctga tgtaccgttc tcaaacaagc agacaagtag    1101 acacgtttga ttgtcatgtc ttcattcgta caatcatttt gtgtttgtat gttgagcatg    1161 tttaactaat tacaagagtg taattaagat caacttttat aaaaaaaaaa aaaaaaa      1219
```

<210> SEQ ID NO 52
<211> LENGTH: 290
<212> TYPE: PRT
<213> ORGANISM: Sueada japonica

<400> SEQUENCE: 52

```
Thr Gly Ala Asn Lys Gly Ile Gly Leu Glu Leu Cys Lys Gln Leu Ala
1               5                   10                  15

Ala Lys Gly Val Val Val Leu Thr Ser Arg Asp Gly Lys Arg Gly
            20                  25                  30

Leu Gln Ala His Glu Asn Leu Ile Lys Ser Gly Ile Asn Pro Glu Asn
        35                  40                  45

Leu His Phe His Gln Leu Asp Val Thr Asp Ile Thr Ser Ile Ala Ala
    50                  55                  60

Ile Ala Gly Phe Ile Asn Ser Lys Phe Gly Lys Leu Asp Ile Leu Val
65                  70                  75                  80

Asn Asn Ala Gly Ile Ile Gly Asp Met Val Asn Phe Asp Ala Leu Ile
                85                  90                  95

Ala Ala Gly Phe Gly Thr Pro Arg Glu Gln Ile Asn Leu Glu Asp Ser
```

```
                      100                 105                 110
Pro Gly Thr Val Thr Gln Thr Tyr Glu Leu Thr Lys Glu Cys Leu Gln
            115                 120                 125

Thr Asn Tyr Tyr Gly Ala Lys Arg Thr Val Glu Ala Leu Leu Pro Leu
        130                 135                 140

Leu Lys Leu Ser Asp Ser Pro Arg Ile Val Asn Val Ser Ser Phe Leu
145                 150                 155                 160

Gly Arg Leu Thr Tyr Ile Pro Asn Glu Thr Ile Arg Gly Val Leu Arg
                165                 170                 175

Asp Ala Glu Ser Leu Thr Glu Glu Arg Ile Asp Glu Ile Leu Asn Asp
            180                 185                 190

Met Leu Arg Asp Phe Lys Asp Cys Ser Phe Lys Glu Lys Gly Trp Pro
        195                 200                 205

Lys Asn Leu Ala Ala Tyr Ile Val Ser Lys Ala Ala Leu Ser Ala Tyr
        210                 215                 220

Thr Arg Ile Leu Ala Lys Lys Tyr Pro Ser Ile Met Ile Asn Cys Ile
225                 230                 235                 240

Cys Pro Gly Phe Val Lys Thr Asp Ile Asn Gly Asn Thr Gly His Leu
                245                 250                 255

Pro Val Glu Glu Gly Ala Ala Ser Leu Ala Arg Leu Ala Leu Met Pro
            260                 265                 270

Gln Ile Leu Pro Ser Gly Leu Phe Gln Arg Thr Glu Val Ser Ser
        275                 280                 285

Phe Glu
    290

<210> SEQ ID NO 53
<211> LENGTH: 1148
<212> TYPE: DNA
<213> ORGANISM: Sueada japonica
<220> FEATURE:
<221> NAME/KEY: CDS
<222> LOCATION: (3)..(848)

<400> SEQUENCE: 53 ga agc agg ccg gat atc cat gtt gaa caa gct cat tca gat gat att        47
   Ser Arg Pro Asp Ile His Val Glu Gln Ala His Ser Asp Asp Ile
   1               5                  10                  15 act ggg ttg aaa ttc tca tgt gat ggt cgt cat ctg ttg tct aga agt      95
Thr Gly Leu Lys Phe Ser Cys Asp Gly Arg His Leu Leu Ser Arg Ser
             20                  25                  30 ttt gat tgc aca ctt aag gtt tgg gac ttg cgc caa atg aag cgg tct     143
Phe Asp Cys Thr Leu Lys Val Trp Asp Leu Arg Gln Met Lys Arg Ser
         35                  40                  45 ctt aag gtg ttt gat gaa tta cca aat cac tat gct caa acg aat gtc     191
Leu Lys Val Phe Asp Glu Leu Pro Asn His Tyr Ala Gln Thr Asn Val
     50                  55                  60 tca ttt agt cca gat gag cag ctc atc ttg act ggt aca tct gta gaa     239
Ser Phe Ser Pro Asp Glu Gln Leu Ile Leu Thr Gly Thr Ser Val Glu
65                  70                  75 agg gat agc cca act gga gga ttg ttg tgc ttt tat gat cgg gaa aaa     287
Arg Asp Ser Pro Thr Gly Gly Leu Leu Cys Phe Tyr Asp Arg Glu Lys
80                  85                  90                  95 ctt gaa cta gta tca aaa gtt ggc att tct cct act tgc agt gtt gtg     335
Leu Glu Leu Val Ser Lys Val Gly Ile Ser Pro Thr Cys Ser Val Val
                100                 105                 110 caa tgt gcc tgg cac cca agg ctg aat cag gtt ttt gcc act gct gga     383
Gln Cys Ala Trp His Pro Arg Leu Asn Gln Val Phe Ala Thr Ala Gly
```

```
aat aaa agc caa gga ggt aca cat gta ctc tat gat cca acc atg agt       431
Asn Lys Ser Gln Gly Gly Thr His Val Leu Tyr Asp Pro Thr Met Ser
        130                 135                 140 gag aga ggt gct ctt gtg tgt gtt gct cgt gca cca agg atg aaa tca       479
Glu Arg Gly Ala Leu Val Cys Val Ala Arg Ala Pro Arg Met Lys Ser
145                 150                 155 gtg gat gat ttt gag gtg cag ccg gtt ata cat aac cct cac gca ctt       527
Val Asp Asp Phe Glu Val Gln Pro Val Ile His Asn Pro His Ala Leu
160                 165                 170                 175 ccc ttg ttc aga gat cag cca agc cgc aaa cgt caa aga gag aag att       575
Pro Leu Phe Arg Asp Gln Pro Ser Arg Lys Arg Gln Arg Glu Lys Ile
                180                 185                 190 ctg aag gac cca ata aaa tcc cac aaa cca gag ctt cct atg tca gga       623
Leu Lys Asp Pro Ile Lys Ser His Lys Pro Glu Leu Pro Met Ser Gly
                195                 200                 205 cct ggc cat ggt ggc aga act ggt aca tca tcg ggt agt ttg tta aca       671
Pro Gly His Gly Gly Arg Thr Gly Thr Ser Ser Gly Ser Leu Leu Thr
        210                 215                 220 caa tat ctc ctc aag caa ggg ggc atg ttg aaa gag aca tgg atg gat       719
Gln Tyr Leu Leu Lys Gln Gly Gly Met Leu Lys Glu Thr Trp Met Asp
225                 230                 235 gaa gat ccc aga gaa gct att ctc aag tat gct gat gct gca gaa aag       767
Glu Asp Pro Arg Glu Ala Ile Leu Lys Tyr Ala Asp Ala Ala Glu Lys
240                 245                 250                 255 gat cca aag ttt att gcc ccg gct tat gct gag act cag ccc aag cca       815
Asp Pro Lys Phe Ile Ala Pro Ala Tyr Ala Glu Thr Gln Pro Lys Pro
                260                 265                 270 gtc ttt gag gat tct gat aag gaa gat gaa gaa taattcatct tttgcagtgg     868
Val Phe Glu Asp Ser Asp Lys Glu Asp Glu Glu
                275                 280 ttggattaat ttaatttgag aatattatac tgtgtatatt aatagccaat ttttcaggcg     928
aatgatatgc ttctcacatt acatgctgag ttttatttgc tgctacagat tgtagatgaa     988
taggttaatg taaacacaag catagagatt agaatataga aatgattctg tatccaaaac    1048 acaatttat caccagatgg tatcaaaagc tgtattgact gttgagtaat gtcattaacc    1108
actttcactc cccaaaaaaa aaaaaaaaaa aaaaaaaaa                            1148
```

<210> SEQ ID NO 54
<211> LENGTH: 282
<212> TYPE: PRT
<213> ORGANISM: Sueada japonica

<400> SEQUENCE: 54

Ser Arg Pro Asp Ile His Val Glu Gln Ala His Ser Asp Asp Ile Thr
1               5                   10                  15

Gly Leu Lys Phe Ser Cys Asp Gly Arg His Leu Leu Ser Arg Ser Phe
                20                  25                  30

Asp Cys Thr Leu Lys Val Trp Asp Leu Arg Gln Met Lys Arg Ser Leu
            35                  40                  45

Lys Val Phe Asp Glu Leu Pro Asn His Tyr Ala Gln Thr Asn Val Ser
        50                  55                  60

Phe Ser Pro Asp Glu Gln Leu Ile Leu Thr Gly Thr Ser Val Glu Arg
65                  70                  75                  80

Asp Ser Pro Thr Gly Gly Leu Leu Cys Phe Tyr Asp Arg Glu Lys Leu
                85                  90                  95

Glu Leu Val Ser Lys Val Gly Ile Ser Pro Thr Cys Ser Val Val Gln

```
                    100                 105                 110
Cys Ala Trp His Pro Arg Leu Asn Gln Val Phe Ala Thr Ala Gly Asn
        115                 120                 125
Lys Ser Gln Gly Gly Thr His Val Leu Tyr Asp Pro Thr Met Ser Glu
    130                 135                 140
Arg Gly Ala Leu Val Cys Val Ala Arg Ala Pro Arg Met Lys Ser Val
145                 150                 155                 160
Asp Asp Phe Glu Val Gln Pro Val Ile His Asn Pro His Ala Leu Pro
                165                 170                 175
Leu Phe Arg Asp Gln Pro Ser Arg Lys Arg Gln Arg Glu Lys Ile Leu
            180                 185                 190
Lys Asp Pro Ile Lys Ser His Lys Pro Glu Leu Pro Met Ser Gly Pro
        195                 200                 205
Gly His Gly Gly Arg Thr Gly Thr Ser Ser Gly Ser Leu Leu Thr Gln
    210                 215                 220
Tyr Leu Leu Lys Gln Gly Gly Met Leu Lys Glu Thr Trp Met Asp Glu
225                 230                 235                 240
Asp Pro Arg Glu Ala Ile Leu Lys Tyr Ala Asp Ala Ala Glu Lys Asp
                245                 250                 255
Pro Lys Phe Ile Ala Pro Ala Tyr Ala Glu Thr Gln Pro Lys Pro Val
            260                 265                 270
Phe Glu Asp Ser Asp Lys Glu Asp Glu Glu
        275                 280

<210> SEQ ID NO 55
<211> LENGTH: 1193
<212> TYPE: DNA
<213> ORGANISM: Avicennia marina
<220> FEATURE:
<221> NAME/KEY: CDS
<222> LOCATION: (3)..(815)

<400> SEQUENCE: 55 gt gca cct gag tta ctt ctt gga gca aag cat tat aca agt gct gtt        47
   Ala Pro Glu Leu Leu Leu Gly Ala Lys His Tyr Thr Ser Ala Val
    1               5                  10                  15 gac atg tgg gct gtg ggc tgc att ttt gct gag ctt ctg act cta aag     95
Asp Met Trp Ala Val Gly Cys Ile Phe Ala Glu Leu Leu Thr Leu Lys
            20                  25                  30 cca cta ttt caa ggg caa gaa gta aaa ggg act tct aat cca ttt cag    143
Pro Leu Phe Gln Gly Gln Glu Val Lys Gly Thr Ser Asn Pro Phe Gln
        35                  40                  45 ctt gat caa ctt gac aaa atc ttt aag gtc cta ggt cat ccc acg caa    191
Leu Asp Gln Leu Asp Lys Ile Phe Lys Val Leu Gly His Pro Thr Gln
    50                  55                  60 gaa aag tgg ccc aca cta gcg aat ctt cca cat tgg cag tct gat gtg    239
Glu Lys Trp Pro Thr Leu Ala Asn Leu Pro His Trp Gln Ser Asp Val
65                  70                  75 caa cgt atc caa ggg ctc aaa tac gac aat act gga ctt tac aat gtt    287
Gln Arg Ile Gln Gly Leu Lys Tyr Asp Asn Thr Gly Leu Tyr Asn Val
            80                  85                  90                  95 gtt cat ctc tcc ccc aaa aat cca gca tat gac ctt ctc tca aag atg    335
Val His Leu Ser Pro Lys Asn Pro Ala Tyr Asp Leu Leu Ser Lys Met
                    100                 105                 110 ctt gag tat gat cct aga aaa aga ata aca gct aca caa gct ctt gag    383
Leu Glu Tyr Asp Pro Arg Lys Arg Ile Thr Ala Thr Gln Ala Leu Glu
                115                 120                 125 cat gag tat ttt cgc atg gaa cct ttg ccg gga cgc aac gct ctg gta    431
```

-continued

```
His Glu Tyr Phe Arg Met Glu Pro Leu Pro Gly Arg Asn Ala Leu Val
        130                 135                 140 cca cca cag cct ggg gag aaa att gtg aac tac cca aca cga cca gtg      479
Pro Pro Gln Pro Gly Glu Lys Ile Val Asn Tyr Pro Thr Arg Pro Val
145                 150                 155 gac aca aat act gat att gaa gga aca atc agc ctc cag ccc tct caa      527
Asp Thr Asn Thr Asp Ile Glu Gly Thr Ile Ser Leu Gln Pro Ser Gln
160                 165                 170                 175 ccg gta tca tct ggg aat tct gtg tct ggg gcc cta gcc ggt cct cat      575
Pro Val Ser Ser Gly Asn Ser Val Ser Gly Ala Leu Ala Gly Pro His
                180                 185                 190 gta atg caa aat aga tcc atg cct cgg cca atg ccc atg gtt ggc gtg      623
Val Met Gln Asn Arg Ser Met Pro Arg Pro Met Pro Met Val Gly Val
            195                 200                 205 caa cgc atg caa cct cca ggg atc cca cac tat ggt ctt gct tct cag      671
Gln Arg Met Gln Pro Pro Gly Ile Pro His Tyr Gly Leu Ala Ser Gln
        210                 215                 220 gca gga atg ggt gga gta aat cct ggt ggc atc cca att cag cgg gga      719
Ala Gly Met Gly Gly Val Asn Pro Gly Gly Ile Pro Ile Gln Arg Gly
225                 230                 235 gtt cct gct cag gct cat caa cag cag cag atg aga agg aaa gac cct      767
Val Pro Ala Gln Ala His Gln Gln Gln Gln Met Arg Arg Lys Asp Pro
240                 245                 250                 255 gga atg ggg atg act gga tat cct cca caa cag aaa tca agg cgc ttt      815
Gly Met Gly Met Thr Gly Tyr Pro Pro Gln Gln Lys Ser Arg Arg Phe
                260                 265                 270 tgagagtccg ggtggatttg gagcctaagt gggaggacaa atacacattc caatcaaatt      875
agaggaaacc ttaaattaat cttccagtca gctgaaacga caccagtgga accaaatgat      935
ctgaccccat ttccaggatt gcatgtattt attaggagga atacacgaat gaagattcga      995
gtctagtgcc aaattattct aacataccct catcatttgt tcctactaca ttccgacgtt     1055
atatgtttca actagtggaa gggtttctgc agtccaccca tgtggcacaa acatgattca     1115
tagcatgcca agcaacactt tactggtgtg taccaaggca atttctctat ttccaagcca     1175
aaaaaaaaaa aaaaaaaa                                                   1193

<210> SEQ ID NO 56
<211> LENGTH: 271
<212> TYPE: PRT
<213> ORGANISM: Avicennia marina

<400> SEQUENCE: 56

Ala Pro Glu Leu Leu Leu Gly Ala Lys His Tyr Thr Ser Ala Val Asp
  1               5                  10                  15

Met Trp Ala Val Gly Cys Ile Phe Ala Glu Leu Leu Thr Leu Lys Pro
             20                  25                  30

Leu Phe Gln Gly Gln Glu Val Lys Gly Thr Ser Asn Pro Phe Gln Leu
         35                  40                  45

Asp Gln Leu Asp Lys Ile Phe Lys Val Leu Gly His Pro Thr Gln Glu
     50                  55                  60

Lys Trp Pro Thr Leu Ala Asn Leu Pro His Trp Gln Ser Asp Val Gln
 65                  70                  75                  80

Arg Ile Gln Gly Leu Lys Tyr Asp Asn Thr Gly Leu Tyr Asn Val Val
                 85                  90                  95

His Leu Ser Pro Lys Asn Pro Ala Tyr Asp Leu Leu Ser Lys Met Leu
            100                 105                 110

Glu Tyr Asp Pro Arg Lys Arg Ile Thr Ala Thr Gln Ala Leu Glu His
```

-continued

```
                 115                 120                 125
Glu Tyr Phe Arg Met Glu Pro Leu Pro Gly Arg Asn Ala Leu Val Pro
    130                 135                 140

Pro Gln Pro Gly Glu Lys Ile Val Asn Tyr Pro Thr Arg Pro Val Asp
145                 150                 155                 160

Thr Asn Thr Asp Ile Glu Gly Thr Ile Ser Leu Gln Pro Ser Gln Pro
                165                 170                 175

Val Ser Ser Gly Asn Ser Val Ser Gly Ala Leu Ala Gly Pro His Val
            180                 185                 190

Met Gln Asn Arg Ser Met Pro Arg Pro Met Pro Met Val Gly Val Gln
        195                 200                 205

Arg Met Gln Pro Pro Gly Ile Pro His Tyr Gly Leu Ala Ser Gln Ala
    210                 215                 220

Gly Met Gly Gly Val Asn Pro Gly Gly Ile Pro Ile Gln Arg Gly Val
225                 230                 235                 240

Pro Ala Gln Ala His Gln Gln Gln Met Arg Arg Lys Asp Pro Gly
                245                 250                 255

Met Gly Met Thr Gly Tyr Pro Pro Gln Gln Lys Ser Arg Arg Phe
            260                 265                 270

<210> SEQ ID NO 57
<211> LENGTH: 1195
<212> TYPE: DNA
<213> ORGANISM: Sueada japonica
<220> FEATURE:
<221> NAME/KEY: CDS
<222> LOCATION: (116)..(1195)

<400> SEQUENCE: 57
gcaaaagtaa gagtgaaaga acacaaacca actttctatt ttcagctcaa atcaaattca      60
atagtggcaa acaatagag ggcaaattct cattgcccaa ttcaaatttg gtaaa atg      118
                                                             Met
                                                              1 gct caa aag cat ttg aaa gaa ctt ctc aaa gaa gat caa gaa ccc ttt      166
Ala Gln Lys His Leu Lys Glu Leu Leu Lys Glu Asp Gln Glu Pro Phe
            5                  10                  15 cat tta aag gat tac att gca act aaa aaa tgt caa ctt ttg aag aag      214
His Leu Lys Asp Tyr Ile Ala Thr Lys Lys Cys Gln Leu Leu Lys Lys
        20                  25                  30 caa gaa tta gta gta ccc aaa tca aaa ctt caa ctc aaa aag cca aag      262
Gln Glu Leu Val Val Pro Lys Ser Lys Leu Gln Leu Lys Lys Pro Lys
    35                  40                  45 cca aaa cca att tca aaa agc act tca gtt ttg tgc aaa aat gct tgc      310
Pro Lys Pro Ile Ser Lys Ser Thr Ser Val Leu Cys Lys Asn Ala Cys
50                  55                  60                  65 ttt tta tct tta caa gaa tcc cct gac ctc aga aaa tcc ccc aaa cta      358
Phe Leu Ser Leu Gln Glu Ser Pro Asp Leu Arg Lys Ser Pro Lys Leu
                70                  75                  80 ttt gat ttt cca cct tcc cct gtt tct aac aaa agc cca aac aga gta      406
Phe Asp Phe Pro Pro Ser Pro Val Ser Asn Lys Ser Pro Asn Arg Val
            85                  90                  95 ttc ctc aat gtt cct gct aaa act gct gct ctt ctt ctt gaa gct gct      454
Phe Leu Asn Val Pro Ala Lys Thr Ala Ala Leu Leu Leu Glu Ala Ala
        100                 105                 110 att cga att caa acc cac aaa tct aaa ccc aaa acc cag att aaa aat      502
Ile Arg Ile Gln Thr His Lys Ser Lys Pro Lys Thr Gln Ile Lys Asn
    115                 120                 125 tcg ggt ttt ggg cta ttc ggg tca atg tta aag cga tta aat ctt cga      550
```

```
Ser Gly Phe Gly Leu Phe Gly Ser Met Leu Lys Arg Leu Asn Leu Arg
130                 135                 140                 145 aat cgt acc caa aaa atc aag tca aaa aca gag gaa caa aac aga gga     598
Asn Arg Thr Gln Lys Ile Lys Ser Lys Thr Glu Glu Gln Asn Arg Gly
                150                 155                 160 tgc tct gtt ttg agg agt gtt gaa gaa gaa aaa act acc acc att tct     646
Cys Ser Val Leu Arg Ser Val Glu Glu Glu Lys Thr Thr Thr Ile Ser
            165                 170                 175 tct tct tca tct tca tct tct tca aca tca tcg tat tct tcg tgt tct     694
Ser Ser Ser Ser Ser Ser Ser Ser Thr Ser Ser Tyr Ser Ser Cys Ser
        180                 185                 190 tgc aat gag agg tta agt agt ttg gat ttg gag agt tct agc agt gga     742
Cys Asn Glu Arg Leu Ser Ser Leu Asp Leu Glu Ser Ser Ser Ser Gly
    195                 200                 205 aga tca tta cat gat gaa gat gaa gat gaa gat gaa gat gat gaa ttt     790
Arg Ser Leu His Asp Glu Asp Glu Asp Glu Asp Glu Asp Asp Glu Phe
210                 215                 220                 225 gag ttt aca aat gtt tta aga gaa aat aat aat gat gat aaa aat gga     838
Glu Phe Thr Asn Val Leu Arg Glu Asn Asn Asn Asp Asp Lys Asn Gly
                230                 235                 240 ggt tat tat tca gga att tgc tta agt cct ttg agt cca ttt cgt ttt     886
Gly Tyr Tyr Ser Gly Ile Cys Leu Ser Pro Leu Ser Pro Phe Arg Phe
            245                 250                 255 gct ctt cat aaa aac tct tct cct gaa cgt tgc tct cct gct aaa tcc     934
Ala Leu His Lys Asn Ser Ser Pro Glu Arg Cys Ser Pro Ala Lys Ser
        260                 265                 270 cct gtt cgt tgc aaa ttt gag ggt aat gct aaa tat gaa caa gaa agc     982
Pro Val Arg Cys Lys Phe Glu Gly Asn Ala Lys Tyr Glu Gln Glu Ser
    275                 280                 285 tta ata aag ttt gaa gac gaa gat gaa gaa gac aaa gag caa aat agc    1030
Leu Ile Lys Phe Glu Asp Glu Asp Glu Glu Asp Lys Glu Gln Asn Ser
290                 295                 300                 305 cct gtt tcc gtg ctc gat cct cca ttc gag gat gat tac gat ggg cat    1078
Pro Val Ser Val Leu Asp Pro Pro Phe Glu Asp Asp Tyr Asp Gly His
                310                 315                 320 gag gag gat agc tac gag gac atc gaa tgc agc tat gct ttt gta caa    1126
Glu Glu Asp Ser Tyr Glu Asp Ile Glu Cys Ser Tyr Ala Phe Val Gln
            325                 330                 335 aga gca caa caa gag tta ttg cac aga ctt cac cgg ttc cag aag cta    1174
Arg Ala Gln Gln Glu Leu Leu His Arg Leu His Arg Phe Gln Lys Leu
        340                 345                 350 gcg gag ttg gac cca att gaa                                         1195
Ala Glu Leu Asp Pro Ile Glu
    355                 360

<210> SEQ ID NO 58
<211> LENGTH: 360
<212> TYPE: PRT
<213> ORGANISM: Sueada japonica

<400> SEQUENCE: 58

Met Ala Gln Lys His Leu Lys Glu Leu Leu Lys Glu Asp Gln Glu Pro
1               5                   10                  15

Phe His Leu Lys Asp Tyr Ile Ala Thr Lys Cys Gln Leu Leu Lys
            20                  25                  30

Lys Gln Glu Leu Val Val Pro Lys Ser Lys Leu Gln Leu Lys Lys Pro
        35                  40                  45

Lys Pro Lys Pro Ile Ser Lys Ser Thr Ser Val Leu Cys Lys Asn Ala
    50                  55                  60
```

```
Cys Phe Leu Ser Leu Gln Glu Ser Pro Asp Leu Arg Lys Ser Pro Lys
 65                  70                  75                  80

Leu Phe Asp Phe Pro Pro Ser Pro Val Ser Asn Lys Ser Pro Asn Arg
                 85                  90                  95

Val Phe Leu Asn Val Pro Ala Lys Thr Ala Ala Leu Leu Leu Glu Ala
            100                 105                 110

Ala Ile Arg Ile Gln Thr His Lys Ser Lys Pro Lys Thr Gln Ile Lys
        115                 120                 125

Asn Ser Gly Phe Gly Leu Phe Gly Ser Met Leu Lys Arg Leu Asn Leu
    130                 135                 140

Arg Asn Arg Thr Gln Lys Ile Lys Ser Lys Thr Glu Glu Gln Asn Arg
145                 150                 155                 160

Gly Cys Ser Val Leu Arg Ser Val Glu Glu Lys Thr Thr Thr Ile
                165                 170                 175

Ser Ser Ser Ser Ser Ser Ser Ser Thr Ser Ser Tyr Ser Ser Cys
            180                 185                 190

Ser Cys Asn Glu Arg Leu Ser Ser Leu Asp Leu Glu Ser Ser Ser Ser
        195                 200                 205

Gly Arg Ser Leu His Asp Glu Asp Glu Asp Glu Asp Asp Glu
    210                 215                 220

Phe Glu Phe Thr Asn Val Leu Arg Glu Asn Asn Asn Asp Asp Lys Asn
225                 230                 235                 240

Gly Gly Tyr Tyr Ser Gly Ile Cys Leu Ser Pro Leu Ser Pro Phe Arg
                245                 250                 255

Phe Ala Leu His Lys Asn Ser Ser Pro Glu Arg Cys Ser Pro Ala Lys
            260                 265                 270

Ser Pro Val Arg Cys Lys Phe Glu Gly Asn Ala Lys Tyr Glu Gln Glu
        275                 280                 285

Ser Leu Ile Lys Phe Glu Asp Glu Glu Asp Lys Glu Gln Asn
    290                 295                 300

Ser Pro Val Ser Val Leu Asp Pro Pro Phe Glu Asp Tyr Asp Gly
305                 310                 315                 320

His Glu Glu Asp Ser Tyr Glu Asp Ile Glu Cys Ser Tyr Ala Phe Val
                325                 330                 335

Gln Arg Ala Gln Gln Glu Leu Leu His Arg Leu His Arg Phe Gln Lys
            340                 345                 350

Leu Ala Glu Leu Asp Pro Ile Glu
        355                 360

<210> SEQ ID NO 59
<211> LENGTH: 1301
<212> TYPE: DNA
<213> ORGANISM: Salsola komarovii
<220> FEATURE:
<221> NAME/KEY: CDS
<222> LOCATION: (3)..(815)

<400> SEQUENCE: 59 gt gag gtt gac gat agc gtt aat agt cta cag gca gat gtt gac aac     47
   Glu Val Asp Asp Ser Val Asn Ser Leu Gln Ala Asp Val Asp Asn
     1               5                  10                  15 ctt tca att gag gaa cgc aga ttg gat gaa cag ata agg gaa atg caa     95
Leu Ser Ile Glu Glu Arg Arg Leu Asp Glu Gln Ile Arg Glu Met Gln
                 20                  25                  30 gaa aga ttg agg gaa atg agt gaa gat gat atc aat cag aag tgg ctt    143
Glu Arg Leu Arg Glu Met Ser Glu Asp Asp Ile Asn Gln Lys Trp Leu
             35                  40                  45
```

```
ttt gta act gaa gaa gac ata aag ggt tta cct tgt ttt cag aat gaa        191
Phe Val Thr Glu Glu Asp Ile Lys Gly Leu Pro Cys Phe Gln Asn Glu
         50                  55                  60 acc tta att gca att aaa gct cca cat gga aca act ttg gag gtt cca        239
Thr Leu Ile Ala Ile Lys Ala Pro His Gly Thr Thr Leu Glu Val Pro
 65                  70                  75 gat cca gat gag gct gtc gat tat cct caa aga aga tac aag ata gtt        287
Asp Pro Asp Glu Ala Val Asp Tyr Pro Gln Arg Arg Tyr Lys Ile Val
 80                  85                  90                  95 ctt agg agc aca atg ggt cct att gat gta tat tta gtc agt caa ttt        335
Leu Arg Ser Thr Met Gly Pro Ile Asp Val Tyr Leu Val Ser Gln Phe
                100                 105                 110 gaa gag aag ttt gag gag atc agt ggt gct gac ggt cca cta agt ata        383
Glu Glu Lys Phe Glu Glu Ile Ser Gly Ala Asp Gly Pro Leu Ser Ile
            115                 120                 125 cca agt acc tca ggt gat gac aaa cac aca act gtt gca gct aag gaa        431
Pro Ser Thr Ser Gly Asp Asp Lys His Thr Thr Val Ala Ala Lys Glu
        130                 135                 140 gaa agc aat ggc aat gag att gaa ata gaa gga caa ggg acc cat aga        479
Glu Ser Asn Gly Asn Glu Ile Glu Ile Glu Gly Gln Gly Thr His Arg
145                 150                 155 atc tgc tca gat tcc aac gct cag caa gac ttt gtg agt gga att atg        527
Ile Cys Ser Asp Ser Asn Ala Gln Gln Asp Phe Val Ser Gly Ile Met
160                 165                 170                 175 aag ata gtg cct gaa gtt gat agt gat gca gat tac tgg ttg cta tcg        575
Lys Ile Val Pro Glu Val Asp Ser Asp Ala Asp Tyr Trp Leu Leu Ser
                180                 185                 190 gat gct gat gtt agc att act gac atg tgg gga act gat tct gga gtt        623
Asp Ala Asp Val Ser Ile Thr Asp Met Trp Gly Thr Asp Ser Gly Val
            195                 200                 205 gaa tgg aat gaa tta ggg act ata cat gaa gac tat gcc gtg gct aat        671
Glu Trp Asn Glu Leu Gly Thr Ile His Glu Asp Tyr Ala Val Ala Asn
        210                 215                 220 gtt ggc act tca cag cca caa agt cca cca aca agt gca aca gaa gtg        719
Val Gly Thr Ser Gln Pro Gln Ser Pro Pro Thr Ser Ala Thr Glu Val
225                 230                 235 ctt cca gct aac atg aca agc agg aga ttg aca tgg agt ttt gag aga        767
Leu Pro Ala Asn Met Thr Ser Arg Arg Leu Thr Trp Ser Phe Glu Arg
240                 245                 250                 255 att gcc aar att cat tca aat ggt cac tat tgc ttg gaa gtg agg ctc        815
Ile Ala Lys Ile His Ser Asn Gly His Tyr Cys Leu Glu Val Arg Leu
                260                 265                 270 taactttcta ttattcatcc tgggatttgg gtacgaaagt ctgccttgaa gatgctgtaa     875
catgttgtgt attacaactg tgtgaatcta gtaagttggt agggtgagat tgttcctgat     935
cttattgcac agccggttgg gagagattga tcgctcaaca actgacaaaa ttggggcatg     995
ttaacggata gtatgcagtt gtaattttgt acatcacatt tgttgatttt agtcagtaca    1055
tcataactag ctcttcctat acttcttcaa ttgtcaactg gaatagattt ttagattaat    1115
tagatctctc tttgtatgga aatgtttcag ggtaacaagc cagaaattaa aatggtttta    1175
tgtgtaaaaa tatatactta aattgtttgt aggaagtttc tgatgggttg ttggatggct    1235
tttaacaact acatcgtata aggaaattcg tatcacaaat tcacaatgaa aaaaaaaaa    1295 aaaaaa                                                               1301

<210> SEQ ID NO 60
<211> LENGTH: 271
<212> TYPE: PRT
```

<213> ORGANISM: Salsola komarovii

<400> SEQUENCE: 60

```
Glu Val Asp Asp Ser Val Asn Ser Leu Gln Ala Asp Val Asp Asn Leu
1               5                   10                  15

Ser Ile Glu Glu Arg Arg Leu Asp Glu Gln Ile Arg Glu Met Gln Glu
            20                  25                  30

Arg Leu Arg Glu Met Ser Glu Asp Asp Ile Asn Gln Lys Trp Leu Phe
        35                  40                  45

Val Thr Glu Glu Asp Ile Lys Gly Leu Pro Cys Phe Gln Asn Glu Thr
    50                  55                  60

Leu Ile Ala Ile Lys Ala Pro His Gly Thr Thr Leu Glu Val Pro Asp
65                  70                  75                  80

Pro Asp Glu Ala Val Asp Tyr Pro Gln Arg Arg Tyr Lys Ile Val Leu
                85                  90                  95

Arg Ser Thr Met Gly Pro Ile Asp Val Tyr Leu Val Ser Gln Phe Glu
            100                 105                 110

Glu Lys Phe Glu Glu Ile Ser Gly Ala Asp Gly Pro Leu Ser Ile Pro
        115                 120                 125

Ser Thr Ser Gly Asp Asp Lys His Thr Thr Val Ala Ala Lys Glu Glu
130                 135                 140

Ser Asn Gly Asn Glu Ile Glu Ile Glu Gly Gln Gly Thr His Arg Ile
145                 150                 155                 160

Cys Ser Asp Ser Asn Ala Gln Gln Asp Phe Val Ser Gly Ile Met Lys
                165                 170                 175

Ile Val Pro Glu Val Asp Ser Asp Ala Asp Tyr Trp Leu Leu Ser Asp
            180                 185                 190

Ala Asp Val Ser Ile Thr Asp Met Trp Gly Thr Asp Ser Gly Val Glu
        195                 200                 205

Trp Asn Glu Leu Gly Thr Ile His Glu Asp Tyr Ala Val Ala Asn Val
210                 215                 220

Gly Thr Ser Gln Pro Gln Ser Pro Pro Thr Ser Ala Thr Glu Val Leu
225                 230                 235                 240

Pro Ala Asn Met Thr Ser Arg Arg Leu Thr Trp Ser Phe Glu Arg Ile
                245                 250                 255

Ala Lys Ile His Ser Asn Gly His Tyr Cys Leu Glu Val Arg Leu
            260                 265                 270
```

<210> SEQ ID NO 61
<211> LENGTH: 1032
<212> TYPE: DNA
<213> ORGANISM: Salsola komarovii
<220> FEATURE:
<221> NAME/KEY: CDS
<222> LOCATION: (1)..(732)

<400> SEQUENCE: 61

```
cca caa cga aga ccc gac ccg gtc ccg aac ctt cac ggt cag ctt ttt    48
Pro Gln Arg Arg Pro Asp Pro Val Pro Asn Leu His Gly Gln Leu Phe
1               5                   10                  15 caa cac cga aat cca cac cac cgt gac ctc cac ccc tgc cgt agc ccg    96
Gln His Arg Asn Pro His His Arg Asp Leu His Pro Cys Arg Ser Pro
            20                  25                  30 gca atg ggt cca ctc cct ccg cag act cat ctg cgc tgg tat tcc ctc   144
Ala Met Gly Pro Leu Pro Pro Gln Thr His Leu Arg Trp Tyr Ser Leu
        35                  40                  45 tcg cgc tac tcc ccc gtg atc ggc ctc ggc gtc caa tgg aag ccc tcc   192
```

```
                                                                                    -continued Ser Arg Tyr Ser Pro Val Ile Gly Leu Gly Val Gln Trp Lys Pro Ser
 50                  55                  60 tcc acc tca gct gcc act ctt caa ctc agc atc gac aaa aag tgc ctc     240
Ser Thr Ser Ala Ala Thr Leu Gln Leu Ser Ile Asp Lys Lys Cys Leu
 65                  70                  75                  80 atc ttc caa ctc tcc cac tcc ccc gcc atc ccc gcc acc ctc cgc gac     288
Ile Phe Gln Leu Ser His Ser Pro Ala Ile Pro Ala Thr Leu Arg Asp
                 85                  90                  95 ctc ctc ctc gac gat cgc gtc acc ttc ttt ggt gtc cac aac ggc cgt     336
Leu Leu Leu Asp Asp Arg Val Thr Phe Phe Gly Val His Asn Gly Arg
            100                 105                 110 gcc cgc gac ctc ctc caa ggg tcc cac cat gag ctc gac gtc aac aat     384
Ala Arg Asp Leu Leu Gln Gly Ser His His Glu Leu Asp Val Asn Asn
        115                 120                 125 ctg gtt gat ctt gcc gag gag gaa aat ggt cat tac ttg aag tgg tcc     432
Leu Val Asp Leu Ala Glu Glu Glu Asn Gly His Tyr Leu Lys Trp Ser
    130                 135                 140 atg gaa gac atg gct gaa gat gtg ttg ggc ttt tgt ggg gta cac aaa     480
Met Glu Asp Met Ala Glu Asp Val Leu Gly Phe Cys Gly Val His Lys
145                 150                 155                 160 ccc agg aag gtt atg tta agt ggt tgg gat cag tat tgc ttg tct aat     528
Pro Arg Lys Val Met Leu Ser Gly Trp Asp Gln Tyr Cys Leu Ser Asn
                165                 170                 175 gac cag gtt cag tat gct tgt gtt gat gct tac gtt tct ctt cgt ctt     576
Asp Gln Val Gln Tyr Ala Cys Val Asp Ala Tyr Val Ser Leu Arg Leu
            180                 185                 190 gct cga gct tat ggg tac cac cgt ctc gat cac gat gat gat tat gat     624
Ala Arg Ala Tyr Gly Tyr His Arg Leu Asp His Asp Asp Asp Tyr Asp
        195                 200                 205 gac cat gac gac gat gat aac gac cac acc gat gat gat tac gat gac     672
Asp His Asp Asp Asp Asp Asn Asp His Thr Asp Asp Asp Tyr Asp Asp
    210                 215                 220 gtt tac gac cgc aat ata ggc tct gat gat gat ggt tat gat gcc gat     720
Val Tyr Asp Arg Asn Ile Gly Ser Asp Asp Asp Gly Tyr Asp Ala Asp
225                 230                 235                 240 gat gat cga cga tgatcaattt ggactagact tcgttattgg aagggtccga         772
Asp Asp Arg Arg tcatcatgcc agtctaatta caaagagaca agaaataaaa atgatgatca aaaaagaag    832 tcaatccata tacgtaattt tcattgcaat atcaattttg aggtgtttta ttattggcct   892
gtaataatag ttttatttaa taatagcact atagatctca tcctaacctt tacttattgg   952
gcttatgcgc tgtatgtcca ataaccaagt ttaatttatt tcatgatctg atgattactg  1012
caaaaaaaaa aaaaaaaaa                                               1032

<210> SEQ ID NO 62
<211> LENGTH: 244
<212> TYPE: PRT
<213> ORGANISM: Salsola komarovii

<400> SEQUENCE: 62

Pro Gln Arg Arg Pro Asp Pro Val Pro Asn Leu His Gly Gln Leu Phe
 1                   5                  10                  15

Gln His Arg Asn Pro His His Arg Asp Leu His Pro Cys Arg Ser Pro
                20                  25                  30

Ala Met Gly Pro Leu Pro Pro Gln Thr His Leu Arg Trp Tyr Ser Leu
            35                  40                  45

Ser Arg Tyr Ser Pro Val Ile Gly Leu Gly Val Gln Trp Lys Pro Ser
 50                  55                  60
```

```
Ser Thr Ser Ala Ala Thr Leu Gln Leu Ser Ile Asp Lys Lys Cys Leu
 65                  70                  75                  80

Ile Phe Gln Leu Ser His Ser Pro Ala Ile Pro Ala Thr Leu Arg Asp
                 85                  90                  95

Leu Leu Leu Asp Asp Arg Val Thr Phe Phe Gly Val His Asn Gly Arg
            100                 105                 110

Ala Arg Asp Leu Leu Gln Gly Ser His His Glu Leu Asp Val Asn Asn
        115                 120                 125

Leu Val Asp Leu Ala Glu Glu Asn Gly His Tyr Leu Lys Trp Ser
    130                 135                 140

Met Glu Asp Met Ala Glu Asp Val Leu Gly Phe Cys Gly Val His Lys
145                 150                 155                 160

Pro Arg Lys Val Met Leu Ser Gly Trp Asp Gln Tyr Cys Leu Ser Asn
                165                 170                 175

Asp Gln Val Gln Tyr Ala Cys Val Asp Ala Tyr Val Ser Leu Arg Leu
            180                 185                 190

Ala Arg Ala Tyr Gly Tyr His Arg Leu Asp His Asp Asp Tyr Asp
        195                 200                 205

Asp His Asp Asp Asp Asn Asp His Thr Asp Asp Tyr Asp Asp
    210                 215                 220

Val Tyr Asp Arg Asn Ile Gly Ser Asp Asp Gly Tyr Asp Ala Asp
225                 230                 235                 240

Asp Asp Arg Arg

<210> SEQ ID NO 63
<211> LENGTH: 1029
<212> TYPE: DNA
<213> ORGANISM: Mesembryanthemum crystallinum
<220> FEATURE:
<221> NAME/KEY: CDS
<222> LOCATION: (3)..(824)

<400> SEQUENCE: 63 ca cat atc agc cac atc cac tta att ccc cac agt ctt agt ctc tta         47
   His Ile Ser His Ile His Leu Ile Pro His Ser Leu Ser Leu Leu
     1               5                  10                  15 gac acc cat ctt agt ctt aag cct ctc atg gcc acc gcg gta ttc tca        95
Asp Thr His Leu Ser Leu Lys Pro Leu Met Ala Thr Ala Val Phe Ser
                 20                  25                  30 cct tct gcc ctt cta tcc acc tcc aca tcc acc tca aca acc cct ctt       143
Pro Ser Ala Leu Leu Ser Thr Ser Thr Ser Thr Ser Thr Thr Pro Leu
             35                  40                  45 aaa gct ccc ccc ttg gcc tta acc aag acc cac gta acg atc cca tca       191
Lys Ala Pro Pro Leu Ala Leu Thr Lys Thr His Val Thr Ile Pro Ser
         50                  55                  60 tca tca aag cca ccc cta acc aat tta act acc agt tta act gct gtc       239
Ser Ser Lys Pro Pro Leu Thr Asn Leu Thr Thr Ser Leu Thr Ala Val
 65                  70                  75 gcc aca gct gct gcc ata atc ctg tcc aca acc cct cca tcg ttt gct       287
Ala Thr Ala Ala Ala Ile Ile Leu Ser Thr Thr Pro Pro Ser Phe Ala
 80                  85                  90                  95 gat gat ttg cag aca aat gca tac aac att tac tac ggc act gct gca       335
Asp Asp Leu Gln Thr Asn Ala Tyr Asn Ile Tyr Tyr Gly Thr Ala Ala
                100                 105                 110 agt gca gcc aat tat gga ggc tac ggt ggc aat tcg aac aag aaa gat       383
Ser Ala Ala Asn Tyr Gly Gly Tyr Gly Gly Asn Ser Asn Lys Lys Asp
            115                 120                 125
```

```
tca gct gag tac ata tat gac gtc cct gca ggt tgg aaa gag aga cta      431
Ser Ala Glu Tyr Ile Tyr Asp Val Pro Ala Gly Trp Lys Glu Arg Leu
        130                 135                 140 gta tca aaa gtt gag aag ggt acc aat gga aca gat agt gag ttc ttc      479
Val Ser Lys Val Glu Lys Gly Thr Asn Gly Thr Asp Ser Glu Phe Phe
145                 150                 155 aac ccc aag aag aag aca gag cga gag tac ctt acc tac ctt gct ggt      527
Asn Pro Lys Lys Lys Thr Glu Arg Glu Tyr Leu Thr Tyr Leu Ala Gly
160                 165                 170                 175 att agg caa cta ggt ccc aaa gaa gtg atc ctc aac aac tta gca ctc      575
Ile Arg Gln Leu Gly Pro Lys Glu Val Ile Leu Asn Asn Leu Ala Leu
                180                 185                 190 tca gat gtg aac ctg caa gat caa att tcc agt gca gac tct gtg aca      623
Ser Asp Val Asn Leu Gln Asp Gln Ile Ser Ser Ala Asp Ser Val Thr
            195                 200                 205 tca gaa gag agg aaa gat gac aag gga cag gtt tac tat gat tat gag      671
Ser Glu Glu Arg Lys Asp Asp Lys Gly Gln Val Tyr Tyr Asp Tyr Glu
        210                 215                 220 att gct gga gct ggt tca cac agt ttg ata tcg gta aca tgt gcc agg      719
Ile Ala Gly Ala Gly Ser His Ser Leu Ile Ser Val Thr Cys Ala Arg
225                 230                 235 aac aag cta tat gcg cat ttt gtt agc gca cca aca ccc gaa tgg aat      767
Asn Lys Leu Tyr Ala His Phe Val Ser Ala Pro Thr Pro Glu Trp Asn
240                 245                 250                 255 cgg gat caa gat atg ctg agg cac atc cac aac tca ttt aca aca gtc      815
Arg Asp Gln Asp Met Leu Arg His Ile His Asn Ser Phe Thr Thr Val
                260                 265                 270 ggg tca ttc tagaaagtgt atatgataat catttataga gatgtcagag              864
Gly Ser Phe aggcatacat ttgaatgtac ttctgatgag ctggacttct tgatctatgt aacattgtaa    924
cgaaaattct ttctgggtta tcagaaacct agtgagtgct tgaaacttgc aatgagaaac    984
tcttcaataa acaatgactt gtatcaaaaa aaaaaaaaaa aaaaa                    1029

<210> SEQ ID NO 64
<211> LENGTH: 274
<212> TYPE: PRT
<213> ORGANISM: Mesembryanthemum crystallinum

<400> SEQUENCE: 64

His Ile Ser His Ile His Leu Ile Pro His Ser Leu Ser Leu Leu Asp
  1               5                  10                  15

Thr His Leu Ser Leu Lys Pro Leu Met Ala Thr Ala Val Phe Ser Pro
                 20                  25                  30

Ser Ala Leu Leu Ser Thr Ser Thr Ser Thr Thr Pro Leu Lys
             35                  40                  45

Ala Pro Pro Leu Ala Leu Thr Lys Thr His Val Thr Ile Pro Ser Ser
         50                  55                  60

Ser Lys Pro Pro Leu Thr Asn Leu Thr Thr Ser Leu Thr Ala Val Ala
 65                  70                  75                  80

Thr Ala Ala Ala Ile Ile Leu Ser Thr Pro Pro Ser Phe Ala Asp
                 85                  90                  95

Asp Leu Gln Thr Asn Ala Tyr Asn Ile Tyr Tyr Gly Thr Ala Ala Ser
                100                 105                 110

Ala Ala Asn Tyr Gly Gly Tyr Gly Gly Asn Ser Asn Lys Lys Asp Ser
            115                 120                 125

Ala Glu Tyr Ile Tyr Asp Val Pro Ala Gly Trp Lys Glu Arg Leu Val
        130                 135                 140
```

```
Ser Lys Val Glu Lys Gly Thr Asn Gly Thr Asp Ser Glu Phe Phe Asn
145                 150                 155                 160

Pro Lys Lys Thr Glu Arg Glu Tyr Leu Thr Tyr Leu Ala Gly Ile
            165                 170                 175

Arg Gln Leu Gly Pro Lys Glu Val Ile Leu Asn Asn Leu Ala Leu Ser
                180                 185                 190

Asp Val Asn Leu Gln Asp Gln Ile Ser Ser Ala Asp Ser Val Thr Ser
                195                 200                 205

Glu Glu Arg Lys Asp Asp Lys Gly Gln Val Tyr Tyr Asp Tyr Glu Ile
            210                 215                 220

Ala Gly Ala Gly Ser His Ser Leu Ile Ser Val Thr Cys Ala Arg Asn
225                 230                 235                 240

Lys Leu Tyr Ala His Phe Val Ser Ala Pro Thr Pro Glu Trp Asn Arg
                245                 250                 255

Asp Gln Asp Met Leu Arg His Ile His Asn Ser Phe Thr Thr Val Gly
                260                 265                 270

Ser Phe

<210> SEQ ID NO 65
<211> LENGTH: 33
<212> TYPE: DNA
<213> ORGANISM: Artificial Sequence
<220> FEATURE:
<223> OTHER INFORMATION: Description of Artificial Sequence:Primer

<400> SEQUENCE: 65
gctctgagaa ccgtctagac ttagatgaag gtg                                33

<210> SEQ ID NO 66
<211> LENGTH: 30
<212> TYPE: DNA
<213> ORGANISM: Artificial Sequence
<220> FEATURE:
<223> OTHER INFORMATION: Description of Artificial Sequence:Primer

<400> SEQUENCE: 66
tctctcgttc atctcgagct attacagctc                                    30

<210> SEQ ID NO 67
<211> LENGTH: 225
<212> TYPE: DNA
<213> ORGANISM: Bruguiera sexangula

<400> SEQUENCE: 67
atgaaggtgg tcggccctgc aagatcaaag agtgctactg tacccaccca aacagtattg    60
cctttcaagt tcacaaaccc gtcgttactc actcgatcgc taagcttttc atcaaaaggt   120
tcaagctttg acagcttctc tgtacccaaa agatcttttt cttgcagaag ccaagccact   180
ccatctgatg atgcctcaag acccaccaaa gttcaagagc tgtaa                   225

<210> SEQ ID NO 68
<211> LENGTH: 74
<212> TYPE: PRT
<213> ORGANISM: Bruguiera sexangula

<400> SEQUENCE: 68

Met Lys Val Val Gly Pro Ala Arg Ser Lys Ser Ala Thr Val Pro Thr
1               5                   10                  15

Gln Thr Val Leu Pro Phe Lys Phe Thr Asn Pro Ser Leu Leu Thr Arg
```

```
                 20                  25                  30

Ser Leu Ser Phe Ser Ser Lys Gly Ser Ser Phe Asp Ser Phe Ser Val
            35                  40                  45

Pro Lys Arg Ser Phe Ser Cys Arg Ser Gln Ala Thr Pro Ser Asp Asp
        50                  55                  60

Ala Ser Arg Pro Thr Lys Val Gln Glu Leu
65                  70

<210> SEQ ID NO 69
<211> LENGTH: 74
<212> TYPE: PRT
<213> ORGANISM: C-52

<400> SEQUENCE: 69

Met Lys Val Val Gly Pro Ala Arg Ser Lys Ser Ala Thr Val Pro Thr
1               5                   10                  15

Gln Thr Val Leu Pro Phe Lys Phe Thr Asn Pro Ser Leu Leu Thr Arg
            20                  25                  30

Ser Leu Ser Phe Ser Ser Lys Gly Ser Ser Phe Asp Ser Phe Ser Val
            35                  40                  45

Pro Lys Arg Ser Phe Ser Cys Arg Ser Gln Ala Thr Pro Ser Asp Asp
        50                  55                  60

Ala Ser Arg Pro Thr Lys Val Gln Glu Leu
65                  70

<210> SEQ ID NO 70
<211> LENGTH: 225
<212> TYPE: DNA
<213> ORGANISM: Bruguiera sexangula

<400> SEQUENCE: 70
atgaaggtgg tcggccctgc aagatcaaag agtgctactg tacccaccca aacagtattg      60
cctttcaagt tcacaaaccc gtcgttactc actcgatcgc taagcttttc atcaaaaggt    120
tcaagctttg acagcttctc tgtacccaaa agatcttttt cttgcagaag ccaagccacc    180
ccatctgatg atgcctcaag acccaccaaa gttcaagagc tgtaa                    225

<210> SEQ ID NO 71
<211> LENGTH: 73
<212> TYPE: PRT
<213> ORGANISM: Bruguiera sexangula

<400> SEQUENCE: 71

Met Lys Val Val Gly Pro Ala Arg Ser Lys Ser Ala Thr Val Pro Thr
1               5                   10                  15

Gln Thr Val Leu Pro Phe Lys Phe Ala Asn Pro Ser Leu Leu Thr Arg
            20                  25                  30

Ser Leu Ser Phe Ser Ser Lys Gly Ser Ser Phe Asp Ser Phe Ser Val
            35                  40                  45

Pro Lys Arg Ser Phe Ser Cys Arg Ser Gln Ala Thr Pro Ser Asp Asp
        50                  55                  60

Ala Ser Arg Pro Thr Lys Val Gln Glu
65                  70

<210> SEQ ID NO 72
<211> LENGTH: 225
<212> TYPE: DNA
<213> ORGANISM: Bruguiera sexangula
```

-continued

```
<400> SEQUENCE: 72
atgaaggtgg tcggccctgc aagatcaaag agtgctactg tacccaccca aacagtattg      60
cctttcaagt tcgcaaaccc gtcgttactc actcgatcgc taagcttttc atcaaaaggt     120
tcaagctttg acagcttctc tgtacccaaa agatcttttt cttgcagaag ccaagccact     180
ccatctgatg atgcctcaag acccaccaaa gttcaagagc tgtaa                    225
```

ENVIRONMENTAL STRESS RESISTANCE GENE

TECHNICAL FIELD

The present invention relates to DNA encoding proteins having the activity of improving tolerance against environmental stresses such as salt stress and its screening methods, proteins having the activity of improving tolerance against environmental stresses such as salt stress, and the use of the DNA or the proteins such as transgenic plants.

BACKGROUND OF THE INVENTION

Organisms living in the nature are exposed to various environmental stresses such as salt stress, high temperature stress, low temperature stress, freezing stress, or drought stress. Specifically, salt stress is one of the main factors inhibiting the growth of many species of higher plants. Since the improvement of tolerance against salt in higher plants leads to the increase of the farm products, attempts have recently been made vigorously to improve salt tolerance of higher plants by gene introduction.

For example, H. J. Bohnert et al. show that salt tolerance of tobacco plants was improved by introducing the mannitol synthetase derived from coliforms into tobacco plants (Science 259, 22, 508–510, 1993). It has been shown that similar effects of improvement of salt tolerance in higher plants can be obtained by introducing proline synthetase (Plant Physiol. 108, 1387–1394, 1995) or glycine betaine synthetase (Plant J. 12, 133–142, 1997, Plant Mol. Biol. 38, 1011–1019, 1998). However, the recombinant plants obtained by the introduction of the genes encoding the enzymes will not acquire salt tolerance enough to cope with the level of the seawater.

In general, environmental stresses such as salt stress affect on various organic responses. In other words, in order to produce genetically modified plants capable of growing in an environment at a high level of salt concentration in a stable manner, it is necessary to use gene population encoding proteins having the activity of improving salt tolerance. Main methods used in the past to isolate gene population encoding proteins having the activity of improving environmental stress tolerance have been based on the assumption that "mechanisms resisting to stress express when stress is imposed." More specifically, it detects proteins or mRNA which is specifically expressed when some environmental stress is imposed on a plant, acquires the genes for them following methods of molecular biology, and genetically introducing them to plants weak to such stress, and examines whether the plants become to show tolerance to environmental stress. It is certain that such methods have been used to isolate the genes specifically induced by environmental stress. However, it was rare that plants with a high level of tolerance to environmental stress were made by introducing the genes to plants weak to environment stress. For example, if a gene responsible for salt tolerance expresses with or without stress in a plant growing under a stressful condition such as a high concentration of salt, it is impossible to detect stress tolerance genes in the previous methods. Genome projects have recently been carried out on plants with a high level of stress tolerance. Although their base sequences or sequences of amino acids may be revealed, the present state is that as in other genome projects, there are many proteins whose functions are not identified, and it cannot specify which proteins are responsible for tolerance to environmental stress.

On the other hand, mangroves are woody plants growing in soil containing a high concentration of salt along the coast and near the entry of rivers. Mangrove plants are thought to have acquired special mechanisms for salt tolerance in the process of evolution. Therefore, if we can isolate gene population of mangrove plants responsible for salt tolerance, it is expected that the isolates can be used to apply to improve salt tolerance of higher plants. However, there is no known example of analyzing mechanism of salt tolerance of mangrove plants at genetic level. One of the reasons is that it was quite difficult to extract mRNA of the genes directly involved in salt tolerance from such woody plants.

Recently, Mimura et al. have established cultured cell lines of *Bruguiera sexangula*, a kind of mangrove plants (J. Res. 110, 25–29, 1997). The cultured cells are different from other cultured plant cells for their quite specific properties; they can be subjected to suspension culture, and they can grow in a stable manner under the circumstance where the salt concentration is 150 mM or more (J. Plant Res. 110, 31–36, 1997). However, it has never been attempted even to detect a group of genes involved in salt tolerance of mangrove plants by constructing cDNA library of mangrove plants with the use of such cultured cells. Moreover, there are few examples of improving salt tolerance of higher plants by introducing the genes derived from other plants with salt tolerance. One representative example is to improve salt tolerance of tobacco plants by introducing inositole methyltransferase genes derived from *Masembryanthenum crystallinum*, which is a halophyte, into tobacco, and increasing the content of ononitol, a kind of compatible solute, into transformed cells (Plant Physiol. 115, 1221–1219, 1998), and another example is to slightly improve salt tolerance of rice plants by introducing the genes encoding stress inducing proteins (LEA proteins) derived from barley with a relatively high level of salt tolerance, into rice plants (Plant Physiol. 110, 249–257, 1996). As shown above, there is no established technology for isolating effectively a group of genes encoding proteins having the activity of improving tolerance to salt stress, and at the present situation, the environmental stress tolerant genes in many halophytes such as a group of mangrove plants have not been studied well enough.

Further, the functions of improving salt stress tolerance of proteins can be improved by artificially modifying genes encoding the proteins having the activity of improving salt stress tolerance, it becomes possible to produce plants with a higher level of tolerance to salt stress. There was an attempt to stabilize the expression level of choline dehydrogenase in plants by modifying some codons when expressing choline dehydrogenase derived from coliforms in a plant, which leads to stabilization of the level of glycine betaine (a kind of compatible solute, which has a function of improving salt tolerance in plants), which is a metabolite of choline dehydrogenase (Stress responses of photosynthesis organisms (ed. Satoh K., Murata N.), 115–131, Elsevier Science, Amsterdam). However, this is not the one that changes a sequence of amino acids in proteins. It has never been reported to improve the level of salt stress tolerance of higher plants by introducing proteins whose sequences of amino acids are modified (improved) and whose activity improves salt stress tolerance. Further, it is expected that there are possibilities that the genes or their modified genes involved in salt tolerance have the activity of improving tolerance not only to salt stress but also to all or some of the other kinds of environmental stresses (thermal, freezing, osmotic pressure, drought, and ultraviolet).

DISCLOSURE OF THE INVENTION

The object of the present invention is to provide efficient methods for screening genes having the effects of improving tolerance to environmental stress in various organisms, genes of proteins (proteins having the activity of improving environmental stress tolerance) having the activity of improving environmental stress tolerance obtained from the screening method, proteins having the activity of improving environmental stress tolerance, and transgenic plants or the like whose salt tolerance is improved.

To solve the problem mentioned above, the present inventors focused on mangroves, which are halophytes, obtained a portion of cultured cells of *Bruguiera sexangula*, which was established as a cultured cell lines, cultured this cell line in the presence of 100 mM of NaCl, produced cDNA library based on the mRNA extracted from the cultured cells, and attempted to detect genes involved in salt tolerance in mangroves. Normally, differential screening is widely used to screen genes involved in salt tolerance (see Publication for Japanese Laid-Open Patent Application No. 10-295380 on novel thionine genes induced by salt stress). However, the genes which this screening method isolates are the ones specifically derived under stressful conditions, and it is not always the case that the expression of the genes in other cells leads to the improvement of stress tolerance of the cells. The present inventors developed methods of using gene expression systems of coliform to detect genes involved in stress tolerance.

When screening genes involved in salt tolerance by using gene expression systems of coliform, a problem is that the defending mechanism of coliform itself strongly works against sodium chloride (NaCl). The coliforms widely used in the field of molecular biology at the presence such as DH5α, HB101, JM109 have the ability to form colonies even in the 2YT agar medium containing 100 mM or more of NaCl. When the screening is carried out with these cell lines, we would obtain not only the clones with their salt tolerance improved by the expression of candidate cDNA derived from the above-mentioned cDNA library but also the clones irrelevant to salt tolerance, since salt tolerance mechanism works strongly in the coliforms themselves, and it is extremely difficult to discern them. For these reasons, the selection of genes relevant to salt tolerance by using gene expression systems of coliform has never been carried out. The present inventors discovered the coliforms where the level of the salt tolerance mechanism becomes low in comparison with that of other coliforms, and succeeded in screening genes relevant to salt tolerance with the use of coliforms for the first time.

It was confirmed that the group of genes (cDNA), derived from halophytes such as mangroves isolated by the present inventors following the above-mentioned method, has functions of improving the salt tolerance in coliform. Since it was possible to improve the level of salt tolerance in the coliforms by expressing the plant genes in coliforms, which are different organisms, a group of such genes are considered to have functions of improving salt tolerance in a wide range of organisms from prokaryotes to eukaryotes. In fact, the present inventors have succeeded in improving the salt tolerance in yeast, plant cells (cultured tobacco cells), and plant organisms (tobacco plants) by introducing a single gene, which is isolated and named mang1 gene, from among the group of genes involved in stress tolerance. It is also confirmed that mang1 has functions of improving the levels of tolerance to environmental stresses such as thermal, osmotic pressure, freezing other than salt tolerance. Further, we found that it was possible to obtain proteins having stronger activity of improving salt tolerance by introducing random mutants into mang1 cDNA, introducing the mutant cDNA into coliforms, and carrying out the process of selecting once, or twice or more under more stringent conditions than the selecting condition before the mutation. The present invention has been accomplished based on the sequence of researches.

The present invention relates to a method for screening DNA encoding proteins having the activity of improving environmental stress tolerance wherein candidate cDNA derived from cDNA library is introduced into host cells, the obtained transformed cells are cultured under the conditions where the host cells cannot substantially grow, the clones grown after culturing are selected, and the candidate cDNA introduced from the selected clones is isolated, a method for screening DNA encoding proteins having the activity of improving environmental stress tolerance wherein candidate cDNA derived from cDNA library is introduced into host cells, the obtained transformed cells are cultured under conditions where the host cells cannot substantially grow, the clones grown after the culturing are selected, candidate cDNA is isolated from the selected clones, the isolated candidate cDNA is introduced into the isolated cDNA, the mutant cDNA is introduced into host cells, and the process of selecting is repeated one or more times under stringent conditions of selecting mutant cDNA, a method for screening according to one of the above, wherein the environmental stress is one or more of chemical substance stress, high temperature stress, low temperature stress, freezing stress, drought stress, ozone stress, ultraviolet stress, radiation stress, or osmotic pressure stress, a method for screening according to one of the above, wherein the chemical substance stress is salt stress, the a method for screening according to any one of the above, wherein the host cell is a coliform, a method for screening according to one of the above, wherein the coliform is SOLR strain, a method for screening according to any one of the above, wherein an environmental condition where host cells cannot substantially grow is 350 mM or more of salt concentration.

The present invention also relates to DNA encoding proteins having the activity of improving environmental stress tolerance wherein the DNA is obtained according to any one of the above, DNA encoding proteins having the activity of improving environmental stress tolerance according to one of the above, wherein the environmental stress is one or more of stresses selected from chemical substance stress, high temperature stress, low temperature stress, freezing stress, drought stress, ozone stress, ultraviolet stress, radiation stress, or osmotic pressure stress, DNA encoding proteins having the activity of improving the environmental stress tolerance as described above, wherein the chemical substance stress is salt stress, DNA encoding proteins having the activity of improving the environmental stress tolerance, wherein the proteins having the activity of improving the environmental stress tolerance are derived from plants, DNA encoding proteins having the activity of improving the environmental stress tolerance, wherein the plant is *Bruguiera sexangla, Avicennia marina, Sueada japonica, Salsola komarovii*, or *Mesembryanthemum crystallinum*, DNA encoding proteins according to any one of the following (a) to (c): (a) a protein comprising the sequence of amino acids shown in Seq. ID No. 2, (b) a protein comprising a sequence of amino acids having 70% or more of homology with the sequence of amino acids shown in Seq. ID No. 2, and having the activity of tolerance at least against salt stress, (c) a protein having a sequence of amino acids wherein one or more of amino acids are deleted, substituted, or added in the sequence of amino acids shown in Seq. ID No. 2, and having the activity of improving tolerance at least against salt stress, DNA comprising part or whole of the sequence of bases shown in Seq. ID No. 1, or its complementary sequence, DNA hybridized with this DNA under stringent conditions, and encoding proteins having the activity of improving tolerance at least against salt stress, DNA encoding proteins according to any one of the following (a) or (b): (a) a protein comprising the sequence of amino acids shown in Seq. ID No. 4, (b) a protein comprising a sequence of amino acids wherein one or more of amino acids are deleted, substituted, or added in the sequence of amino acids shown in Seq. ID No. 4, and having the activity of improving tolerance at least against salt stress, DNA comprising part or whole of the sequence of bases shown in Seq. ID No. 3 or its complementary sequence, DNA hybridized with this DNA under stringent conditions, and encoding proteins having the activity of improving tolerance at least against salt stress, DNA encoding proteins according to any one of the following (a) or (b): (a) a protein comprising the sequence of amino acids shown in Seq. ID No. 6, (b) a protein comprising the sequence of amino acids wherein one or more of amino acids are deleted, substituted, or added in the sequence of amino acids shown in Seq. ID No. 6, and having the activity of improving tolerance at least against salt stress, DNA comprising part or whole of the sequence of bases shown in Seq. ID No. 5 or its complementary sequence, DNA hybridized with this DNA under stringent conditions, and encoding proteins comprising the activity of improving tolerance at least against salt stress, DNA encoding proteins according to any one of the following (a) or (b): (a) a protein comprising the sequence of amino acids shown in Seq. ID No. 8, (b) a protein comprising a sequence of amino acids wherein one or more of amino acids are deleted, substituted, or added in the sequence of amino acids shown in Seq. ID No. 8, and having the activity of improving tolerance at least against salt stress, DNA comprising part or whole of the sequence of bases shown in Seq. ID No. 7 or its complementary sequence, DNA hybridized with this DNA under stringent conditions, and encoding proteins having the activity of improving tolerance at least against salt stress, DNA encoding proteins according to any one of the following (a) or (b): (a) a protein comprising a sequence of amino acids shown in Seq. ID No. 10, (b) a protein comprising a sequence of amino acids wherein one or more of amino acids are deleted, substituted, or added in the sequence of amino acids shown in Seq. ID No. 10, and having the activity of improving tolerance at least against salt stress, DNA comprising part or whole of the sequence of bases shown in Seq. ID No. 9 or its complementary sequence, DNA hybridized with this DNA under stringent conditions, and encoding proteins having the activity of improving tolerance at least against salt stress, DNA encoding proteins according to any one of the following (a) or (b): (a) a protein having the sequence of amino acids shown in Seq. ID No. 12, (b) a protein having a sequence of amino acids wherein one or more of amino acids are deleted, substituted, or added in the sequence of amino acids shown in Seq. ID No. 12, and having the activity of improving tolerance at least against salt stress, DNA comprising part or whole of the sequence of bases shown in Seq. ID No. 11 or its complementary sequence, DNA hybridized with this DNA under stringent conditions, and encoding proteins having the activity of improving tolerance at least against salt stress, DNA encoding proteins according to any one of the following (a) or (b): (a) a protein having the sequence of amino acids shown in Seq. ID No. 14, (b) a protein having a sequence of amino acids wherein one or more of amino acids are deleted, substituted, or added in the sequence of amino acids shown in Seq. ID No. 14, and having the activity of improving tolerance at least against salt stress DNA comprising part or whole of the sequence of bases shown in Seq. ID No. 13 or its complementary sequence, DNA hybridized with this DNA under stringent conditions, and encoding proteins having the activity of improving tolerance at least against salt stress, DNA encoding proteins according to any one of the following (a) or (b): (a) a protein comprising the sequence of amino acids shown in Seq. ID No. 16, (b) a protein comprising a sequence of amino acids wherein one or more of amino acids are deleted, substituted, or added in the sequence of amino acids shown in Seq. ID No. 16, and having the activity of improving tolerance at least against salt stress, DNA comprising part or whole of the sequence of bases shown in Seq. ID No. 15 or its complementary sequence, DNA hybridized with this DNA under stringent conditions, and encoding proteins having the activity of improving tolerance at least against salt stress, DNA encoding proteins according to any one of the following (a) or (b): (a) a protein comprising the sequence of amino acids shown in Seq. ID No. 18, (b) a protein comprising a sequence of amino acids wherein one or more of amino acids are deleted, substituted, or added in the sequence of amino acids shown in Seq. ID No. 18, and having the activity of improving tolerance at least against salt stress, DNA having part or whole of the sequence of bases shown in Seq. ID No. 17 or its complementary sequence, DNA hybridized with the this DNA under stringent conditions, and encoding proteins having the activity of improving tolerance at least against salt stress, DNA encoding proteins according to any one of the following (a) or (b): (a) a protein comprising the sequence of amino acids shown in Seq. ID No. 20, (b) a protein comprising a sequence of amino acids wherein one or more of amino acids are deleted, substituted, or added in the sequence of amino acids shown in Seq. ID No. 20, and having the activity of improving tolerance at least against salt stress, DNA comprising part or whole of the sequence of bases shown in Seq. ID No. 19 or its complementary sequence, DNA hybridized with this DNA under stringent conditions, and encoding proteins having the activity of improving tolerance at least against salt stress, DNA encoding proteins according to any one of the following (a) or (b): (a) a protein comprising the sequence of amino acids shown in Seq. ID No. 22, (b) a proteins comprising a sequence of amino acids wherein one or more of amino acids are deleted, substituted, or added in the sequence of amino acids shown in Seq. ID No. 22, and having the activity of improving tolerance at least against salt stress, DNA comprising part or whole of the sequence of bases shown in Seq. ID No. 21 or its complementary sequence, DNA hybridized with this DNA under stringent conditions, and encoding proteins having the activity of improving tolerance at least against salt stress, DNA encoding proteins according to any one of the following (a) or (b): (a) a protein comprising the sequence of amino acids shown in Seq. ID No. 24, (b) a protein comprising a sequence of amino acids wherein one or more of amino acids are deleted, substituted, or added in the sequence of amino acids shown in Seq. ID No. 24, and having activity of improving tolerance at least against salt stress, DNA comprising part or whole of the sequence of bases shown in Seq. ID No. 23 or its complementary sequence, DNA hybridized with this DNA under stringent conditions, and encoding proteins having the activity of improving tolerance at least against salt stress, DNA encoding proteins according to any one of the following (a) or (b): (a) a protein comprising the sequence of amino acids shown in Seq. ID No. 26, (b) a protein comprising a sequence of amino acids wherein one or more of amino acids are deleted, substituted, or added in the sequence of amino acids shown in Seq. ID No. 26, and having the activity of improving tolerance at least against salt stress, DNA comprising part or whole of the sequence of bases shown in Seq. ID No. 25 or its complementary sequence, DNA hybridized with this DNA under stringent conditions, and encoding proteins having the activity of improving tolerance at least against salt stress, DNA encoding proteins according to any one of the following (a) or (b): (a) a protein comprising the sequence of amino acids shown in Seq. ID No. 28, (b) a protein comprising a sequence of amino acids wherein one or more of amino acids are deleted, substituted, or added in the sequence of amino acids shown in Seq. ID No. 28, and having the activity of improving tolerance at least against salt stress, DNA comprising part or whole of the sequence of bases shown in Seq. ID No. 27 or its complementary sequence, DNA hybridized with this DNA under stringent conditions, and encoding proteins having the activity of improving tolerance at least against salt stress, DNA encoding proteins according to any one of the following (a) or (b): (a) a protein comprising the sequence of amino acids shown in Seq. ID No. 30, (b) a protein comprising a sequence of amino acids wherein one or more of amino acids are deleted, substituted, or added in the sequence of amino acids shown in. ID No. 30, and having the activity of improving tolerance at least against salt stress, DNA comprising part or whole of the sequence of bases shown in Seq. ID No. 29 or its complementary sequence, DNA hybridized with this DNA under stringent conditions, and encoding proteins having the activity of improving tolerance at least against salt stress, DNA encoding proteins according to any one of the following (a) or (b): (a) a protein comprising the sequence of amino acids shown in Seq. ID No. 32, (b) a protein comprising a sequence of amino acids wherein one or more of amino acids are deleted, substituted, or added in the sequence of amino acids shown in Seq. ID No. 32, and having the activity of improving tolerance at least against salt stress, DNA comprising part or whole of the sequence of bases shown in Seq. ID No. 31 or its complementary sequence, DNA hybridized with this DNA under stringent conditions, and encoding proteins having the activity of improving tolerance at least against salt stress, DNA encoding proteins according to any one of the following (a) or (b): (a) a protein comprising the sequence of amino acids shown in Seq. ID No. 34, (b) a protein comprising a sequence of amino acids wherein one or more of amino acids are deleted, substituted, or added in the sequence of amino acids shown in Seq. ID No. 34, and having the activity of improving tolerance at least against salt stress, DNA comprising part or whole of the sequence of bases shown in Seq. ID No. 33 or its complementary sequence, DNA hybridized with this DNA under stringent conditions, and encoding proteins having the activity of improving tolerance at least against salt stress, DNA encoding proteins according to any one of the following (a) or (b): (a) a protein comprising the sequence of amino acids shown in Seq. ID No. 36, 38, 40, 42, 44, 46, 48, 50, 52, 54, 56, 58, 60, 62, or 64, (b) a protein comprising a sequence of amino acids wherein one or more of amino acids are deleted, substituted, or added in the sequence of amino acids shown in Seq. ID No. 36, 38, 40, 42, 44, 46, 48, 50, 52, 54, 56, 58, 60, 62, or 64, and having the activity of improving tolerance at least against salt stress, DNA comprising part or whole of the sequence of bases shown in Seq. ID No. 35, 37, 39, 41, 43, 45, 47, 49, 51, 53, 55, 57, 59, 61, or 63, or its complementary sequence, and DNA hybridized with this DNA under stringent conditions, and encoding proteins having the activity of improving tolerance at least against salt stress.

The invention also relates to a method for improving environmental stress tolerance, wherein the DNA as described above is used, a method for improving the environmental stress tolerance, wherein the environmental stress is one or more of chemical substance stress, high temperature stress, low temperature stress, freezing stress, drought stress, ozone stress, ultraviolet stress, radiation stress, and/or osmotic pressure stress, for example, a method for improving environmental stress tolerance, wherein the chemical substance stress is salt stress.

The invention also relates to a protein comprising of the sequence of amino acids shown in Seq. ID No. 2 (70), a protein having 70% or more of homology with the sequence of amino acids shown in Seq. ID No. 2, and having the activity of improving tolerance at least against salt stress, a protein comprising a sequence of amino acids wherein one or more amino acids are deleted, substituted, or added in the sequence of amino acids shown in Seq. ID No. 2, and having the activity of improving tolerance at least against salt stress, a protein comprising the sequence of amino acids shown in Seq. ID No. 4, a protein comprising a sequence of amino acids wherein one or more amino acids are deleted, substituted, or added in the sequence of amino acids shown in Seq. ID No. 4, and having the activity of improving tolerance at least against salt stress, a protein comprising the sequence of amino acids shown in Seq. ID No. 6, a protein comprising a sequence of amino acids wherein one or more amino acids are deleted, substituted, or added in the sequence of amino acids shown in Seq. ID No. 6, and having the activity of improving tolerance at least against salt stress, a protein comprising the sequence of amino acids shown in Seq. ID No. 8, a protein comprising a sequence of amino acids wherein one or more amino acids are deleted, substituted, or added in the sequence of amino acids shown in Seq. ID No. 8, and having the activity of improving tolerance at least against salt stress, a protein comprising the sequence of amino acids shown in Seq. ID No. 10, a protein comprising a sequence of amino acids wherein one or more amino acids are deleted, substituted, or added in the sequence of amino acids shown in Seq. ID No. 10, and having the activity of improving tolerance at least against salt stress, a protein comprising the sequence of amino acids shown in Seq. ID No. 12, a protein comprising a sequence of amino acids wherein one or more amino acids are deleted, substituted, or added in the sequence of amino acids shown in Seq. ID No. 12, and having the activity of improving tolerance at least against salt stress, a protein comprising the sequence of amino acids shown in Seq. ID No. 14, a protein comprising a sequence of amino acids wherein one or more amino acids are deleted, substituted, or added in the sequence of amino acids shown in Seq. ID No. 14, and having the activity of improving tolerance at least against salt stress, a protein comprising the sequence of amino acids shown in Seq. ID No. 16, a protein comprising a sequence of amino acids wherein one or more amino acids are deleted, substituted, or added in the sequence of amino acids shown in Seq. ID No. 16, and having the activity of improving tolerance at least against salt stress, a protein comprising the sequence of amino acids shown in Seq. ID No. 18, a protein comprising a sequence of amino acids wherein one or more amino acids are deleted, substituted, or added in the sequence of amino acids shown in Seq. ID No. 18, and having the activity of improving tolerance at least against salt stress, a protein comprising the sequence of amino acids shown in Seq. ID No. 20, a protein comprising a sequence of amino acids wherein one or more amino acids are deleted, substituted, or added in the sequence of amino acids shown in Seq. ID No. 20, and having the activity of improving tolerance at least against salt stress, a protein comprising the sequence of amino acids shown in Seq. ID No. 22, a protein comprising a sequence of amino acids wherein one or more amino acids are deleted, substituted, or added in the sequence of amino acids shown in Seq. ID No. 22, and having the activity of improving tolerance at least against salt stress, a protein comprising the sequence of amino acids shown in Seq. ID No. 24, a protein comprising a sequence of amino acids wherein one or more amino acids are deleted, substituted, or added in the sequence of amino acids shown in Seq. ID No. 24, and having the activity of improving tolerance at least against salt stress, a protein comprising the sequence of amino acids shown in Seq. ID No. 26, a protein comprising a sequence of amino acids wherein one or more amino acids are deleted, substituted, or added in the sequence of amino acids shown in Seq. ID No. 26, and having the activity of improving tolerance at least against salt stress, a protein comprising the sequence of amino acids shown in Seq. ID No. 28, a protein comprising a sequence of amino acids wherein one or more amino acids are deleted, substituted, or added in the sequence of amino acids shown in Seq. ID No. 28, and having the activity of improving tolerance at least against salt stress, a protein comprising the sequence of amino acids shown in Seq. ID No. 30, a protein comprising a sequence of amino acids wherein one or more amino acids are deleted, substituted, or added in the sequence of amino acids shown in Seq. ID No. 30, and having the activity of improving tolerance at least against salt stress, a protein comprising the sequence of amino acids shown in Seq. ID No. 32, a protein comprising a sequence of amino acids wherein one or more amino acids are deleted, substituted, or added in the sequence of amino acids shown in Seq. ID No. 32, and having the activity of improving tolerance at least against salt stress, a protein comprising the sequence of amino acids shown in Seq. ID No. 34, a protein comprising a sequence of amino acids wherein one or more amino acids are deleted, substituted, or added in the sequence of amino acids shown in Seq. ID No. 34, and having the activity of improving tolerance at least against salt stress, a protein comprising the sequence of amino acids shown in Seq. ID No. 36, 38, 40, 42, 44, 46, 48, 50, 52, 54, 56, 58, 60, 62, or 64, and a protein comprising a sequence of amino acids wherein one or more amino acids are deleted, substituted, or added in the sequence of amino acids shown in Seq. ID No. 36, 38, 40, 42, 44, 46, 48, 50, 52, 54, 56, 58, 60, 62, or 64, and having the activity of improving tolerance at least against salt stress.

The present invention also relates to an antibody specifically bound to the protein for example, a monoclonal antibody.

The present invention also relates to a vector comprising the DNA encoding proteins as described herein, in particular those having the activity of improving tolerance against environmental stresses.

The present invention also relates to a transformed cell obtained by introducing the vector described above into a cell, in particular a transformed cell, wherein the host cell is a plant cell and a method for producing proteins having the activity of improving environmental stress tolerance, wherein the transformed cell is cultured, and recombinant proteins are collected from the transformed cells or the supernatant of the cultured liquid.

The present invention also relates to a transgenic plant obtained by introducing the DNA encoding proteins having the activity of improving environmental stress tolerance, and by dividing, proliferating and redifferentiating the plant cell, a transgenic plant obtained by introducing the DNA encoding proteins having the activity of improving environmental stress tolerance, and by dividing, proliferating and redifferentiating the plant cell, a transgenic plant obtained by introducing the DNA encoding proteins having the activity of improving environmental stress tolerance, and by dividing, proliferating and redifferentiating the plant cell, a transgenic plant obtained by introducing the DNA encoding proteins having the activity of improving environmental stress tolerance, and by dividing, proliferating and redifferentiating the plant cell, a transgenic plant obtained by introducing the vector described above, and by dividing, proliferating and redifferentiating the plant cell, for example a transgenic plant, wherein the environmental stress is one or more of chemical substance stress, high temperature stress, low temperature stress, frenzying stress, drought stress, ozone stress, ultraviolet stress, radiation stress, and/or osmotic pressure stress, for example a transgenic plant, wherein the chemical substance stress is salt stress, and a material for breeding derived from the transgenic plant.

BRIEF DESCRIPTION OF THE DRAWINGS

FIG. 9 shows a region considered as minimal functional region of mang1 (mang1 core), and the sequences of bases and amino acids of clones wherein mutants were introduced. The white letters in the sequences of bases and amino acids shows the mutated positions. Shown in the figure are the mangrin core (DNA) (SEQ ID NO: 67), mangrin core (protein) (SEQ ID NO: 68), C-52 (DNA) (SEQ ID NO: 69), C-52 (protein) (SEQ ID NO: 70), C-80 (DNA) (SEQ ID NO: 71), and C-80 (protein) (SEQ ID NO: 72).

FIG. 10 shows the regions considered as minimal functional region of mang1, and the result of the growth of the clones, the regions of which are introduced with mutation, on the agar mediums containing 85 mM, 350 mM, and 500 mM of NaCl. As a control, SOLR introduced with a vector (pBluescript) was used alone.

BEST MODE TO CARRY OUT THE INVENTION

Figure 1:
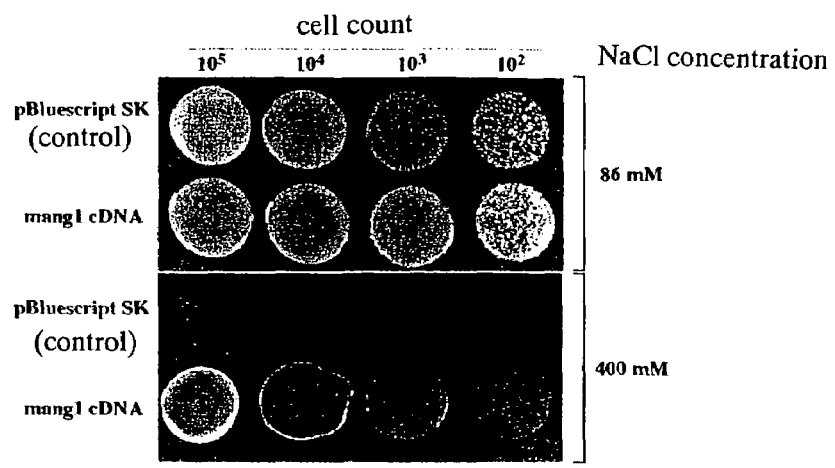
FIG. 1 shows the result of detecting salt tolerance of coliforms (SOLR) wherein mang1 is introduced. Colony forming was used as an index for detection. As a control, a vector (pBluescript SK) was used alone. Measurement was carried out with two levels of salt (NaCl) concentration.

Any method for screening DNA encoding proteins having activity of improving environmental stress tolerance in the present invention can be employed as long as it introduces candidate cDNA derived from cDNA library into host cells, cultures obtained transformed cells under the conditions where host cells are substantially unable to grow, selects clones growing after cultivation, and isolates candidate cDNA introduced from the selected clones. This screening method can be used to improve functions of proteins having activity of improving environmental stress tolerance obtained by this method. In other words, a method for screening DNA encoding proteins having activity of improving other types of environmental stress tolerance in the present invention can be exemplified by a screening method wherein candidate cDNA derived from cDNA library was introduced into host cells, the obtained transformed cells are cultured under the environment where host cells cannot substantially grow, the matured clones were selected after the cultivation, the selected clones candidate cDNA was isolated from the selected clones wherein the cDNA was introduced, random mutants were introduced into isolated candidate cDNA, the mutant cDNA was introduced into host cells, and the process of selection under more stringent conditions than the condition for selecting cDNA before mutation was repeated once or more.

As a method for introducing random mutants into optionally selected gene fragments in a method of improving function of proteins having activity of improving environmental stress tolerance by repeating the process of selection under more stringent conditions than the ones where the genes are screened from the products wherein random mutants are introduced into gene fragments obtained as a result of the first screening, PCR is a method generally used, and the method to lower the fidelity by adding manganese to PCR reactive solution (A Journal of Methods in Cell and Molecular Biology 1, 11–15, 1989, Yeast 8, 79–82, 1992) is the easiest one. DNA shuffling (Proc Natl Acad Sci USA 91, 10747–10751, 1994) can also be used as another method for random mutation.

Environmental stress mentioned above can be any kind of stress based on environmental factors, including chemical substance stress, high-temperature stress, low-temperature stress, freezing stress, drought stress, ozone stress, ultraviolet stress, radiation stress, osmotic pressure stress, and such environmental stresses can be based on either one single factor or a plurality of stresses. Further, a chemical substance stress can be any stress caused by chemical substance, and is exemplified by salt stress or toxic substance stress.

There are no restrictions on the derivations of the cDNA such as plants, animals, microorganisms, and others as long as it includes cDNA of the gene involved in environmental stress, as the above mentioned cDNA library. For example, when screening DNA encoding proteins having activity of improving salt stress tolerance, cDNA library prepared from organic species such as halophilous plants, including mangroves (*Sonneatia, Bruguiera, Kandelia, Rhizophora, Lumnitzera, Salsola komarovii, Nypa*), *Mesembryanthemum, Sueada japonica, Aster tripolium, Salicornia, Suaeda*, and *Atriplex subcordata* Kitag can be used. A method of preparing cDNA library can be any one well known to a person having ordinary skill in the art. For example, as disclosed in the examples, extraction of total mRNA from cells can be prepared following the method in Ostrem et al. (Plant Physiol. 84, 1270–1275, 1987), and poly(A) +RNA can be purified from mRNA prepared with Oligotex-dT30<super> (Daiichi Kagakusha). The cDNA library can be constructed by using ZAP-cDNA/Gigapack Cloning Kit (Stratagen) based on the purified poly(A) +RNA.

Although a host cell wherein candidate cDNA was introduced as a target of screening derived from the cDNA library, can be a cell in microorganism such as bacteria or yeast, or a cell in animals or plants, it is preferable to use animal cells whose knowledge on the host-vector system has been established, such as coliforms *bacillus, Bacillus subtilis, Saccharomyces cerevisiae*, BHK cells and the like. Among them, it is desirable to use coliforms *bacillus* because knowledge about it is abundant, it grows fast, and it is easy to handle. As a host cell, it is preferred to use a cell which cannot substantially grow under the condition where a transformed cell wherein candidate cDNA derived from cDNA library can grow, such as a salt sensitive cell or a thermal salt sensitive cell. Such cells can be prepared by screening or mutating wild type strains.

Next, transformation of cells can be performed by introducing candidate cDNA derived from cDNA library into the host cell, and such a method of introduction can be any well-known method of gene introduction such as transformation method or electroporation. The transformed cells wherein candidate cDNA is introduced are cultured under environment where the host cells cannot substantially grow, including under the condition of high concentration of salt, the condition of high temperature, the condition of drought. The matured clones can be selected by well known methods after cultivation, and candidate cDNA introduced from the selected clones can be isolated by the method.

The screening method in the present invention will be described in more details with examples where the environmental stress is salt stress and the host cell is coliform. As a coliform used as a host cell, it is preferable to use a coliform whose function of salt tolerance is degraded, and more preferably a coliform with a minimal concentration of salt inhibiting their growth. For example, it is preferred to use coliforms whose ability of forming a colony in a culture medium containing more than 750 mM of NaCl, preferably more than 500 mM of NaCl, and most desirably more than 350 mM of NaCl, in view of improving the efficiency of screening genes relevant to salt tolerance. A coliform sensitive to NaCl can be exemplified by SOLR strain (commercialized by TOYOBO, Stratagene, Riken gene bank, and others), a kind of coliform which the present inventors found, that it cannot grow on the agar medium containing a low level of salt (more than 350 mM of NaCl). When using this SOLR strain, the SOLR strain contained in said ZAP-cDNA/Gigapack Cloning Kit (Stratagene) and in vivo excision system by ExAssist helper phage can be used for the introduction of candidate cDNA. All of these operations can easily be performed following the user's manual for the kit.

The SOLR strain obtained in this ways wherein the candidate cDNA is introduced is cultured in a medium containing about 400 mM of NaCl and the matured cells are selected to select clones transformed by the DNA encoding proteins having salt tolerance. For example, such selection of clones may be carried out by culturing on agar medium for 8 to 20 hours at 37° C. and select colonies formed on the agar. For example, as a method for isolating cDNA from the selected clones, a method disclosed in a reference (Current Protocols in Molecular Biology (Greene Publishing Associates and Wiley-Interscience, 1987) can be performed by extracting plasmid DNA.

The screening to obtain the targeted transformed coliforms can be carried out repeatedly for several times. For example, the coliforms wherein cDNA library was introduced are cultured in a medium containing the minimal concentration of salt inhibiting their growth, and select the clones which can grow under this condition (first screening). Next, the cDNA are isolated from the selected clones, and are reintroduced into coliforms. The coliforms are cultured in a medium containing a higher concentration of salt than the minimal concentration of salt inhibiting their growth, and the clones which can grow under this condition are selected (second screening). By repeating such process of screening, the efficiency of isolating the genes relevant to salt tolerance can be improved. Further, as mentioned above, the second screening can be carried out by using mutant cDNA wherein random mutants are introduced into isolated cDNA.

There are no particular restrictions on the DNA encoding proteins having activities of improving the environmental stress tolerance in the present invention as long as the DNA can be obtained by the method for screening, and it can be exemplified by the DNA encoding proteins having activities of improving tolerance against one or more of chemical stress such as salt stress, thermal stress, drought stress, ozone stress, ultraviolet stress, radiation stress, osmotic pressure stress. Specifically, DNA encoding proteins having activities of improving salt stress tolerance can be exemplified as DNA derived from plants, preferably DNA derived from halophytes such as *Brugfuiera sexangula*. An example of mangrove derived DNA encoding proteins having activities of improving salt stress tolerance can be exemplified as DNA having a sequence of bases shown in Seq. ID No. 1, 3, 5, 7, 9, 11, or 13 in the list of sequences. An example of *Mesembryanthemum crystallinum* derived DNA encoding proteins having activity of improving salt stress tolerance can be exemplified as DNA having a sequence of bases shown in Seq. ID No. 15, 17, 19, 35, 63 in the list of sequences. An example of *Sueada japonica* derived DNA encoding proteins having activity of improving salt stress tolerance can be exemplified as DNA having a sequence of bases shown in Seq. ID No. 21, 37, 39, 51, 53, 57 in the list of sequences. An example of *Salsola komarovii* derived DNA encoding proteins having activity of improving salt stress tolerance can be exemplified as DNA having a sequence of bases shown in Seq. ID No. 23, 25, 41, 47, 49, 59, 61 in the list of sequences. An example of *Avicennia marina* (a kind of mangrove) derived DNA encoding proteins having activities of improving salt stress tolerance can be exemplified as DNA having a sequence of bases shown in Seq. ID No. 27, 29, 31, 33, 43, 43, 55 in the list of sequences. DNA in the present invention can be exemplified as DNA having part or whole of a sequence of bases shown in the Seq. ID No. in the list of sequences or their complementary sequences, DNA which can hybridize with the DNA under stringent conditions and encodes proteins having activities of improving tolerance at least against salt stress, DNA which encodes proteins having a sequence of amino acids shown in Seq. ID No. 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, or 64 in the list of sequence, DNA which comprises a sequence of amino acids having 70% or more of homology with the sequence of amino acids shown in Seq. ID No. 2 in the list of sequence and encodes proteins having activity of improving tolerance at least against salt stress, or DNA which comprises a sequence of amino acids wherein one or more of the amino acids are deleted, substituted, or added in the sequence of amino acids shown in Seq. ID No. 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, or 64 in the list of sequence, and encodes proteins having activities of improving tolerance at least against salt stress. It has not been reported that tolerance to salt or the like is improved by introducing the DNA into various organisms, and it is found by the present inventors for the first time.

Proteins in the present invention can be exemplified as proteins having a sequence of amino acids shown in Seq. ID No. 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, or, 64 in the list of sequence, proteins which have a sequence of amino acids having 70% or more of homology with the sequence of amino acids shown in Seq. ID No. 2 in the list of sequence and have activity of improving tolerance at least against salt stress, or proteins which have a sequence of amino acids wherein one or more of amino acids are deleted, substituted, or added in the sequence of amino acids shown in Seq. ID No. 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, or 64 in the list of sequence and have activity of improving tolerance at least against salt stress.

The sequences of amino acids shown in 8, 14, 36, 38, 40, 42, 44, 46, 48, 50, 52, 54, 56, 58, 60, 62, or 64 in the Seq. ID No. are thought not to be the ones encoding the full length of proteins. However, since there is activity of improving salt stress tolerance in itself, they are considered to be a functional region in each of the proteins of full length. As mentioned above, the present invention involves the full length of proteins involving these functional regions and DNA encoding the full length of proteins. As an example of methods for isolating the full cDNA based on partial length of cDNA, it is appropriate to use the kits such as Marathon cDNA Amplification Kit (Clontech), 3'-Full RACE Core Set (TAKARA), 5'-Full RACE Core Set (TAKARA) and follow their user's manuals.

As shown above, the present invention involves DNA encoding proteins functionally equivalent to the proteins having a sequence of amino acids shown in Seq. ID No. 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, or 64. It is well known that although a few amino acids are substituted, deleted, or added, proteins having biogenic activity can maintain the biogenic activity. Various methods for mutating amino acids in proteins are well known, and some kits are already commercialized as well. For example, it is easy to mutate amino acids in proteins by synthesizing primers wherein mutants are introduced and with the use of QuikChange Site-Directed Mutagenesis Kit (Stratagene).

Proteins having amino acids wherein one or more of amino acids are substituted, deleted, added and/or inserted in the list of a sequence of amino acids shown in Seq. ID No. 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, or 64 are all involved in the scope of the present invention as long as they have activity of improving environmental stress tolerance at least against salt stress tolerance in various organic cells (for example, plant cells, coliforms, yeast). DNA encoding proteins functionally equivalent to proteins having amino acids shown in Seq. ID No. 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, or 64 can be prepared by hybridization technology or molecular amplification technology (Molecular Cloning, a Laboratory Manual, Second Edition, Cold Spring Harbor Laboratory Press, 1989). For example, it is possible to obtain DNA or the like encoding proteins having activity of improving environmental stress tolerance including at least salt stress tolerance as an object by the hybridization of cDNA library derived from various organisms under stringent conditions where the probes are part or whole of a sequence of bases shown in Seq. ID No. 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, or 63 encoding a sequence of amino acids shown in Seq. ID No. 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, or 64 and the isolation of DNA which hybridizes with the probes.

As a condition for the hybridization to obtain the DNA, hybridization can be carried out at 42° C. and treatment of washing at 42° C. with the use of washing buffer containing 1×SSC and 0.1% of SDS. More preferably, it can be hybridized at 65° C. and treatment of washing at 65° C. with the use of washing buffer containing 0.1×SSC and 0.1% of SDS. As for factors effecting the stringency of hybridization, there are various other factors other than the thermal ones mentioned above, and a person having ordinary skill in the art is capable of carrying out the same level of stringency as illustrated in the stringency of hybridization by combining various factors in an appropriate way.

It is possible to obtain the DNA or the like encoding proteins having activity of improving environmental stress tolerance including tolerance at least against salt tolerance by polymerase chain reaction of various organism-derived DNA (or RNA) as templates by using oligonucleotides prepared based on a sequence of bases shown in Seq. ID No. 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, or 63 as primers. The present invention involves DNA which can be isolated by using hybridization technology or gene amplification technology, as long as they have activities of improving environmental stress tolerance including at least salt stress tolerance in various organic cells (such as plant cells, coliforms, or yeast).

It is thought that proteins functionally equivalent to proteins having a sequence of amino acids shown in Seq. ID No. 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, or 64 have high homology with the sequence of amino acids shown in the sequence numbers. The high level of homology stands for 70% or more, preferably 80% or more, or more preferable 90% or more (for example, 95% or more) of homology in sequences. The present invention involves DNA whose sequence of amino acids has a high level of homology with the sequence of amino acids shown in the above sequence numbers, and which encodes proteins having activity of improving tolerance at least to salt stress in various organic cells (such as plant cells, coliforms, or yeast). For example, the sequence of amino acids in Seq. ID No. 2 have activity of improving salt stress tolerance in the region comprising amino acids from 1 to 86, and therefore all of the gene DNA encoding a sequence of amino acids comprising this region, for example, are all included in the scope of the present invention. The homology in sequences can be determined, for example, by using the multi-alignment function of GENETYX-MAC (Software Development Corporation), a genetic information processing software.

There are no particular restrictions on a method for improving environmental stress tolerance in the present invention, as long as it uses DNA encoding proteins having activity of improving tolerance against one or more environmental stresses selected from chemical substance stress such as salt stress, high temperature stress, low temperature stress, freezing stress, drought stress, ozone stress, ultraviolet stress, radiation stress, osmotic pressure stress. By the method for improving environmental stress tolerance, environmental stress tolerance can be improved in tissues, organs, and cells of plants and animals, and microorganisms such as bacteria, yeast, and fungi.

As an antibody specifically binding to proteins having activity of improving tolerance against one or more environmental stresses such as chemical substance stress such as salt stress, thermal stress, drought stress, ozone stress, ultraviolet stress, radiation stress, osmotic pressure stress, any antibody can be used as long as the antibody can specifically bind to proteins in the present invention. Such antibodies can be exemplified as immune specific antibodies such as monoclonal antibiotics, polyclonal antibiotics, chimera antibiotics, single chain antibody, or human cell line antibody or the like. As for the antibodies used for preparation, these antibodies can be produced by using the following proteins having a sequence of amino acids shown in Seq. ID No. 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, or 64, proteins having a sequence of 70% or more of homology with a sequence of amino acids shown in Seq. ID No. 2 and having activity of improving tolerance at least against salt stress, and proteins having a sequence of amino acids wherein one or more the amino acids are deleted, substituted, or added in a sequence of amino acids shown in Seq. ID No. 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62 or 64 and having activities of tolerance at least against salt stress. Such antibodies are useful in elucidating the molecular structure of proteins having activity of improving environmental stress tolerance and others.

Following the conventional protocols, antibodies for proteins having activity of improving the environmental stress tolerance are produced by administering proteins having activity of improving the environmental stress tolerance in animals (preferably, except for human), or fragments, their analogues or cells involving epitope. As a technology for preparing monoclonal antibodies, any technology can be used such as hybridoma technology (Nature 256, 495–497, 1975), trioma technology, human B cell hybridoma technology (Immunology Today 4, 72, 1983) or EBV-hybridoma technology (MONOCLONAL ANTIBODIES AND CANCER THERAPY, 77–96, Alan R. Liss. Inc., 1985), which produce antibodies from the culture of successive cell strains.

The method for preparing single chain antibodies (U.S. Pat. No. 4,946,778) can apply to produce single chain antibodies for proteins having activity of improving the environmental stress tolerance in the present invention. Further, transgenic plants or transgenic animals and the like can be used to express human cell line antibodies, clones expressing proteins having activity of improving the environmental stress tolerance by using the antibodies can be isolated or identified, or the polypeptides can be purified by using affinity chromatography.

There are no special restrictions on vectors used in the present invention, as long as the vectors comprising DNA encoding proteins having activity of improving tolerance against the environmental stresses such as chemical substance stress such as salt stress, thermal stress, low temperature stress, freezing stress, drought stress, ozone stress, ultraviolet stress, radiation stress, and osmotic pressure stress. There are also no restrictions on transformed cells used in the present invention, as long as the transformed cells are obtained by introducing the vectors into host cells such as plant cells or the like. As a method for producing proteins having activity of improving environmental stress tolerance in the present invention, it can be any method as long as the transformed cells are cultured, and recombinant proteins are collected from the transformed cells or the supernatant of the cultured liquid. Further, any transgenic plant can be used in the present invention as long as it introduces DNA encoding proteins having activity of improving the environmental stress tolerance or the vectors into plant cells, and are obtained by division, proliferation, and redifferentiation of the plant cells. The following explains vectors, transformed cells, methods for producing proteins having activity of improving environmental stress tolerance, and transgenic plant in the present invention.

As mentioned above, DNA in the present invention can be used in preparing recombinant proteins. To prepare recombinant proteins, the DNA in the present invention are inserted into appropriate expression vectors, the vectors are introduced into appropriate host cells, the DNA are expressed, and then the expressed proteins are collected from the transformed cells or the supernate of the cultured liquid. The host-vector system used in expressing recombinant proteins can be exemplified as IMPACT-CN System (host cell: *E. coli* strain ER2566, vector:pTYB1, pYB2, pYB11, pYB12 (BioLabs), or pET Expression System (host cell: Epicurian Coli BL 21, vector: pET3 series (Novagen)). As for a method for introducing vectors into host cells, well known methods can be used such as electroporation method or heat shock method (IDENSHI LIBRARY NO SAKUSEIHOO (Methods of producing gene library), Yoodo-sha, 1994, SHOKUBUTU SAIBOO KOOGAKU NYUMON (Introduction to plant cell engineering), Japan Scientific Societies Press, 1998). The culture for expressing recombinant proteins can be carried out by conventional methods and under conventional conditions. Expressed proteins can be purified by Chitin Beads (BioLabs) when IMPACT-CN System is used, and His Bind Resin (Novagen) when pET Expression System is used.

DNA in the present invention can be used to produce transgenic organisms whose tolerance at least against salt stress is improved. There are no restrictions on the species of organisms in producing transgenic organisms by using DNA in the present invention. However, in the case where the genes used are derived from mangrove, it is preferable to use higher plants. In producing such transgenic plants, it is more advantageous to insert DNA into vectors to express them in plant cells, to introduce them into plant cells, and to recover the transformation plant cells in order to obtain transgenic plants.

As vectors used in producing transgenic plants, it is preferable to use pBI101 commercialized by Toyobo, or pIG121Hm (Plant J. 6, 271–282, 1994). Although there are no special restrictions on the species of plant cells wherein vectors are introduced, they are considered to be rice plant, wheat, corn, soy, tobacco, carrot. Morphology of plant cells can be protoplast, callus, part of plant organism (leafdisk, hypocotyl) and the like. As a method for introducing vectors into host plant cells, the *Agrobacterium* method is most preferable, and polyethylene glycole method, electroporation method, particle gun method, and others can also be used (MODEL SHOKUBUTU NO JIKKEN PROTOCOL (Experimental Protocols for plant models), Shujin-sha, 1996).

The ways how plant cells wherein vectors are introduced vary depending on the species of plants. The following processes are carried out when rice plant is taken as an example. The callus is derived from matured seeds, and the obtained callus is infected with *Agrobacterium* wherein cDNA are introduced. After the period of co-culturing, they are transferred to selective medium to culture. About three weeks later, callus is transferred to redifferentiation medium, and is cultured until redifferntiation. Transformants are recovered by transferring them to pots after 4 or 5 days of acclimatation. (MODEL SHOKUBUTU NO JIKKEN PROTOCOL (Experimental Protocols for plant models), Shujin-sha, 1996). As methods for recovering carrot, tobacco, and others, the methods proposed by Dr. Kato and Dr. Shono are appropriate for each (SHOKUBUTU SOSHIKI BAIYOO NO GIJUTU (Technologies for culturing plant tissues), Asakura-shoten, 1983).

Breeding materials derived from transgenic plants in the present invention can be any one as long as they are derived from the transgenic plants, and more specifically seeds, tuberous roots, ears, mericlone, and the like can be used as materials for culturing and proliferating, depending on the species of plants. Further, it is possible to produce massively transgenic plants in the present invention based on the breeding materials.

In the following, the present invention will be explained with concrete examples. However, it will not be restricted in any way by the concrete examples.

EXAMPLE 1

Preparation of cDNA Library of Mangrove and Other Halophytes Plants

Suspension culture cell lines of *Bruguiera sexangula* established by Miura was used as mangrove suspension culture cells (J. Plant Res. 110, 25–29, 1997). The cells are cultured in AA medium containing 100 mM of NaCl, separated 120 ml for each flask of 500 ml, and performed shaken culture (70 rpm) in a dark room at 26° C. Following the procedure shown below, the cDNA library of mangrove was carried out by using suspension culture cells. First, following the method by Ostrem et al. (Plant Physiol. 84, 1270–1275, 1987), total RNA were extracted, and then poly(A)+RNA was purified by using Oligotex-dT30<super> (Daiichi Kagaku sha). The purified poly(A)+RNA was used to synthesize cDNA, and cDNA library was constructed by introducing the lambda phage vector λ ZapII (Stratagene). Methods for constructing cDNA library by introducing λ ZapII are well known, and the actual procedure was followed by the manufacturer's manual by Stratagene. As a result, a mangrove cDNA library containing independent clones of $10^6$ was successfully constructed. In order to construct cDNA libraries of other halophytes plants such as *Avicennia marina* (a kind of mangrove), *Sueada japonica*, *Salsola komarovii*, *Mesembryanthemum crystallinum*, leaves of each plant organism are used. The same method was used to construct cDNA library as in the case of mangroves. The obtained cDNA library contained $10^5$ to $10^6$ of independent clones for each.

EXAMPLE 2

Determination of the Conditions of Screening cDNA Relevant to Salt Tolerance

The present inventors used the gene expression system of coliforms as a method for screening cDNA relevant to salt tolerance from cDNA library, of mangrove or other halophytes. In other words, the present inventors developed a novel method for acquiring cDNA relevant to salt tolerance by introducing cDNA of mangrove or other halophytes into coliforms and selecting transformed coliforms with their salt tolerance improved. 2YT agar medium containing appropriate concentration of NaCl were used to select transformed coliforms with their salt tolerance improved. Before starting the screening, the present inventors determined the minimal concentration of NaCl inhibiting growth of various coliforms (DH5α, JM109, HB101, SOLR) in order to select the host coliforms appropriate for the screening. Such coliforms are well-known strains, and they are commercialized by TOYOBO and Stratagene, and others. Although the growth of DH5α, JM109, and HB101 is remarkably inhibited on the 2YT agar medium containing 1200 mM of NaCl; they are able to form colonies. Their growth is completely restricted under 1500 mM of NaCl. On the contrary, the growth of SOLR was remarkably inhibited in NaCl of less than 300 mM, and completely inhibited under 400 mM of NaCl. These facts show that SOLR is a strain with high sensitivity to salt, and differs from other coliforms in that it does not have a strong mechanism against salt. The fact that salt tolerant mechanisms of the coliforms themselves do not work is very effective in performing the screening. Therefore, the screening of cDNA relevant to salt tolerance from cDNA library was carried out in the following procedure by using SOLR as host coliforms and by fixing the concentration of NaCl at selection agar medium as 400 mM.

EXAMPLE 3 cDNA Screening Relevant to Salt Tolerance From cDNA Library of Mangrove and Other Halophytes cDNA library of mangrove and other halophytes was introduced into SOLR by inserting pBluescript SK carrying the library with in vivo excision system (Stratagene). The introduction of genes was performed by manufacturer's manual for ZAP-cDNA/Gigapack Cloning Kit (Stratagene). In order to select SOLR introduced with cDNA relevant to salt tolerance from SOLR introduced with cDNA of mangrove and other halophytes, two steps of screening were performed. In the first screening, SOLR introduced with cDNA of mangrove and other halophytes was planted on 2YT agar medium containing 400 mM of NaCl, 50 µg/ml of kanamycin, 50 µg/ml of ampicilline, and 0.05 mM of IPTG, and cultured at 37° C. for 20 hours. All colonies obtained under the conditions are inoculated on said agar medium again, and their growth was observed. As a result of this process, 168 clones with salt tolerance improved were obtained on *Bruguiera*. Almost the same number of clones with their salt tolerance improved were obtained successfully in the transformed coliforms wherein cDNA library of halophytes was introduced. Since there are possibilities of improving salt tolerance of clones derived from host coliforms for some reasons, second screening was performed in the following way.

Plasmids were extracted from each clone obtained by the first screening, and were all reintroduced into SOLRs. Transformants obtained were cultured until log phase on the 2YT liquid medium containing 50 µg/ml of kanamycin, 50 µg/ml of ampicillin, 0.05 mMof IPTG, diluted series were produced on 2YT liquid medium, and were spotted 25 µl for each on the agar selection medium. After the liquid was blow-dried, they were cultured at 37° C. overnight. The result confirmed that 30 clones improved salt tolerance in *Bruguiera* cDNA library. As a representative, FIG. 1 shows the result of spot experiment of coliforms wherein cDNA shown in Seq. ID No. 1 is introduced. Next, the sequence of bases of cDNA wherein 30 clones were introduced was determined following manufacturer's manual, by using Thermo Sequenase Cycle Sequencing Kit (Amersham) and DNA Sequencer LIC-4000L (LI-COR). The result is that *Bruguiera* cDNA obtained from 30 clones were classified into 7 classes. More specifically, 23 pieces of cDNA shown in Seq. ID No. 1, one piece of cDNA shown in Seq. ID No. 3, 2 pieces of cDNA shown in Seq. ID No. 5, 2 pieces of cDNA shown in Seq. ID No. 7, one piece of cDNA shown in Seq. ID No. 9, one piece of cDNA shown in Seq. ID No. 11, and one piece of cDNA shown in Seq. ID No. 13 were obtained.

In similar manners, cDNA shown in Seq. ID No. in 15, 17, 19, 35, 63 are obtained from *Mesembryanthemum crystallinum*, cDNA shown in Seq. ID No.s in 21, 37, 39, 51, 53, 57 are obtained from *Suaeda japonic*, cDNA shown in Seq. ID No.s as 23, 25, 41, 47, 49, 59, 61 are obtained from *Salsola komarovil*, and cDNA shown in Seq. ID No.s 27, 29, 31, 33, 43, 45, 55 are obtained from *Avicennia marina*.

Figure 2:
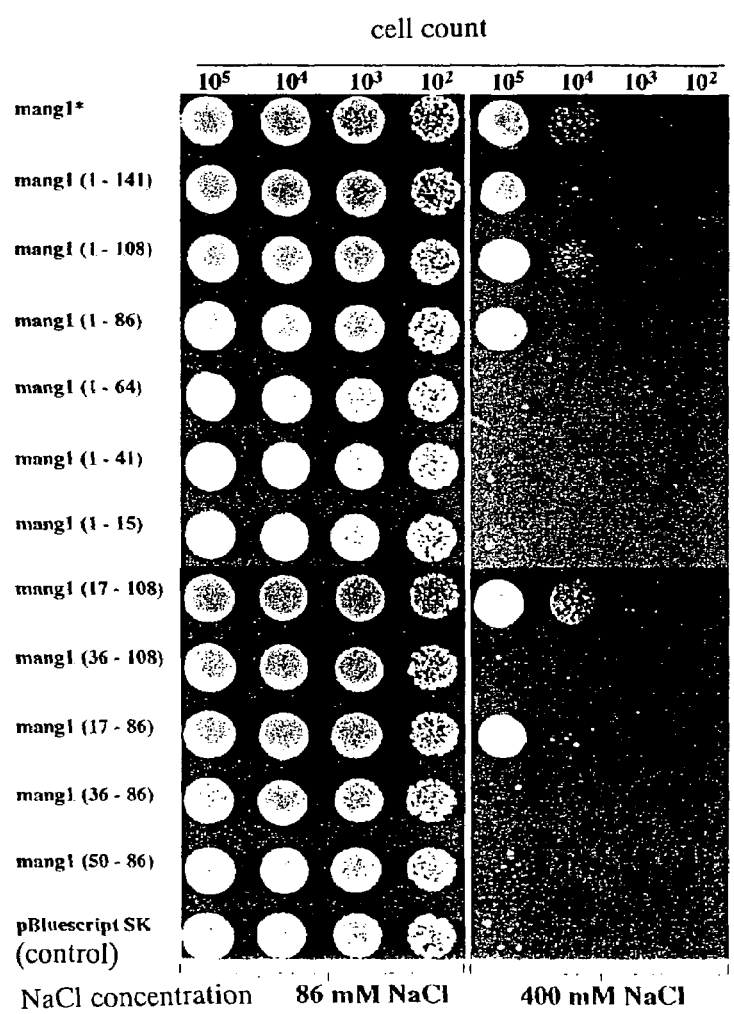
FIG. 2 shows the result of detecting salt tolerance of the coliforms wherein various parts of a sequence of mang1 were introduced. Colony forming was used as an index for detection. As a control, a vector (pBluescript SK) was used alone. Measurement was carried out with two levels of salt (NaCl) concentration. The numbers in the parentheses indicate the numbers of amino acids, and "*" indicates cDNA of mang1 containing coding and non-coding regions.

The BLAST Homology Search program was used to search homology of the sequences of amino acids encoding these pieces of DNA. The result is that there are no proteins registered which have homology with the sequence of amino acids shown in Seq. ID No. 2 in the databases such as Swiss protein, PIR, and revealing that the proteins are novel. Therefore, the present inventors named the novel protein encoding the cDNA (total number of amino acids: 141) as mangrin, and the genes as mang1. Next, functional regions of mangrin were determined. As the result of the spot experiment that the subclones were produced by introducing terminal codons into the amino acids of No. 16, 42, 65, 87, 109, 142, and subclones were produced by introducing methionine (and terminal codons were introduced immediately before this) into the amino acids of No. 16, 35, 49, and these obtained subclones were introduced into SOLRs. The result of the spot experiments of SOLRs shows that the region responsible for salt tolerance is a sequence of amino acids 17 to 86 (FIG. 2).

The sequence of amino acids shown in Seq. ID No. 4 has about 90% of homology with t-complex polypeptide 1 (pir JN0448) from *Arabidopsis thaliana*. The sequence of amino acids shown in Seq. ID No. 6 has about 80% of homology with Metallothionein-like protein TYPE 2 (EMBL L02306)

from *Ricinus communis*. The sequence of amino acids shown in Seq. ID No. 8 has about 63% of homology with RubB-like DNA helicase (AB024301) from *Homo sapiens*. The sequence of amino acids shown in Seq. ID No. 10 has about 45% of homology with Ribosomal protein S29 (pir S30298) from *Rattus norvegicus*. The sequence of amino acids shown in Seq. ID No. 12 has about 90% of homology with Elongation factor eEF-1 alpha chain (pir S66339) from *Zea mays*. The sequence of amino acids shown in Seq. ID No. 14 has about 70% of homology with cdc21 (pir S26640) from *Schizosaccharomyces pombe*. Th cDNA shown in Seq. ID No.s 1, 3, 5, 7, 9, 11, or 13 encoding proteins shown in Seq. ID No.s 2, 4, 6, 8, 10, 12, or 14 respectively are considered to have functions of improving salt tolerance in a wide-range group of organisms from procarytes such as coliforms to higher animals because they actually have functions of improving salt tolerance of coliforms.

Likewise, the sequence of amino acids derived from *Mesembryanthemum crystallinum* shown in Seq. ID No. 16 has 68% of homology with F13O1.15 gene product (gpAC006193_15) from *Arabidopsis thaliana*. The sequence of amino acids derived from *Mesembryanthemum crystallinum* shown in Seq. ID No. 18 has 78% homology with H+-transporting ATPase (EC 3.6.1.35) 14K chain (pir T01087) from *Arabidopsis thaliana*. The sequence of amino acids derived from *Mesembryanthemum crystallinum* shown in Seq. ID No. 20 has 91% of homology with 40S RIBOSOMAL PROTEIN S20 (pir T12992) from *Arabidopsis thaliana*. The sequence of amino acids derived from *Suaeda japonica* shown in Seq. ID No. 22 has 63% of homology with ozone-inducible protein (prf 2316438B) from *Atriplex canescens*. The sequence of amino acids derived from *Salsola komarovil* shown in Seq. ID No. 24 has 58% of homology with GIBBERELLIN-REGULATED PROTEIN 1 PRECURSOR (sp GAS1_ARATH) from *Arabidopsis thaliana*. The sequence of amino acids derived from *Salsola komarovii* shown in Seq. ID No. 26 has 99% of homology with ADP-ribosylation factor (gp AF 022389_1) of *Vigna unguiculata*. The sequence of amino acids derived from *Avicennia marina* shown in Seq. ID No. 28 has 56% of homology with tuberization-induced protein (prf 2310431A) of *Solanum demissum*. The sequence of amino acids derived from *Avicennia marina* shown in Seq. ID No. 30 has 69% of homology with Enod93 protein (gp MSA248334_1) of *Medicago sative*. The sequence of amino acids derived from *Avicennia marina* shown in Seq. ID No. 32 has 69% of homology with 40S RIBOSOMAL PROTEIN S21 (pir S38357) of *Oryza sative*. The sequence of amino acids derived from *Avicennia marina* shown in Seq. ID No. 34 has 79% of homology with protein phosphatase 2C homolog (AF097667) of *Mesembryanthemum crystallinum*. It also has 79% of homology with protein phosphotase 2C homolog (AF097667) of *Mesembryanthemum crystallinum*. Further, the sequence of amino acids derived from *Mesembryanthemum crystallinum* shown in Seq. ID No. 36 has 58% of homology with pRIB5 protein (gp RN17578_1) of *Ribes nigrum*. The sequence of amino acids derived from *Sueada japonica* shown in Seq. ID No. 38 has 84% of homology with tonoplast intrinsic protein (pir T12439) of *Mesembryanthemum crystallinum*. The sequence of amino acids derived from *Sueada japonica* shown in Seq. ID No. 40 has 86% of homology with phosphoethanolamine N-methyltransferase (gp AF237633_1) of *Spinacia oleracea*. The sequence of amino acids derived from *Salsola komarvii* shown in Seq. ID No. 42 has 83% of homology with phosphoenolpyruvate carboxylase (gpu SWI17843_1) of *Selenicereus wittii*. The sequence of amino acids derived from *Avicennia marina* shown in Seq. ID No. 44 has 84% of homology with putative chaperonin (gp ATAC021640_16) of *Arabidopsis thaliana*. The sequence of amino acids derived from *Avicennia marina* shown in Seq. ID No. 46 has 88% of homology with hypothetical protein T5F17.40 (pir T10653) of *Arabidpsis theliana*.

Further, the sequence of amino acids derived from *Salsola komarvii* shown in Seq. ID No. 48 has 63% of homology with cysteine proteinase inhibitor (pir T07139) of *Glycine max*. The sequence of amino acids derived from *Salsola komarvii* shown in Seq. ID No. 50 has 87% of homology with nucleotide sugar epimerase-like protein (gp ATCHRIV73_17) of *Arabidopsis thaliana*. The sequence of amino acids derived from *Sueada japonica* shown in Seq. ID No. 52 has 57% of homology with putative protein (gp ATF20K12_12) of *Arabidopsis theliana*. The sequence of amino acids derived from *Sueada japonica* shown in Seq. ID No. 54 has 78% of homology with putative WD-40 repeat protein (gp AC006569_14) of *Arabidopsis thaliana*. The sequence of amino acids derived from *Avicennia marina* shown in Seq. ID No. 56 has 75% of homology with cdc2MsE gene product (gp MSCDC2MSE_1) of *Medicago sativa*. The sequence of amino acids derived from *Sueada japonica* shown in Seq. ID No. 58 has 39% of homology with putative protein (gp ATF17C15_9) of *Arabidopsis thaliana*. The sequence of amino acids derived from *Salsola komarovii* shown in Seq. ID No. 60 has 66% of homology with transcription factor E2F (prf 2601241A) of *Nicotiana tabacum*. The sequence of amino acids derived from *Salsola komarovii* shown in Seq. ID No. 62 has 34% of homology with hypothetical protein T26B15.5 (pir T02548) of *Arabidopsis thaliana*. The sequence of amino acids derived from *Mesembryanthemum crystallinum* shown in Seq. ID No. 64 has 30% of homology with *Homo sapiens* cDNA FLJ10298 fis, clone NT2RM1001115, weakly similar to ENDOCHITINASE 2 PRECURSOR (EC 3.2.1.14) (pir T02548).

EXAMPLE 4

Effects of Mangrove cDNA in Yeast

Figure 3:
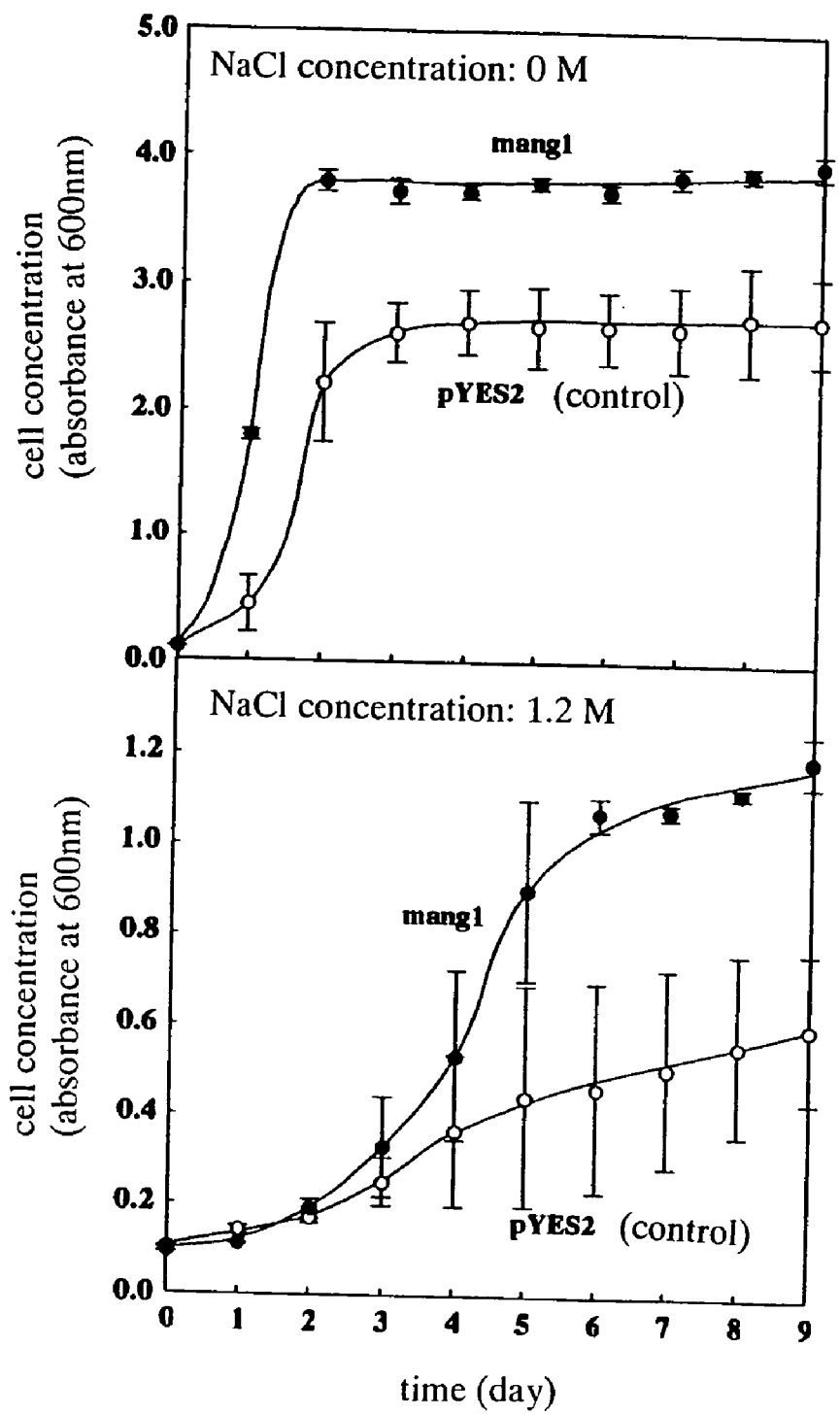
FIG. 3 shows the result of measuring the time-course growth of the yeast introduced with mang1 under the condition of high concentration of salt. Cell concentration was used as an index for detection. As a control, a vector (pYES2) was used alone. Measurement was carried out with two levels of salt (NaCl) concentrations.

The pBluescript SK cloned with cDNA shown in Seq. ID No. 1 was digested by restriction enzymes EcoRI or NotI, and was subjected to agarose gel electrophoresis. About 1 kb fragment obtained here was excised, and was purified with GENECLEAN kit (BIO101). By using Ligation Kit ver2 (TAKARA), the fragments were introduced into yeast expression vectors pYES2 (Invitrogen) which were digested with restriction enzymes EcoRI and NotI. Next, the vectors are introduced into yeast by means of electoroporation. *Saccharomyces ceriviciae* YM4271 (Clontech) was used as yeast. SD agar medium which does not contain uracil (hereafter, -UraSD agar medium) was used to select transformed yeast. The salt tolerance of transformed yeast was evaluated in the following way. Transformed yeast was cultured on -UraSD medium until the late period of the logarithmic growth phase inoculated on -UraSD medium containing 1200 mM of NaCl and -Ura SD medium not containing NaCl (the primary concentration is OD600=0.1), and was subject to shaking culture at 30° C. The cell suspension was extracted every 24 hours, and its absorbance was measured. UV-1200 (SHIMAZU SEISAKUSHO) was used to measure the absorbance. The same measurement was carried out to make comparison with yeast wherein only pYES2 vectors were introduced. FIG. 3 shows the result of the measurements. As obvious from FIG. 3, the cDNA in yeast obtained by the screening showed similar function of salt tolerance as the ones in coliform.

EXAMPLE 5

Effects of Mangrove cDNA in Tobacco Cultured Cells

Figure 4:
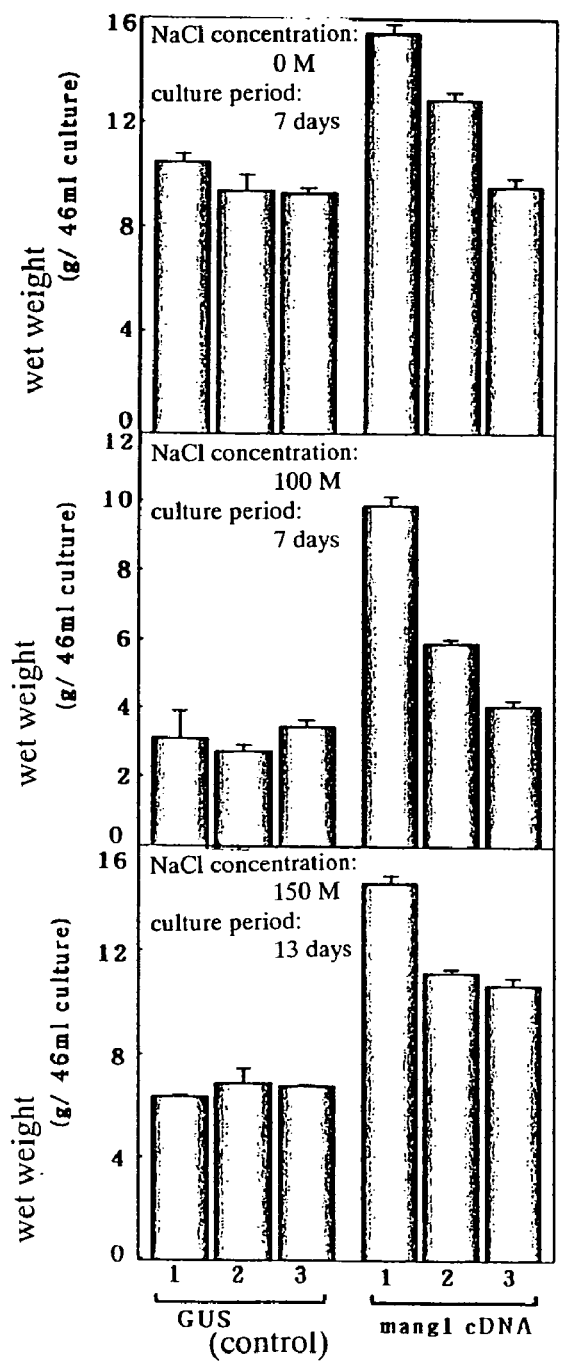
FIG. 4 shows the result of measuring the growth of the tobacco-cultured cells wherein mang1 was introduced under the condition of high concentration of salt. Wet weight was used as an index for detection. As a control, a vector (GUS) was used alone. Measurement was carried out with three concentrations of salt (NaCl).

The pBluescript SK cloned with cDNA shown in Seq. ID No. 1 was digested by the restriction enzymes Xba1 and Xho1, and was subjected to agarose gel electrophoresis. About 1 kb fragment obtained here was excised, and purified by GENECLEAN kit (BIO101). By using Ligation Kit ver2 (TAKARA), the fragments were introduced into the restriction enzymes EcoRI and NotI sites of plant expressing vector pBI101 (EMBO J. 6, 3901–3907, 1987). The obtained plasmids were introduced into *Agrobacterium tumefaciens*, by the electoroporation method, and were infected to tobacco cultured cells (*Nicotiana tabacum* L. Cv. Bright Yellow 2). It is well known to use *Agrobacterium tumefaciens* in introducing genes into plant cells. Here, *Agrobacterium tumefaciens* EHA 101 was used as *Agrobacterium*, and the method of An was used (Plant Physiol. 79, 568–570, 1985). The salt tolerance of transformed tobacco cultured cells were evaluated in the following way. Callus of transformed tobacco cultured cells were collected, and was cultured on Lins-Mayer medium until the late period of the logarithmic growth phase. The obtained Callus were separated 1 ml for each on 45 ml of Lins-Mayer media which were prepared to be 0, 100, or 150 mM of NaCl concentrations, and were subjected to shaking culture at 26° C. On days 7 to 13 after the culture began, cells were collected from cell suspension, and their wet weight was measured. Tobacco culture cells wherein pBI101 was used instead of mangrove cDNA for introduction of GUS genes were measured in the same manner. FIG. 4 shows the result of the measurements. As is obvious from FIG. 4, the cDNA in tobacco culture cells obtained by the screening showed similar function of salt tolerance as the ones in coliform.

EXAMPLE 6

Effects of Mangrove cDNA in Tobacco (Plants)

Figure 5:
FIG. 5 shows the result of measuring the growth of the tobacco plant organisms wherein mang1 was introduced under the condition of high concentration of salt (150 mM of NaCl). A and C indicate the tobaccos wherein a vector (GUS) alone was introduced, and B and D indicate the tobaccos wherein mang1 is introduced.
Figure 5:
Figure 5:
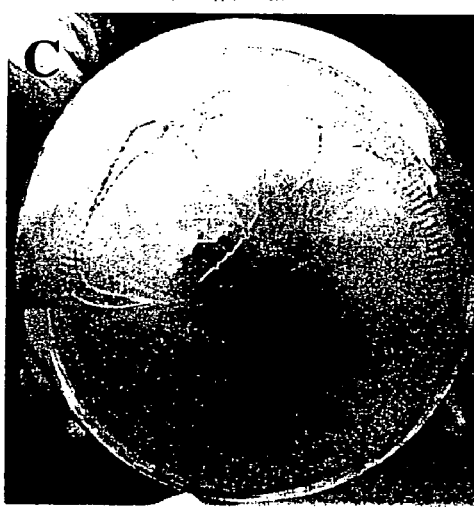
Figure 5:
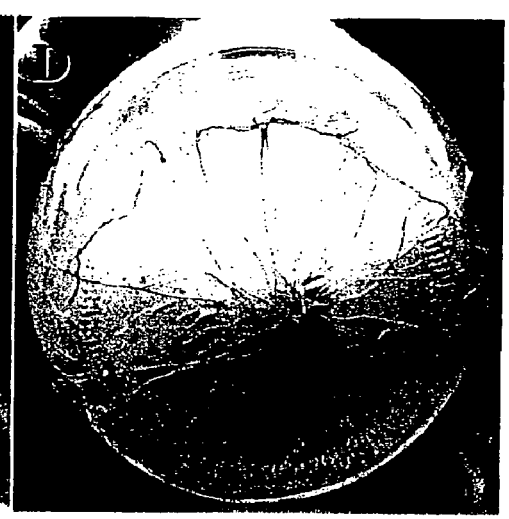

Plasmids obtained by Example 5 were introduced into *Agrobacterium tumefaciens* by electoroporation, and the plasmids were infected to tobacco leafdisks. It is well known to use *Agrobacterium tumefaciens* in introducing genes into tobacco leafdisks. Here, *Agrobacterium tumefaciens* EHA 101 was used as *Agrobacterium*, and it was carried out following the method described in Shokubutu Saiboo Koogaku Nyuumon (Introduction to plant cell engineering) (Japan Scientific Societies Press, 1998). The salt tolerance of transformed tobacco (plant organism) was evaluated in the following way. Transformed tobacco was planted on MS agar medium where the concentration of NaCl was prepared to be 150 mM, and was cultured at 26° C. under lighting of the lighting cycle (light: 16 hours/dark: 8 hours). The growth of the plant organisms after 30 days of culture was observed, and its salt tolerance was evaluated. Tobacco culture cells into which GUS genes were introduced by pBI101 rather than mangrove cDNA were examined in the same fashion. FIG. 5 shows the result (see also the photos). As obvious from FIG. 5, the roots, leaves, and stems of the tobacco plant organisms obtained from the result of screening show a high rate of growth. This confirms that cDNA obtained from the result of screening have functions of improving salt tolerance at the level of plant organism.

EXAMPLE 7

Figure 6:
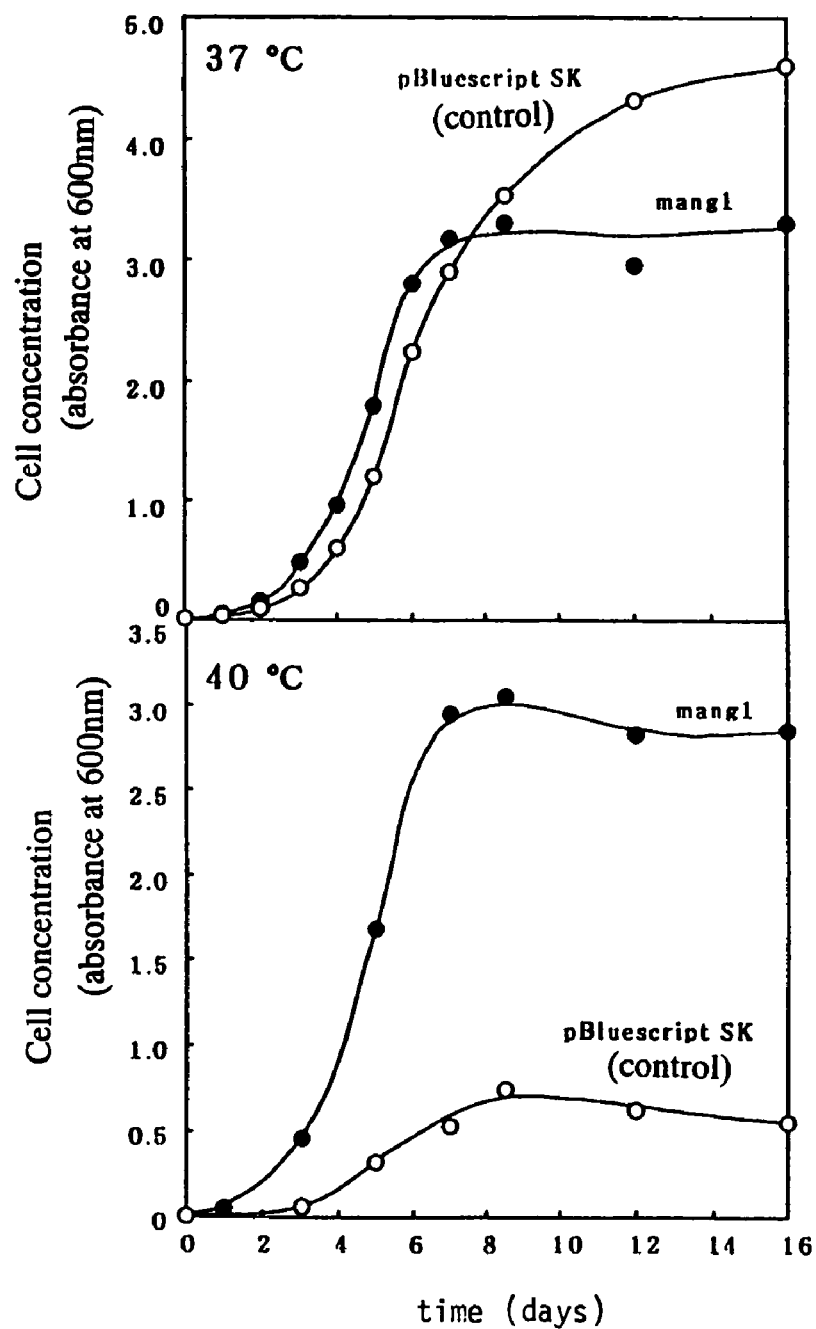
FIG. 6 shows the result of examining thermal stress tolerance of coliforms (SOLR) wherein mang1 was introduced. The thermal stress tolerance was evaluated with the growing curve in the culture at 40° C. as an index. As a control, the SOLR introduced with a vector (pBluesript SK) alone was used.

Effects of Mangrove cDNA Against Various Environmental Stresses (1) Thermal Stress SOLR into which cDNA was cloned shown in Seq. ID No. 1 and pBluescript SK was introduced was cultured in 2YT liquid medium containing 50 µg/ml of kanamycin, 50 µg/ml of ampicillin, 0.05 mM of IPTG at 37° C., and 40° C. As a control, SOLR wherein pBluescript SK, a vector, was introduced as a vector was examined in the same manner. FIG. 6 shows the result. As obvious from FIG. 6, cDNA obtained from the result of screening have functions of improving thermal tolerance.

(2) Osmotic Pressure Stress

Figure 7:
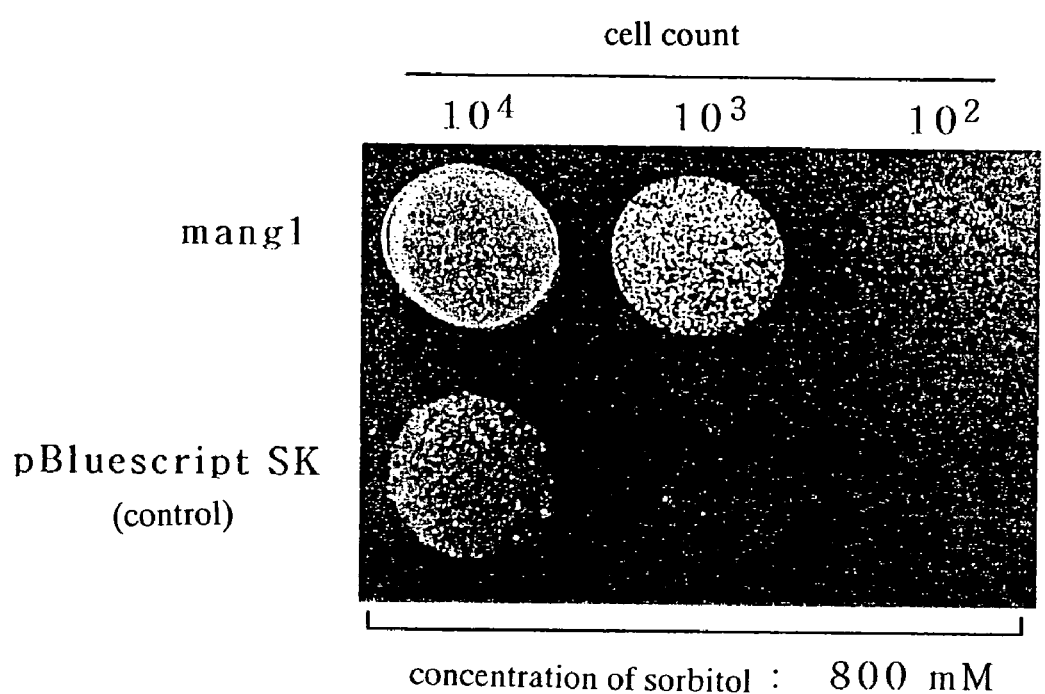
FIG. 7 shows the result of examining the osmotic pressure tolerance of the coliforms (SOLR) wherein mang1 was introduced. The osmotic pressure tolerance was evaluated with the growth on 2YT agar medium containing 800 mM of sorbitol as an index. As a control, the SOLR introduced with a vector (pBluescript SK) alone was used.

SOLR wherein cDNA was cloned shown in Seq. ID No. 1 and pBluescript SK was introduced was cultured in 2YT liquid medium containing 50 µg/ml of kanamycin, 50 µg/ml of ampicillin, 0.05 mM of IPTG until the logarithmic growth phase. Dilution series were produced on 2YT liquid medium, and were spotted each for 25 µl on 800 mM of 2YT agar medium. After the liquid was air-dried, culture was carried out at 37° C. overnight. FIG. 7 shows the result. As seen from FIG. 7, it was confirmed that cDNA obtained from the screening have functions of improving osmotic pressure tolerance.

(3) Freezing Stress

Figure 8:
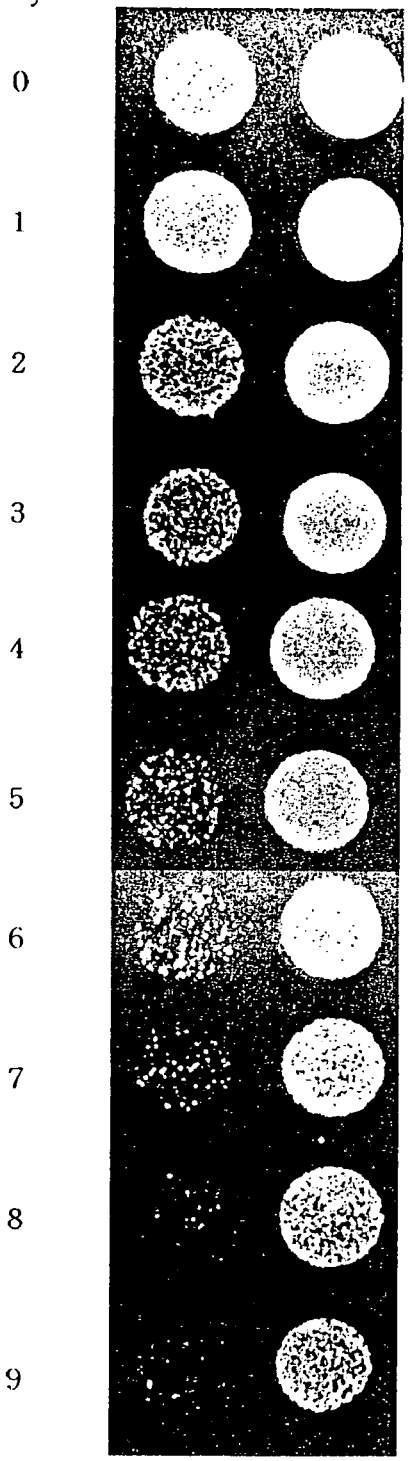
FIG. 8 shows the result of examining the freezing stress tolerance of coliforms (SOLR) wherein mang1 was introduced. The freezing stress tolerance was evaluated with the growth of cell bodies treated with freezing and melting method on 2YT agar medium. As a control, a SOLR wherein only vectors (pBluescript SK) were introduced was used.

SOLR wherein cDNA was cloned shown in Seq. ID No. 1 and pBluescript SK was introduced was cultured in 2YT liquid medium containing 50 µg/ml of kanamycin, 50 µg/ml of ampicillin, 0.05 mM of IPTG until the logarithmic growth phase, and was diluted to be 5000 cells/25 µl on 2YT liquid medium. The cells were transferred to plastic tubes, and they were frozen by liquid nitrogen for 3 minutes and melt at 37° C. for 10 minutes repeatedly. Part of the cell body (25 µl) was taken when melted, and SOLR was spotted on 2YT agar medium containing 50 µg/ml of kanamycin, 50 µg/ml of ampicillin, 0.05 mM of IPTG. As a control, SOLR wherein pBluescript SK, a vector, was introduced as a vector was examined in the same manner. FIG. 8 shows the result. As obvious from FIG. 8, cDNA obtained from the screening have functions of improving tolerance against freezing.

EXAMPLE 8

Molecular Evolution of Proteins Having the Activity of Improving Environmental Stress Tolerance It was attempted to introduce random mutants into the region considered to be mangrin minimal functional region (mangrin core) by performing PCR using plasmids cloned with regions considered to be mangrin cDNA minimal functional region (Amino Acid Number: 17–86) as a template, as shown in FIG. 2. As primers, 5'-GCTCTGAGAAC-CGTCTAGACTTAGATGAAGGTG-3' shown in Seq. ID No. 65, and 5'-TCTCTCGTTCATCTCGAGCTATTA-CAGCTC-3' shown in Seq. ID No. 66 were used. These primers were designed to amplify mangrin core in a way that initiation codon and termination codon, and restriction enzymes (Xba1, Xho1) sites on the outer sides of the codons, were added. In performing PCR, TAKARA Taq ($Mg^{2+}$ free buffer) (TAKARA) was used as a DNA polymerase. The PCR reactive solution was added to the accompanying buffers to be in the ratios of 1.0 mM of MgCl$_2$, 0.5 mM of MnCl$_2$, 0.25 mM of dNPT Mixture, where 2 pmol/10 µl of each primer and template DNA to 10 pg/10 µl are added. The condition of reaction temperature was set as 92° C. for 30 seconds, 50° C. for 30 seconds, and 72° C. for 90 seconds. This cycle was repeated 30 times, and DNA fragments wherein random mutants were introduced into margin core were obtained. The DNA fragments obtained were digested with XbaI and XhoI, and these are cloned to the vectors (pBluescript SK) already digested with XbaI and XhoI. These were introduced into SOLR, and were selected with the growth on agar medium containing 450 mM of NaCl as an index. Although the sequence of bases are mutated, mutant mangrin core maintaining or improving activity of improving salt tolerance was selected. The sequence of bases is determined on part of obtained clones, and the activity of improving salt tolerance was evaluated by spot test. As shown in FIG. 9, the result shows that 2 clones (c-52, c-80) of a sequence of bases are mutated. Among them, c-80 is mutated in the sequence of amino acids, and this is considered to be a factor of improving functions of salt tolerance in mangrin core. Further, as seen from FIG. 10 for comparing functions of improving stress tolerance, it can be used to improve functions of environmental stress tolerance genes.

INDUSTRIAL APPLICABILITY

The present invention will be an effective means to improve tolerance against environmental stress for various animals. Specifically, the plants whose tolerance against environmental stress tolerance is improved can grow in salt damaged lands, cold regions, deserts, and oceans, where they are difficult to grow. From this fact, it is expected that the amount of agricultural products will increase due to the expansion of farmland. Further, the plants whose environmental stress tolerance is improved contribute to the suppression of global warming due to the global increase of CO$_2$ level globally, as well as to the increase of greenery areas and greening of deserts.

What is claimed is:

1. An isolated DNA encoding a protein comprising the amino acid sequence of SEQ ID NO: 40, and having the activity of improving tolerance at least against salt stress.

2. An isolated DNA comprising the nucleotide sequence of SEQ ID NO: 39.

3. A vector comprising the DNA according to any one of claims 1 to 2.

4. A transformed host cell comprising the vector according to claim 3.

5. The transformed host cell according to claim 4, wherein the host cell is a plant cell.

6. A method for producing a protein having the activity of improving environmental stress tolerance, comprising culturing the transformed host cell according to claim 4, and isolating the protein from the cultured host cell.

7. A transgenic plant comprising the DNA according to any one of claims 1 to 2.

8. A transgenic plant comprising the vector according to claim 3.

9. A transgenic plant part which is obtained from the transgenic plant according to claim 7.

10. An isolated DNA which hybridizes with the DNA according to claim 2 under stringent conditions for hybridization at 65° C. and washing treatment with a buffer containing 0.1×SSC, 0.1% SDS at 65° C., and encodes a protein having the activity of improving tolerance at least against salt stress.

11. A method for producing a transgenic plant, comprising introducing the DNA according to any one of claims 1–2 into a plant cell, and regenerating a transgenic plant from the plant cell.

12. A method for producing a transgenic plant, comprising introducing the vector according to claim 3 into a plant cell, and regenerating a transgenic plant from the plant cell.

13. An isolated DNA comprising the complementary sequence of SEQ ID NO: 39.

* * * * *